United States Patent
Dey et al.

(10) Patent No.: US 8,299,123 B2
(45) Date of Patent: Oct. 30, 2012

(54) CCR10 ANTAGONISTS

(75) Inventors: Kaka Dey, Latham, NY (US);
Donghong Amy Gao, Hopewell Junction, NY (US); Daniel R. Goldberg, Redding, CT (US); Alexander Heim-Riether, Newtown, CT (US); John Edward Mangette, Clifton Park, NY (US); Ingo Andreas Mugge, New Haven, CT (US); Roger John Snow, Danbury, CT (US); Alan David Swinamer, Southbury, CT (US); Jiang-Ping Wu, Danbury, CT (US); Zhaoming Xiong, Brookfield, CT (US); Yu Yang, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 103 days.

(21) Appl. No.: 12/738,087

(22) PCT Filed: Oct. 14, 2008

(86) PCT No.: PCT/US2008/079781
§ 371 (c)(1),
(2), (4) Date: Jul. 29, 2010

(87) PCT Pub. No.: WO2009/052078
PCT Pub. Date: Apr. 23, 2009

(65) Prior Publication Data
US 2011/0039851 A1     Feb. 17, 2011

Related U.S. Application Data

(60) Provisional application No. 60/981,214, filed on Oct. 19, 2007.

(51) Int. Cl.
*A61K 31/195* (2006.01)
*C07C 229/00* (2006.01)
(52) U.S. Cl. .................. 514/563; 562/451; 562/435
(58) Field of Classification Search .................. 514/563; 562/451, 435
See application file for complete search history.

(56) References Cited

U.S. PATENT DOCUMENTS

| | | | |
|---|---|---|---|
| 6,419,573 B1 | 7/2002 | Lise et al. | |
| 2005/0187300 A1* | 8/2005 | Bajji et al. | 514/621 |

FOREIGN PATENT DOCUMENTS

| | | |
|---|---|---|
| CA | 2052894 A1 | 4/1992 |
| DE | 2500692 A1 | 7/1976 |
| DE | 19832009 A1 | 1/2000 |
| EP | 0480258 A2 | 4/1992 |
| EP | 0550900 A1 | 7/1993 |
| WO | 9936393 A1 | 7/1999 |
| WO | 2004006858 A2 | 1/2004 |

OTHER PUBLICATIONS

Bock et al.CAS:144:488407, 2006.*
Bock et al. CAS: 144: 488407, 2006.*
Bajji et al. CAS: 143: 248160, 2005.*
Enlert et al. CAS: 123: 256743, 1995.*
McCaskill et al. CAS: 111:221899, 1989.*
Thomae et al. CAS: 87: 67981, 1977.*
International Search Report for PCT/US2008/079781 mailed Feb. 25, 2009.

* cited by examiner

*Primary Examiner* — Rei-tsang Shiao
(74) *Attorney, Agent, or Firm* — Michael P. Morris; Edward S. Lazer

(57) ABSTRACT

The invention relates to a compound of formula (I):

or a tautomer thereof or a pharmaceutically acceptable salt thereof, wherein $R^1$ to $R^{11}$, W, X, Y, Z, and n are as defined herein. The invention also relates to methods of using the compounds of formula (I) and compositions thereof to treat various diseases and disorders in a patient. The invention also relates to processes for preparing the compounds of formula (I) and intermediates useful in these processes.

8 Claims, No Drawings

CCR10 ANTAGONISTS

BACKGROUND OF THE INVENTION

1. Field of the Invention

This invention relates to substituted amides that are useful as inhibitors of CCR10 activity and are thus useful for treating a variety of diseases and disorders that are mediated or sustained through the activity of CCR10 including inflammatory skin diseases, allergic asthma and melanoma. This invention also relates to pharmaceutical compositions comprising these compounds, methods of using these compounds in the treatment of various diseases and disorders, processes for preparing these compounds and intermediates useful in these processes.

2. Brief Description of the Art

Chemokine receptors play an important role in mediating tissue specific recruitment of leukocytes to sites of inflammation. Within the blood there is a subset of memory T cells that preferentially homes to the skin. This subset is defined by expression of the cutaneous lymphocyte antigen (CLA), a lectin, which binds to E-selectin on dermal endothelial cells and promotes trafficking. Although the subset of CLA-expressing cells constitutes only 10-15% of the circulating T cell pool, these cells are found in abundance within several inflammatory skin lesions, for example, psoriasis, contact sensitivity and allergic dermatitis.

Recent studies have revealed that $CLA^+$ memory cells also express the chemokine receptor CCR10 and that cells expressing CCR10 are enriched in inflammatory skin lesions. One ligand for this receptor, CCL27, is also markedly up-regulated at these sites suggesting that this chemokine receptor may participate in mediating the tissue-specific trafficking of $CLA^+$ memory T cells. Within the skin, expression of CCR10 has been reported on $CLA^+$ T cells, melanocytes, fibroblasts, and microvascular endothelial cells. CCL27 expression has been shown to be tightly regulated with abundant expression in the epidermis, predominantly by keratinocytes.

There is evidence in both humans and in rodents that the CCR10-CCL27 interaction plays an important role in the trafficking of inflammatory T cell subsets to skin lesions (J. Morales et al., Proc Natl Acad Sci USA, 1999, 96: 14470-14475; B. Homey et al., J Immunol 2000; 164: 3465-3470; B. Homey et al., Nature Medicine, 2002; 8: 157-165). By histological analysis, it is clear that, in addition to the increase in epidermal expression of CCL27 observed in psoriatic and atopic dermatitis biopsies, there is also expanded expression of CCL27 into the dermal layer as well. Further, endothelial cells within the vasculature of these lesions also display CCL27, though they are negative for CCL27 message, suggesting that keratinocyte-derived CCL27 can be captured by endothelial cells and presented to circulating leukocytes. Accompanying these changes in the skin is a marked increase in the recruitment of lymphocytes that co-express CLA and CCR10. Consistent with the role of CCL27 in skin inflammation, IL-1 beta and TNF alpha treatment of cultured keratinocytes induces expression of CCL27.

Cutaneous application of nickel, in nickel-allergic humans, led to the up-regulated expression of CCL27 and the subsequent recruitment of $CCR10^+$ lymphocytes. Thus, these studies provide temporal support for the role of CCL27 in attracting $CCR10^+$ cells. Furthermore, in vivo proof of concept has been shown (B. Homey et al., ibid, 2002) in wild-type mice where treatment with a function blocking antibody against CCL27 clearly diminished recruitment and swelling in both DNFB-induced and ovalbumin DTH models of dermatitis. These authors also demonstrated the ability of cutaneous injection of CCL27 to promote local lymphocyte trafficking and inflammation, thus providing proof of concept using both ligand and antibody in relevant animal models. Consistent with its ascribed in vivo role, CCL27 induces calcium flux in $CCR10^+$ cells and mediates the selective chemotaxis of $CLA^+$ $CCR10^+$ lymphocytes in vitro.

Studies, such as those described above, suggest that antagonism of the interaction between CCR10 and its skin derived ligand CCL27 could therefore be of benefit in the treatment of inflammatory skin diseases by blocking the entry and activation of T cells within the skin. One indication for a CCR10 antagonist would be psoriasis. The rationale is based on histological studies of receptor/ligand expression in humans with psoriasis and proof of concept studies in animal models of skin inflammation. From analysis of normal and diseased skin samples, it is clear that the expression of CCR10 is highly regulated and restricted primarily to a subset of skin homing ($CLA^+$) lymphocytes, dermal endothelial cells, and dermal fibroblasts. In addition, CCL27, a ligand for CCR10, is also expressed in keratinocytes. In normal skin, CCL27 is expressed by keratinocytes in the basal layers of the epidermis. However, in the skin of atopic dermatitis and psoriasis patients this ligand is up-regulated with expression extending to the suprabasal layers of the epidermis and histological staining also evident on the dermal microvasculature. The enhanced expression of CCL27 is accompanied by an increased presence of $CCR10^+$ lymphocytes. Finally the proof of concept studies described above demonstrated that a function blocking antibody directed against CCL27 blocked trafficking of lymphocytes and swelling in two murine models of dermatitis.

Based on the pattern of expression for both CCR10 and CCL27 and the above proof of concept studies, CCR10 may also be a promising target for treatment of contact sensitivity and allergic dermatitis. It has been shown recently that CCL27 is increased in the sera of patients with systemic sclerosis (Hayakawa et al., Rheumatol, 2005, 44: 873) and in the dermis of UV-induced cutaneous SLE (systemic lupus erythematosus) lesions (Meller et al. 2005, Arthritis Rheum 52: 1504). Therefore, systemic sclerosis and cutaneous SLE could also be additional indications. In addition, inflammation of the respiratory tract in a murine model of allergic asthma is associated with CCL28 and CCR10 expression suggesting that inhibition of CCR10 activity may also be useful in treatment of allergic asthma (English et al., Immunol Lett. 2006, 03(2):92-100).

Antagonism of CCR10 may also be beneficial for the treatment of melanoma. In a mouse model of melanoma metastasis, it has been demonstrated that melanoma lines expressing CCR10 form tumors more readily than matched CCR10 deficient melanomas and that a blocking antibody against CCL27 can block the growth of these $CCR10^+$ melanoma cells in vivo. These observations, coupled with the finding that many human melanomas express CCR10, provide the rationale for considering this as a further indication (Murakami et al., J Exp Med, 2003, 198: 1337).

BRIEF SUMMARY OF THE INVENTION

In a general aspect, the present invention is directed to the compounds of the following formula (I):

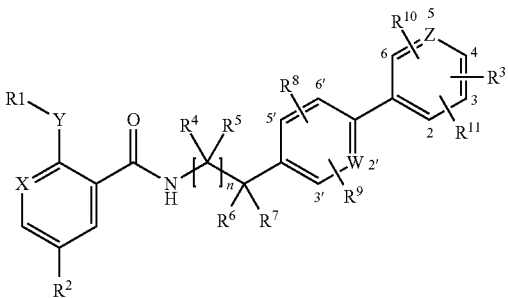

(I)

wherein $R^1$-$R^{11}$, W, X, Y, Z, and n are as defined herein, as well as the tautomers thereof, and salts thereof. It has been found that the compounds of formula (I) have valuable pharmacological properties, particularly an inhibiting activity of CCR10 activity.

In another aspect, the present invention is directed to a method of inhibiting CCR10 activity in an individual comprising administering to the individual a compound described above.

In another aspect, the present invention is directed to a method of treating a disease or disorder associated with the activation of CCR10 comprising administering to an individual a compound described above.

In another aspect, the present invention is directed to a method of treating an inflammatory skin disease comprising administering to an individual a compound described above.

Examples of such diseases that may be treated include, for example, psoriasis, contact sensitivity, allergic dermatitis, systemic sclerosis, and cutaneous SLE.

In another aspect, the present invention is directed to a method of treating allergic asthma comprising administering to an individual a compound described above.

In another aspect, the present invention is directed to a method of treating melanoma comprising administering to an individual in need of such treatment a compound of the present invention as described above.

In yet additional aspects, the present invention is directed to pharmaceutical compositions comprising the above-mentioned compounds, processes for preparing the above-mentioned compounds and intermediates used in these processes.

DETAILED DESCRIPTION OF THE INVENTION

In an embodiment, there are provided compounds of the formula (I)

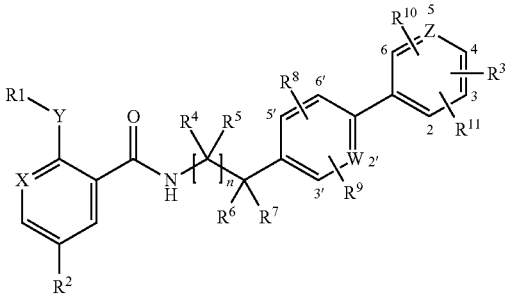

(I)

wherein:
W, X, and Z are independently C or N;
Y is O, NH, or S;
n is 0 or 1;
$R^1$ is
  (a) H;
  (b) $C_{1-8}$alkyl, branched or unbranched, optionally partially or fully halogenated, and optionally substituted with one to two groups selected from —OH, CN, $C_{1-6}$alkoxy, —$CO_2C_{1-6}$alkyl, and —$CON(C_{1-3}$alkyl$)(C_{1-3}$alkyl$)$,
  (c) —$(CH_2)_{0-1}C_{3-8}$cycloalkyl,
  (d) —$CH_2Ar$, wherein Ar is phenyl or heteroaryl selected from pyridinyl, triazolyl, pyrimidinyl, furanyl, thiazolyl, thienyl, pyrrolyl, imidazolyl, and benzofuranyl, each optionally substituted with one to two groups selected from halogen, —CN, —OH, $C_{1-6}$alkyl, $C_{1-6}$alkoxy, —$CF_3$, —$CO_2C_{1-6}$alkyl, and —$CONH_2$, or
  (e) —$(CH_2)_2OCH_2Ar$, wherein Ar is phenyl or heteroaryl selected from pyridinyl, triazolyl, pyrimidinyl, furanyl, thiazolyl, thienyl, pyrrolyl, imidazolyl, and benzofuranyl, each optionally substituted with one to two groups selected from halogen, —CN, —OH, $C_{1-6}$alkyl, $C_{1-6}$alkoxy, —$CO_2C_{1-6}$alkyl, —$C(O)NH_2$; or
if X is C, and Y is O, $R^1$ may form a fused dihydropyran ring with the O it is bound to and X, said dihydropyran ring optionally substituted with one or two methyl groups;
$R^2$ is
  (a) H, $C_{1-6}$alkyl, $C_{1-6}$alkoxy, hydroxy $C_{1-6}$alkyl, halogen, —CN, —$CO_2C_{1-6}$alkyl, —$S(O)_{0-2}C_{1-6}$alkyl, —$NO_2$, —OH, —$CF_3$, —$NH_2$, —$NH(C_{1-6}$alkyl$)$, —$N(C_{1-6}$alkyl$)(C_{1-6}$alkyl$)$, —$NHC(O)NHC_{1-6}$alkyl, —$C(O)NH_2$, —$CONH(C_{1-6}$alkyl$)$, —$CON(C_{1-6}$alkyl$)(C_{1-6}$alkyl$)$, or
  b) phenyl, pyridinyl, triazolyl, or pyrimidinyl, each optionally substituted with one or two groups selected from halogen, $C_{1-6}$alkyl, —CN or $C_{1-6}$alkoxy;
$R^3$ is H, —$CO_2H$, —$(CH_2)_{1-4}CO_2H$, —$(CH_2)_{0-1}C(C_{1-6}$alkyl$)(C_{1-6}$alkyl$)CO_2H$, —$C(C_{1-6}$alkyl$)(C_{1-6}$-alkyl$)CO_2H$, —$O(CH_2)_{1-4}CO_2H$, —$O(CH_2)_{0-1}C(C_{1-6}$alkyl$)(C_{1-6}$alkyl$)CO_2H$, —$OC(C_{1-6}$alkyl$)(C_{1-6}$alkyl$)CO_2H$, —$(CH_2)_{0-1}$-tetrazol-5-yl, —$C(C_{1-6}$alkyl$)(C_{1-6}$alkyl$)$-tetrazol-5-yl, —O—CH$(C_{1-6}$alkyl$)$-tetrazol-5-yl, —$C(O)NHCH_2CO_2H$, or —CN;
$R^4$, $R^5$, $R^6$, and $R^7$ are independently selected from H and $C_{1-6}$alkyl, or $R^4$ and $R^6$ may be joined, together with the carbons they are bonded to, to form a cyclopropane ring;
$R^8$, $R^9$, $R^{10}$, and $R^{11}$ are independently H, halogen, $C_{1-6}$alkyl, $C_{1-6}$alkoxy, —CN, —$CO_2C_{1-6}$alkyl, —$C(O)NH_2$, —$SO_2NH_2$, —$NO_2$, —OH, —$NH_2$, —$CF_3$, or —$CH_2OH$;
or a tautomer thereof or a salt thereof.

In another embodiment there are provided compounds of formula (I) as described above and wherein:
W, X, and Z is C;
Y is O;
n is 1;
$R^1$ is
  (a) H,
  (b) $C_{1-8}$alkyl, branched or unbranched, optionally partially or fully halogenated, and optionally substituted with one to two groups selected from —OH, CN, $C_{1-6}$alkoxy, —$CO_2C_{1-6}$alkyl, —$CON(C_{1-3}$alkyl$)(C_{1-3}$alkyl$)$,
  (c) —$(CH_2)_{0-1}C_{3-8}$cycloalkyl,
  (d) —$CH_2Ar$, wherein Ar is phenyl or heteroaryl selected from pyridinyl, triazolyl, pyrimidinyl, furanyl, thiazolyl, thienyl, pyrrolyl, imidazolyl, and benzofuranyl, each optionally substituted with one to two groups selected from halogen, —CN, —OH, $C_{1-6}$alkyl, $C_{1-6}$alkoxy, —$CF_3$, —$CO_2C_{1-6}$alkyl, and —$CONH_2$, or
  (e) —$(CH_2)_2OCH_2Ar$ wherein Ar is phenyl or heteroaryl selected from pyridinyl, triazolyl, pyrimidinyl, furanyl, thiazolyl, thienyl, pyrrolyl, imidazolyl, and benzofuranyl, each optionally substituted with one to two groups selected from halogen, —CN, —OH, $C_{1-6}$alkyl, $C_{1-6}$alkoxy, —$CO_2C_{1-6}$alkyl, —$C(O)NH_2$; or $R^1$ may be a fused dihydropyran ring with the 0 it is bound to and X, said dihydropyran ring optionally substituted with one or two methyl groups;

$R^2$ is
(a) H, $C_{1-6}$alkyl, $C_{1-6}$alkoxy, hydroxy $C_{1-6}$alkyl, halogen, —CN, —$CO_2C_{1-6}$alkyl, —$S(O)_{0-2}C_{1-6}$alkyl, —$NO_2$, —OH, —$CF_3$, —$NH_2$, —$NH(C_{1-6}$alkyl), —$N(C_{1-6}$alkyl)($C_{1-6}$alkyl), —$NHC(O)NHC_{1-6}$alkyl, —$C(O)NH_2$, —$CONH(C_{1-6}$alkyl), —$CON(C_{1-6}$alkyl)($C_{1-6}$alkyl), or
(b) phenyl, pyridinyl, triazolyl and pyrimidinyl, each optionally substituted with one or two groups selected from halogen, $C_{1-6}$alkyl, —CN or $C_{1-6}$alkoxy;

$R^3$ may be in the 4-position and is H, —$CO_2H$, —$(CH_2)_{1-4}CO_2H$, —$(CH_2)_{0-1}C(C_{1-6}$alkyl)($C_{1-6}$alkyl)$CO_2H$, —$C(C_{1-6}$alkyl)($C_{1-6}$alkyl)$CO_2H$, —$C(O)NH_2$, —$(CH_2)_{0-1}$-tetrazol-5-yl, —$C(C_{1-6}$alkyl)($C_{1-6}$alkyl)-tetrazol-5-yl, —O—$CH(C_{1-6}$alkyl)-tetrazol-5-yl, —$C(O)NHCH_2CO_2H$, or —CN; or $R^3$ may be in the 3-position and is H or $CO_2H$ $R^4$, $R^5$, $R^6$, and $R^7$ are independently H or methyl, or $R^4$ and $R^6$ may be joined, together with the carbons they are bonded to, to form a cyclopropane ring;

$R^8$, $R^9$, $R^{10}$, and $R^{11}$ are independently H, halogen, $C_{1-6}$alkyl, $C_{1-6}$alkoxy, —CN, —$CO_2C_{1-6}$alkyl, —$C(O)NH_2$, —$SO_2NH_2$, —$NO_2$, —OH, —$NH_2$, —$CF_3$, or —$CH_2OH$; or a tautomer thereof or a salt thereof.

In yet another embodiment, there are provided compounds of formula (I) as described above and wherein:
W, X, and Z is C:
Y is O;
n is 1;
$R^1$ is
(a) H,
(b) $C_{1-8}$alkyl, branched or unbranched, optionally partially or fully fluorinated, and optionally substituted with one to two groups selected from —OH, CN and —$OCH_3$,
(c) —$(CH_2)_{0-1}C_{3-8}$cycloalkyl, or
(d) —$CH_2Ar$, wherein Ar is phenyl or heteroaryl selected from pyridinyl and thiazolyl, each optionally substituted with one to two groups selected from halogen, —CN, —$CH_3$, —$OCH_3$, —$CF_3$, and —$CONH_2$; or $R^1$ may form a fused dihydropyran ring with the O it is bound to and X, said dihydropyran ring optionally substituted with one or two methyl groups;

$R^2$ is
(a) —Cl, —Br, —CN, —$CO_2C_{1-6}$alkyl, —$NO_2$, —OH, —$CF_3$, —$NH_2$; or
(b) phenyl, pyridinyl, or pyrimidinyl;

$R^3$ may be in the 4-position and is H, —$CO_2H$, —$(CH_2)_{1-4}CO_2H$, —$(CH_2)_{0-1}C(CH_3)(CH_3)CO_2H$, —$C(CH_3)(CH_3)CO_2H$, —$(CH_2)_{0-1}$tetrazol-5-yl, or —$C(CH_3)(CH_3)$tetrazol-5-yl; or $R^3$ may be in the 3-position and is H or $CO_2H$;

$R^4$, $R^5$, $R^6$, and $R^7$ are independently H or methyl, or $R^4$ and $R^6$ may be joined, together with the carbons they are bonded to, to form a cyclopropane ring;

$R^8$, $R^9$, $R^{10}$, and $R^{11}$ are independently H, F, Cl, $CH_3$, —$OCH_3$, —CN, —$NO_2$, —$NH_2$, or —$CF_3$;
or a tautomer thereof or a salt thereof.

In a further embodiment, there are provided compounds of formula (I) as described above and wherein:
W, X, and Z are C:
Y is O;
n is 1;
$R^1$ is
(a) $C_{1-8}$alkyl, branched or unbranched, optionally partially or fully fluorinated;
(b) —$(CH_2)_{0-1}C_{3-8}$cycloalkyl, or
(c) —$CH_2Ar$, wherein Ar is phenyl or heteroaryl selected from pyridinyl and thiazolyl, each optionally substituted with one to two groups selected from F, —CN, —$CH_3$, —$OCH_3$, and —$CF_3$, $R^2$ is Cl or Br;
$R^3$ is in the 4-position and is H, —$CO_2H$, —$(CH_2)_{1-2}CO_2H$, —$(CH_2)_{0-1}C(CH_3)(CH_3)CO_2H$, —$C(CH_3)(CH_3)CO_2H$, —$(CH_2)_{0-1}$tetrazol-5-yl, or —$C(CH_3)(CH_3)$tetrazol-5-yl;
$R^4$, $R^5$, $R^6$, and $R^7$ are independently H or methyl, or $R^4$ and $R^6$ may be joined, together with the carbons they are bonded to, to form a cyclopropane ring;
$R^8$, $R^9$, $R^{10}$, and $R^{11}$ are independently H, F, Cl, $CH_3$, —$OCH_3$, —CN, —$NO_2$, or —$NH_2$;
or a tautomer thereof or a salt thereof.

In still a further embodiment of the invention, there are provided compounds of the formula (I) selected from the group below or a tautomer thereof or a salt thereof:

| | Structure | Name |
|---|---|---|
| 1. | 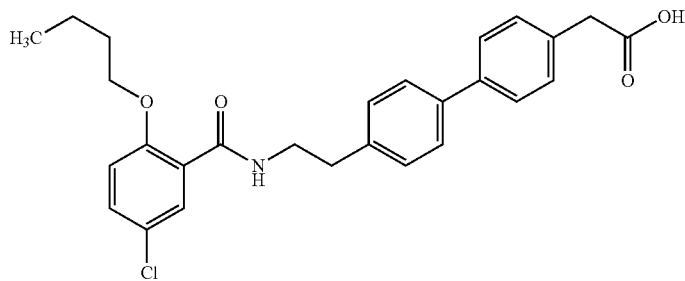 | (4'-{2-[(2-butoxy-5-chlorobenzoyl)amino]ethyl}biphenyl-4-yl)acetic acid |

-continued

| | Structure | Name |
|---|---|---|
| 2. | 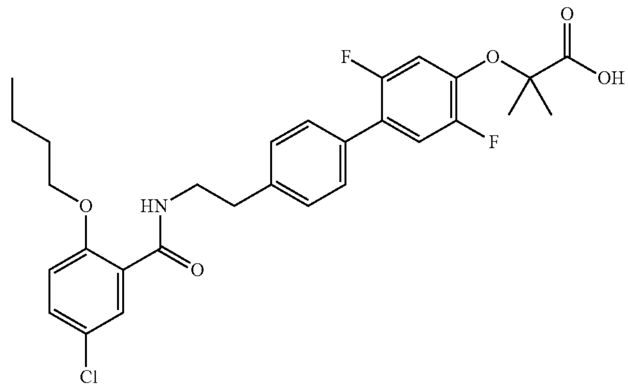 | 2-[(4'-{2-[(2-butoxy-5-chlorobenzoyl)amino]ethyl}-2,5-difluorobiphenyl-4-yl)oxy]-2-methylpropanoic acid |
| 3. | 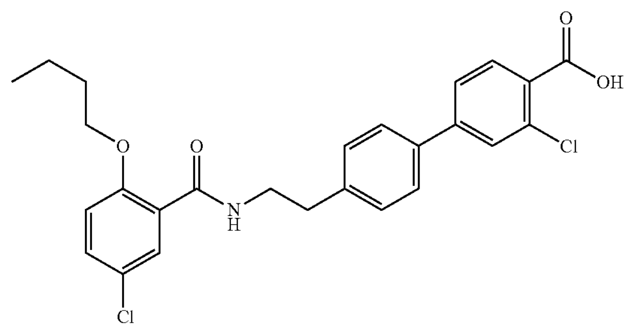 | 4'-{2-[(2-butoxy-5-chlorobenzoyl)amino]ethyl}-3-chlorobiphenyl-4-carboxylic acid |
| 4. | 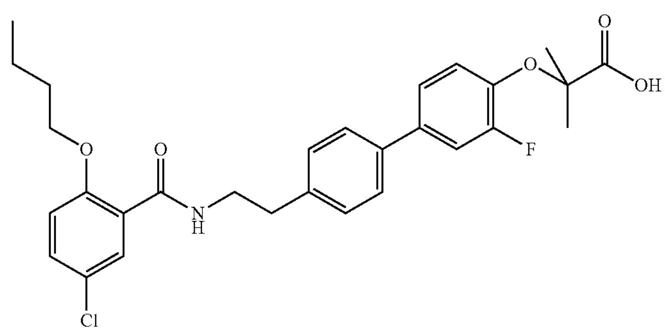 | 2-[(4'-{2-[(2-butoxy-5-chlorobenzoyl)amino]ethyl}-3-fluorobiphenyl-4-yl)oxy]-2-methylpropanoic acid |
| 5. | 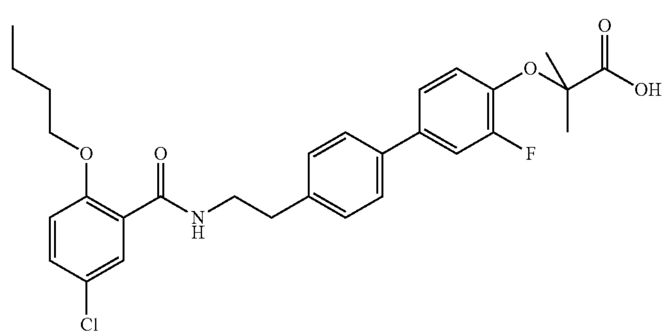 | 2-[(4'-{2-[(5-chloro-2-methoxybenzoyl)amino]ethyl}-2,3-dimethylbiphenyl-4-yl)oxy]-2-methylpropanoic acid |

-continued
| | Structure | Name |
|---|---|---|
| 6. | 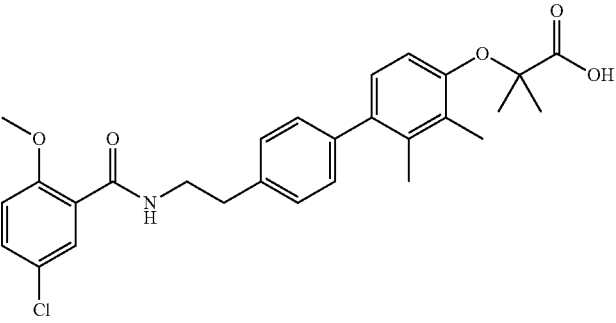 | 2-[(4'-{2-[(2-butoxy-5-chlorobenzoyl)amino]ethyl}biphenyl-4-yl)oxy]-2-methylpropanoic acid |
| 7. | 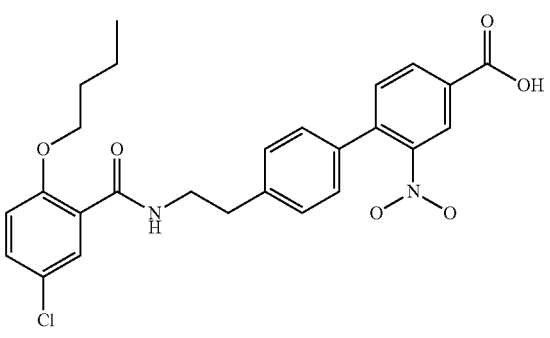 | 4'-{2-[(2-butoxy-5-chlorobenzoyl)amino]ethyl}-2-nitrobiphenyl-4-carboxylic acid |
| 8. | 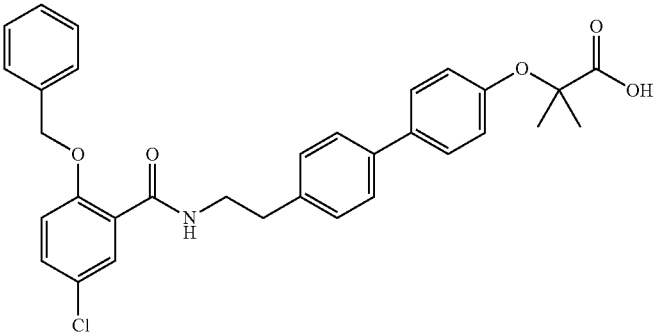 | 2-{[4'-(2-{[2-(benzyloxy)-5-chlorobenzoyl]amino}ethyl)biphenyl-4-yl]oxy}-2-methylpropanoic acid |
| 9. | 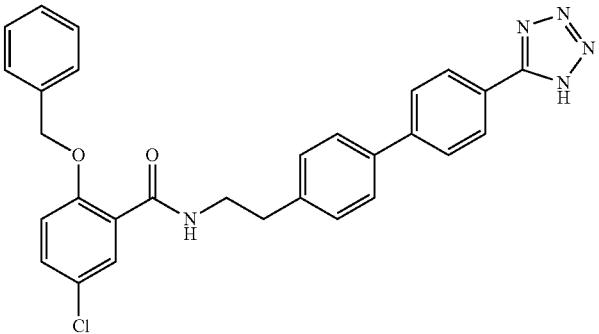 | 2-(benzyloxy)-5-chloro-N-{2-[4'-(1H-tetrazol-5-yl)biphenyl-4-yl]ethyl}benzamide |

-continued

| | Structure | Name |
|---|---|---|
| 10. | 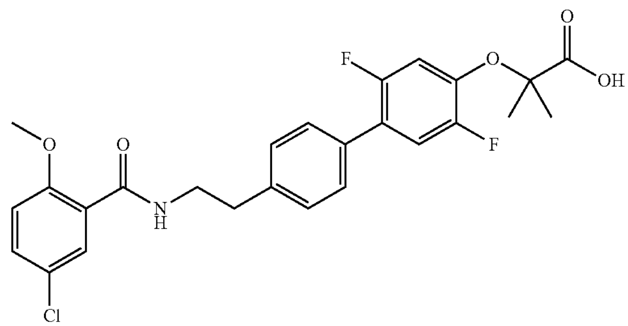 | 2-[(4'-{2-[(5-chloro-2-methoxybenzoyl)amino]ethyl}-2,5-difluorobiphenyl-4-yl)oxy]-2-methylpropanoic acid |
| 11. | 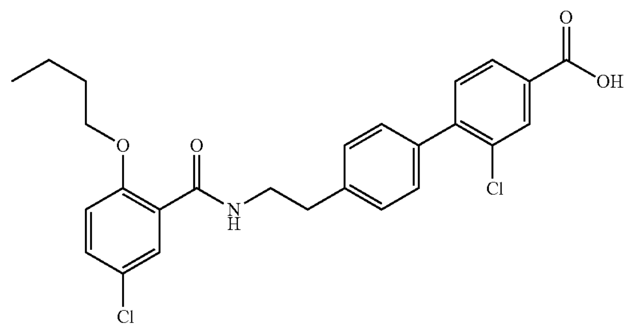 | 4'-{2-[(2-butoxy-5-chlorobenzoyl)amino]ethyl}-2-chlorobiphenyl-4-carboxylic acid |
| 12. | 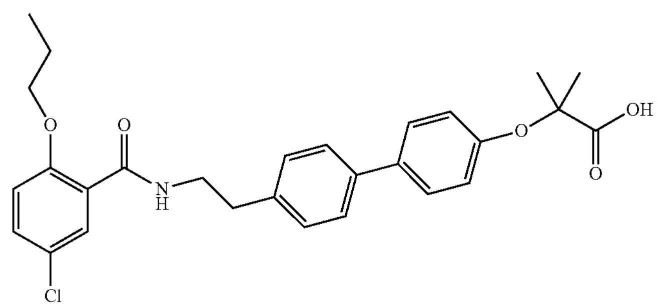 | 2-[(4'-{2-[(5-chloro-2-propoxybenzoyl)amino]ethyl}biphenyl-4-yl)oxy]-2-methylpropanoic acid |
| 13. | 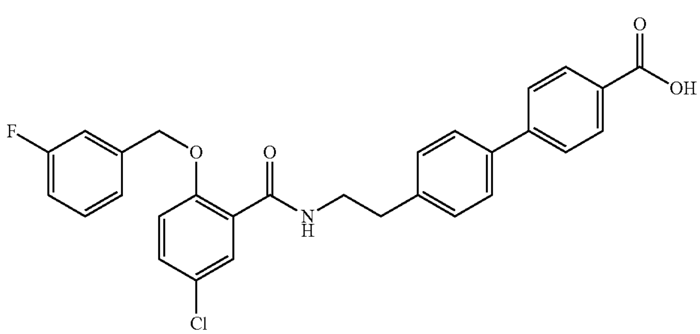 | 4'-[2-({5-chloro-2-[(3-fluorobenzyl)oxy]benzoyl}amino)ethyl]biphenyl-4-carboxylic acid |
| 14. | 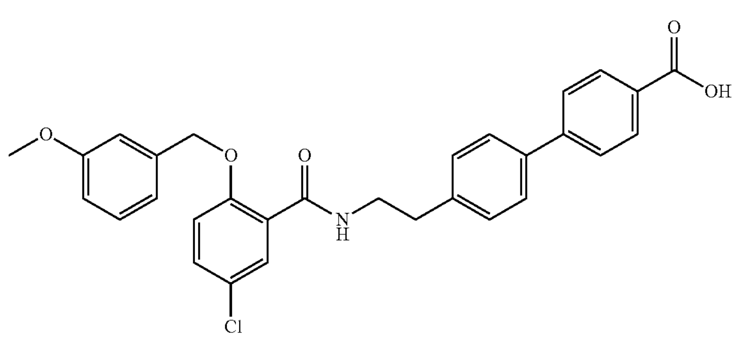 | 4'-[2-({5-chloro-2-[(3-methoxybenzyl)oxy]benzoyl}amino)ethyl]biphenyl-4-carboxylic acid |

-continued

| | Structure | Name |
|---|---|---|
| 15. | 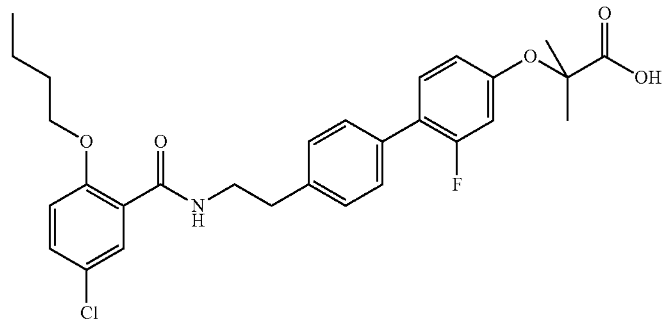 | 2-[(4'-{2-[(2-butoxy-5-chlorobenzoyl)amino]ethyl}-2-fluorobiphenyl-4-yl)oxy]-2-methylpropanoic acid |
| 16. | 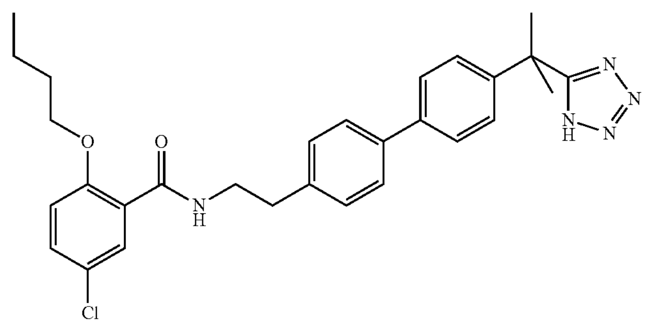 | 2-butoxy-5-chloro-N-(2-{4'-[1-methyl-1-(1H-tetrazol-5-yl)ethyl]biphenyl-4-yl}ethyl)benzamide |
| 17. | 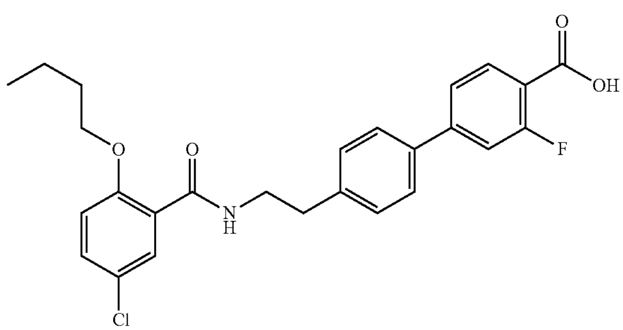 | 4'-{2-[(2-butoxy-5-chlorobenzoyl)amino]ethyl}-3-fluorobiphenyl-4-carboxylic acid |
| 18. | 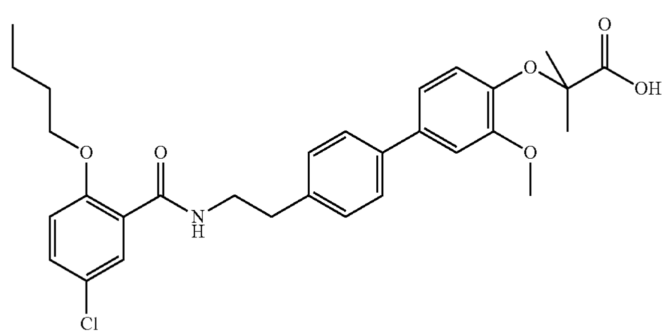 | 2-[(4'-{2-[(2-butoxy-5-chlorobenzoyl)amino]ethyl}-3-methoxybiphenyl-4-yl)oxy]-2-methylpropanoic acid |

-continued

| | Structure | Name |
|---|---|---|
| 19. | 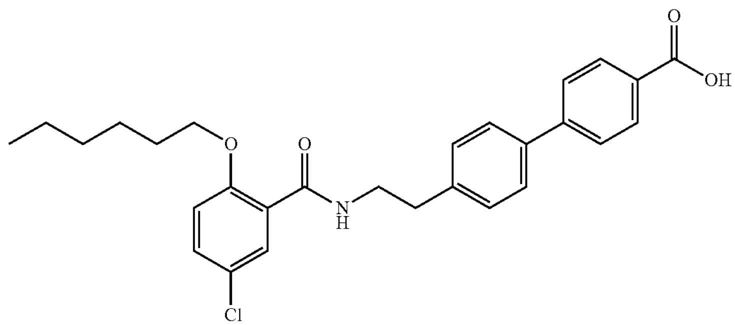 | 4'-(2-{[5-chloro-2-(hexyloxy)benzoyl]amino}ethyl)biphenyl-4-carboxylic acid |
| 20. | 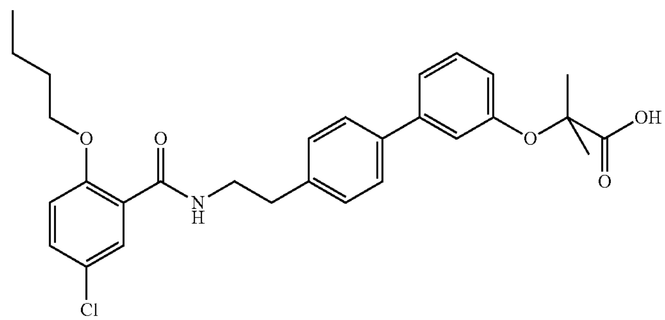 | 2-[(4'-{2-[(2-butoxy-5-chlorobenzoyl)amino]ethyl}biphenyl-3-yl)oxy]-2-methylpropanoic acid |
| 21. | 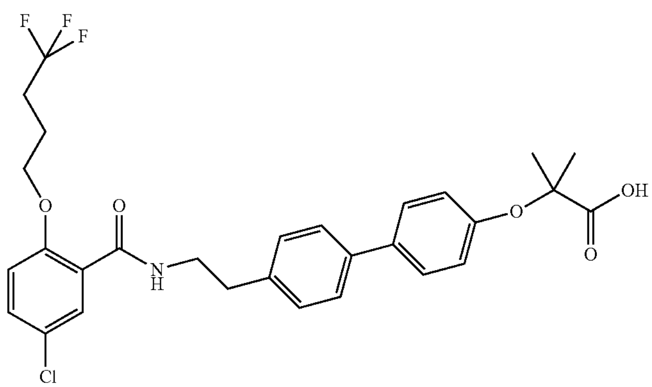 | 2-{[4'-(2-{[5-chloro-2-(4,4,4-trifluorobutoxy)benzoyl]amino}ethyl)-biphenyl-4-yl]oxy}-2-methylpropanoic acid |
| 22. | 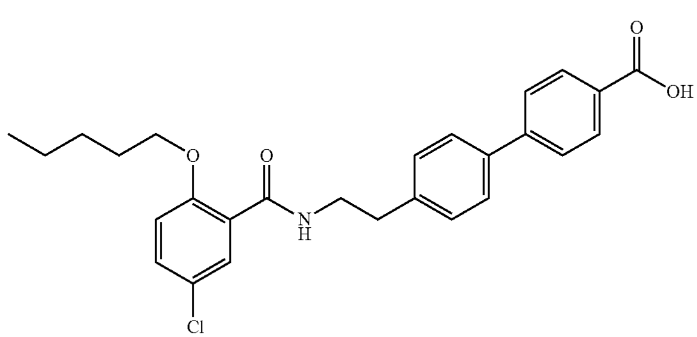 | 4'-(2-{[5-chloro-2-(pentyloxy)benzoyl]amino}ethyl)-biphenyl-4-carboxylic acid |

| | Structure | Name |
|---|---|---|
| 23. | 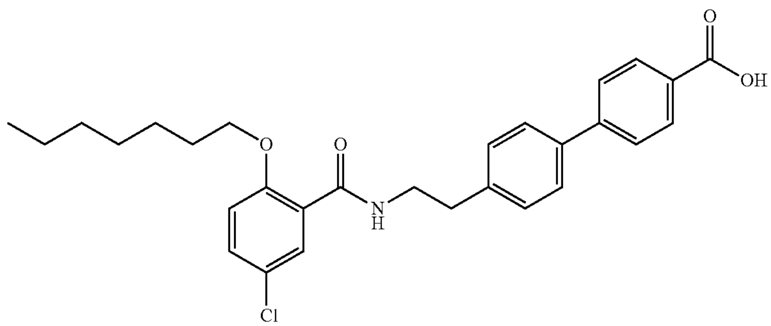 | 4'-(2-{[5-chloro-2-(heptyloxy)benzoyl]amino}ethyl)biphenyl-4-carboxylic acid |
| 24. | 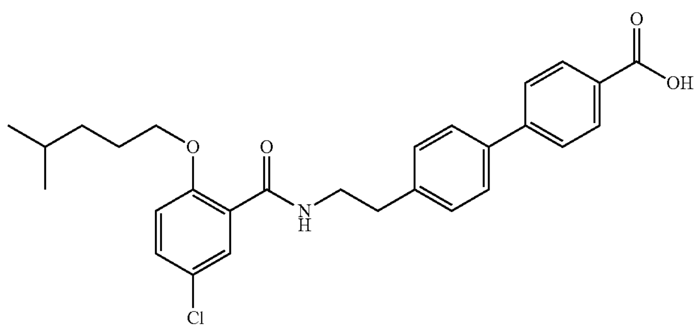 | 4'-[2-({5-chloro-2-[(4-methylpentyl)oxy]benzoyl}amino)ethyl]biphenyl-4-carboxylic acid |
| 25. | 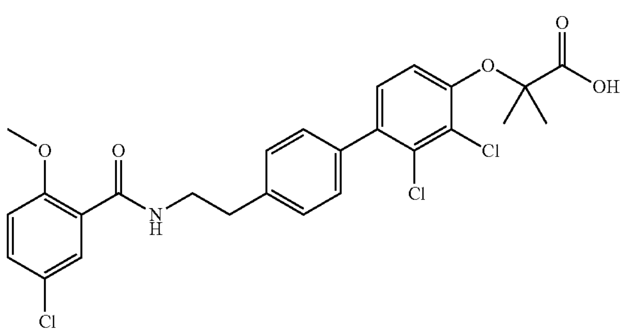 | 2-[(2,3-dichloro-4'-{2-[(5-chloro-2-methoxybenzoyl)amino]ethyl}biphenyl-4-yl)oxy]-2-methylpropanoic acid |
| 26. | 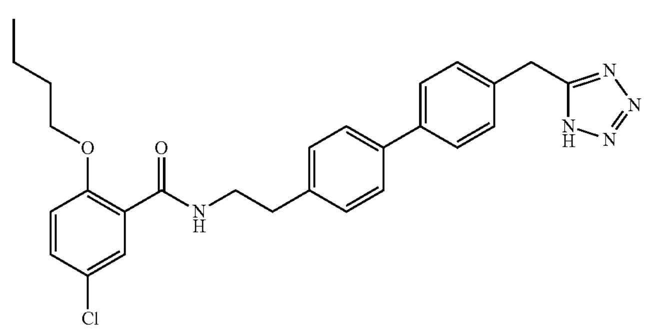 | 2-butoxy-5-chloro-N-{2-[4'-(1H-tetrazol-5-ylmethyl)biphenyl-4-yl]ethyl}benzamide |

-continued

| | Structure | Name |
|---|---|---|
| 27. | 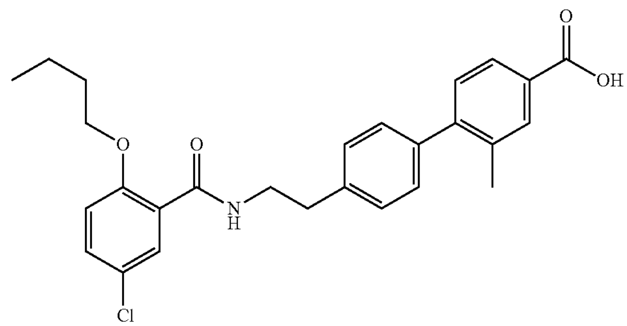 | 4'-{2-[(2-butoxy-5-chlorobenzoyl)amino]ethyl}-2-methylbiphenyl-4-carboxylic acid |
| 28. | 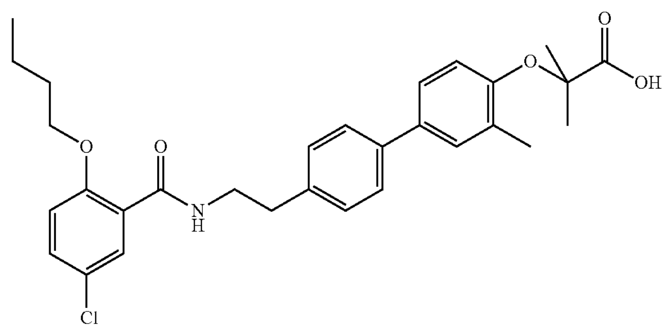 | 2-[(4'-{2-[(2-butoxy-5-chlorobenzoyl)amino]ethyl}-3-methylbiphenyl-4-yl)oxy]-2-methylpropanoic acid |
| 29. | 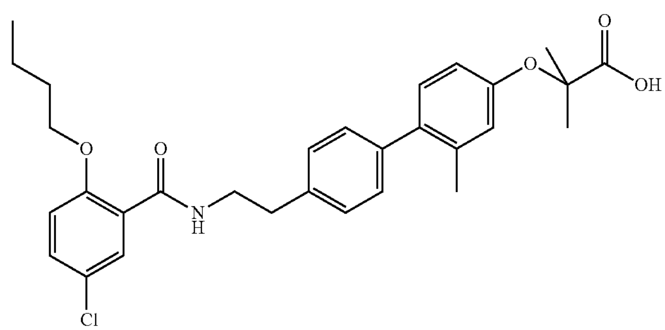 | 2-[(4'-{2-[(2-butoxy-5-chlorobenzoyl)amino]ethyl}-2-methylbiphenyl-4-yl)oxy]-2-methylpropanoic acid |
| 30. | 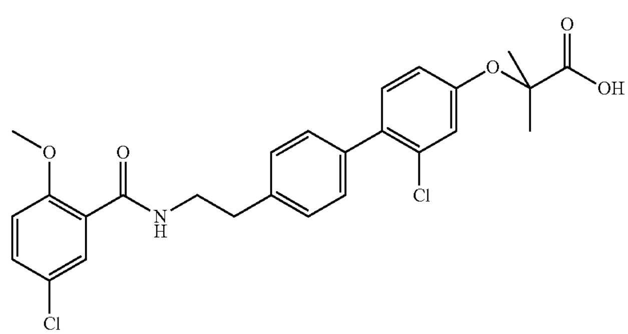 | 2-[(2-chloro-4'-{2-[(5-chloro-2-methoxybenzoyl)amino]ethyl}biphenyl-4-yl)oxy]-2-methylpropanoic acid |

-continued

| | Structure | Name |
|---|---|---|
| 31. | 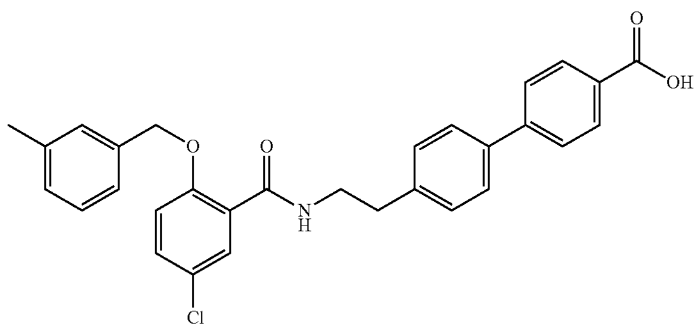 | 4'-[2-({5-chloro-2-[(3-methylbenzyl)oxy]benzoyl}amino)ethyl]biphenyl-4-carboxylic acid |
| 32. | 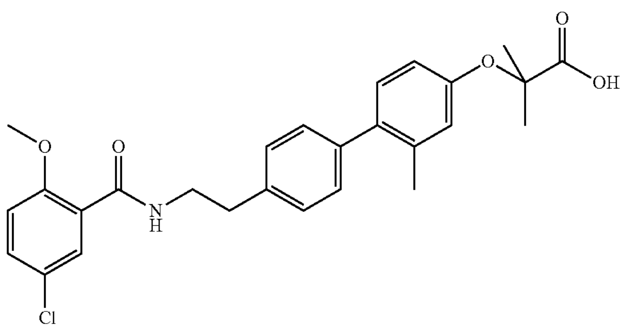 | 2-[(4'-{2-[(5-chloro-2-methoxybenzoyl)amino]ethyl}-2-methylbiphenyl-4-yl)oxy]-2-methylpropanoic acid |
| 33. | 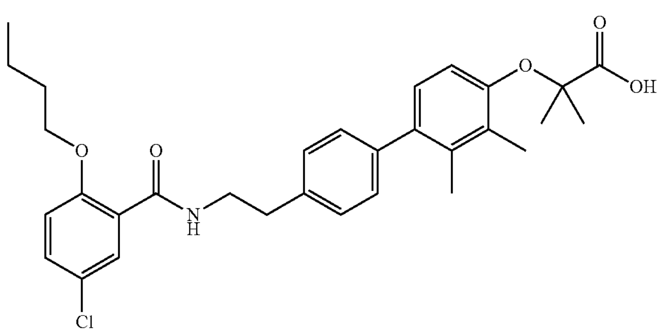 | 2-[(4'-{2-[(2-butoxy-5-chlorobenzoyl)amino]ethyl}-2,3-dimethylbiphenyl-4-yl)oxy]-2-methylpropanoic acid |
| 34. | 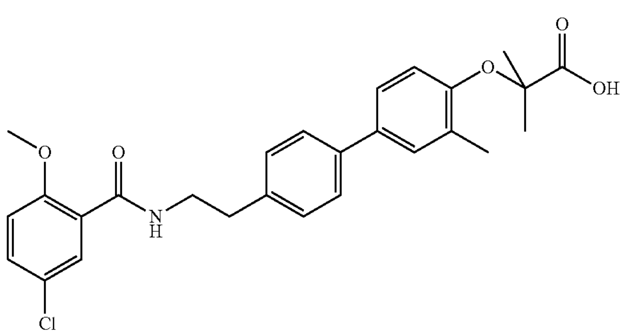 | 2-[(4'-{2-[(5-chloro-2-methoxybenzoyl)amino]ethyl}-3-methylbiphenyl-4-yl)oxy]-2-methylpropanoic acid |

-continued

| | Structure | Name |
|---|---|---|
| 35. | 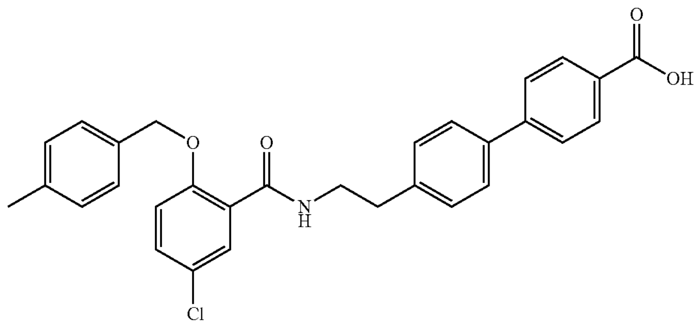 | 4'-[2-({5-chloro-2-[(4-methylbenzyl)oxy]benzoyl}amino)ethyl]biphenyl-4-carboxylic acid |
| 36. | 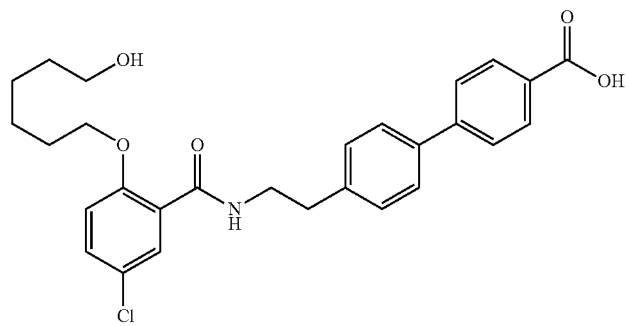 | 4'-[2-({5-chloro-2-[(6-hydroxyhexyl)oxy]benzoyl}amino)ethyl]biphenyl-4-carboxylic acid |
| 37. | 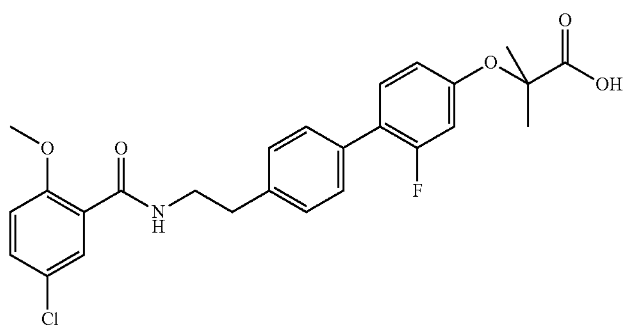 | 2-[(4'-{2-[(5-chloro-2-methoxybenzoyl)amino]ethyl}-2-fluorobiphenyl-4-yl)oxy]-2-methylpropanoic acid |
| 38. | 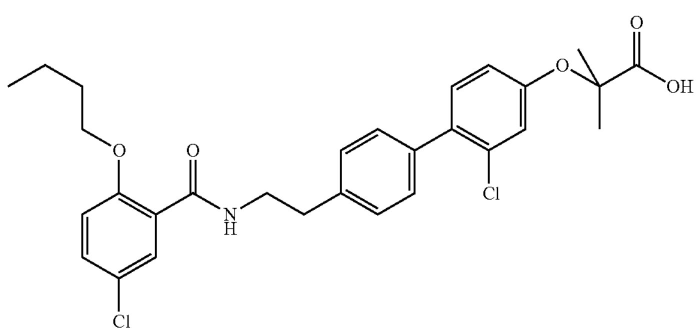 | 2-[(4'-[2-[(2-butoxy-5-chlorobenzoyl)amino]ethyl}-2-chlorobiphenyl-4-yl)oxy]-2-methylpropanoic acid |
| 39. | 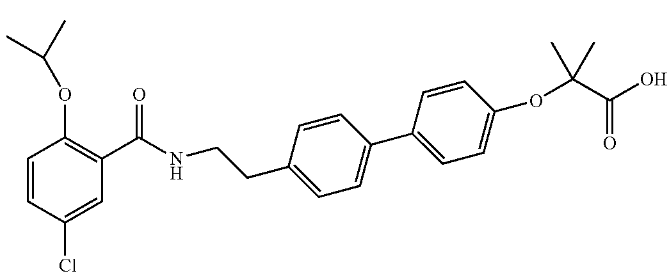 | 2-[(4'-{2-[(5-chloro-2-isopropoxybenzoyl)amino]ethyl}biphenyl-4-yl)oxy]-2-methylpropanoic acid |

-continued

| | Structure | Name |
|---|---|---|
| 40. | 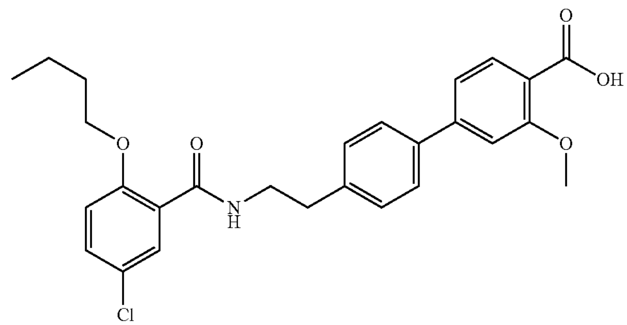 | 4'-{2-[(2-butoxy-5-chlorobenzoyl)amino]ethyl}-3-methoxybiphenyl-4-carboxylic acid |
| 41. | 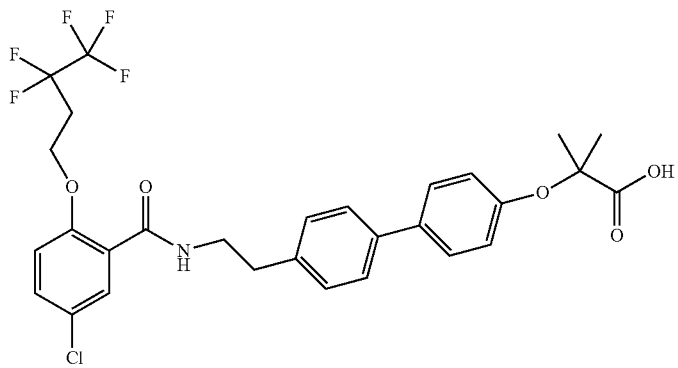 | 2-{[4'-(2-{[5-chloro-2-(3,3,4,4,4-pentafluorobutoxy)benzoyl]amino}ethyl)biphenyl-4-yl]oxy}-2-methylpropanoic acid |
| 42. | 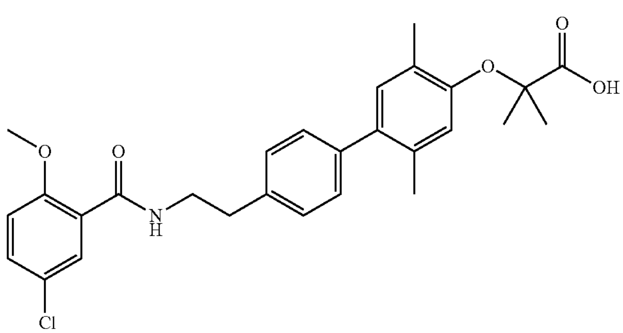 | 2-[(4'-{2-[(5-chloro-2-methoxybenzoyl)amino]ethyl}-2,5-dimethylbiphenyl-4-yl)oxy]-2-methylpropanoic acid |
| 43. | 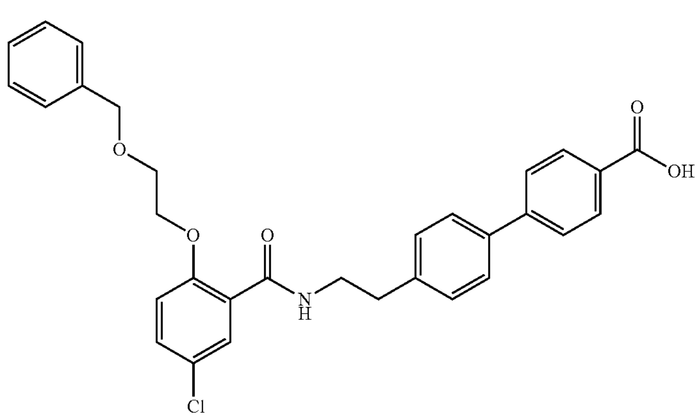 | 4'-[2-({2-[2-(benzyloxy)ethoxy]-5-chlorobenzoyl}amino)ethyl]biphenyl-4-carboxylic acid |

-continued

| | Structure | Name |
|---|---|---|
| 44. | 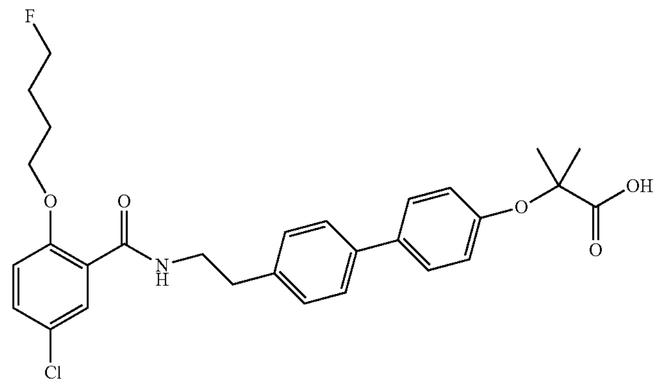 | 2-{[4'-(2-{[5-chloro-2-(4-fluorobutoxy)benzoyl]amino}ethyl)biphenyl-4-yl]oxy]-2-methylpropanoic acid |
| 45. | 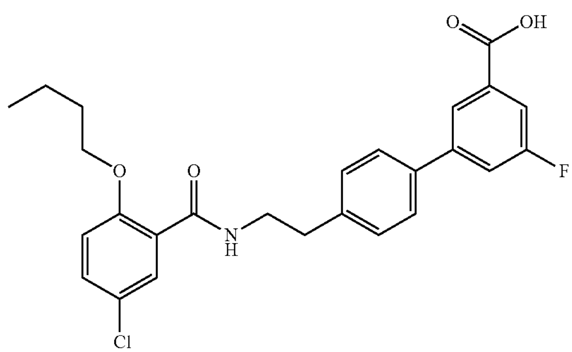 | 4'-{2-[(2-butoxy-5-chlorobenzoyl)amino]ethyl}-5-fluorobiphenyl-3-carboxylic acid |
| 46. | 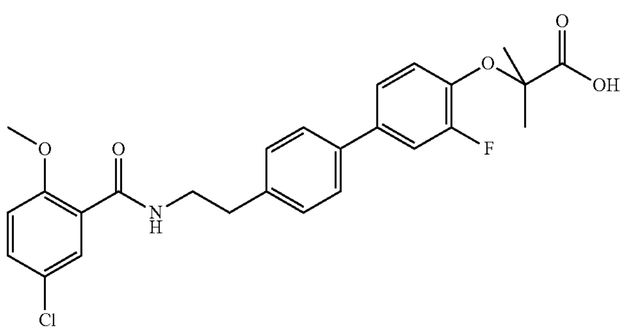 | 2-[(4'-{2-[(5-chloro-2-methoxybenzoyl)amino]ethyl}-3-fluorobiphenyl-4-yl)oxy]-2-methylpropanoic acid |
| 47. | 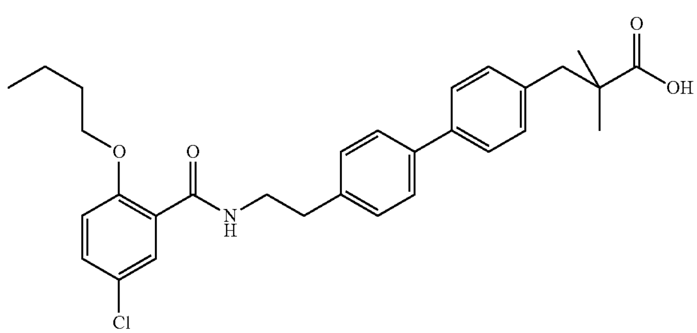 | 3-(4'-{2-[(2-butoxy-5-chlorobenzoyl)amino]ethyl}biphenyl-4-yl)-2,2-dimethylpropanoic acid |

-continued

| | Structure | Name |
|---|---|---|
| 48. | 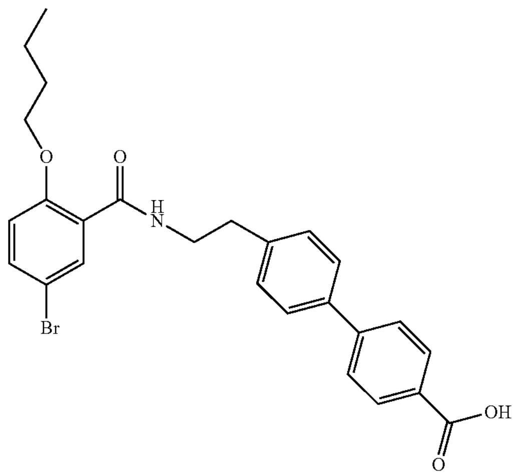 | 4'-{2-[(5-bromo-2-butoxybenzoyl)amino]ethyl}biphenyl-4-carboxylic acid |
| 49. | 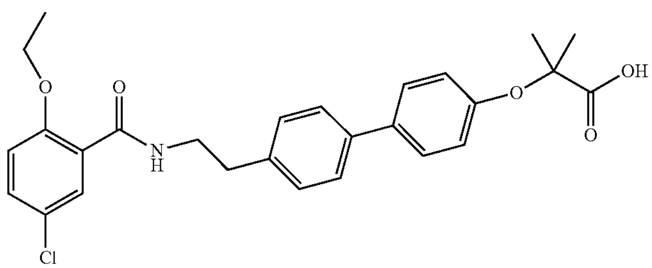 | 2-[(4'-{2-[(5-chloro-2-ethoxybenzoyl)amino]ethyl}biphenyl-4-yl)oxy]-2-methylpropanoic acid |
| 50. | 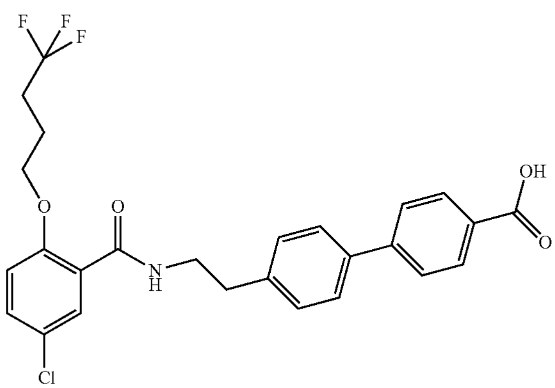 | 4'-(2-{[5-chloro-2-(4,4,4-trifluorobutoxy)benzoyl]amino}ethyl)-biphenyl-4-carboxylic acid |
| 51. | 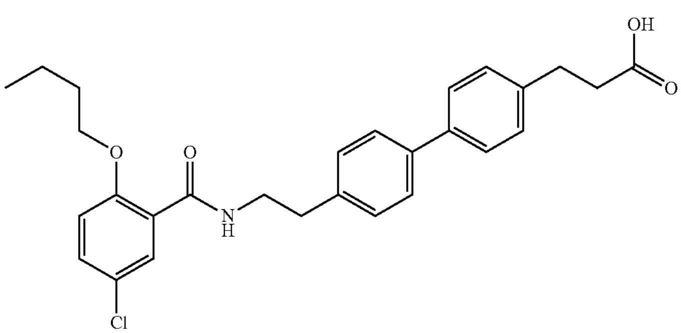 | 3-(4'-{2-[(2-butoxy-5-chlorobenzoyl)amino]ethyl}biphenyl-4-yl)propanoic acid |

-continued

| | Structure | Name |
|---|---|---|
| 52. | 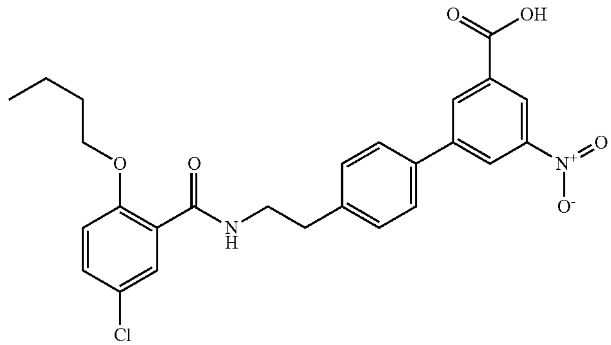 | 4'-{2-[(2-butoxy-5-chlorobenzoyl)amino]ethyl}-5-nitrobiphenyl-3-carboxylic acid |
| 53. | 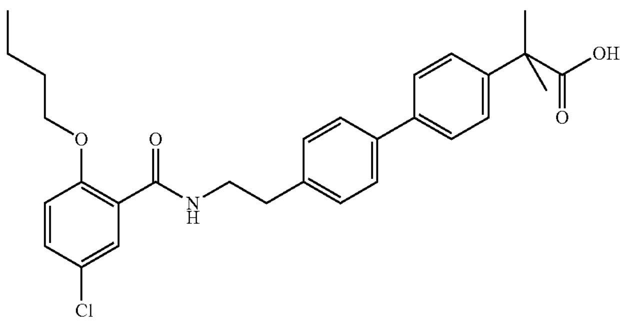 | 2-(4'-{2-[(2-butoxy-5-chlorobenzoyl)amino]ethyl}biphenyl-4-yl)-2-methylpropanoic acid |
| 54. | 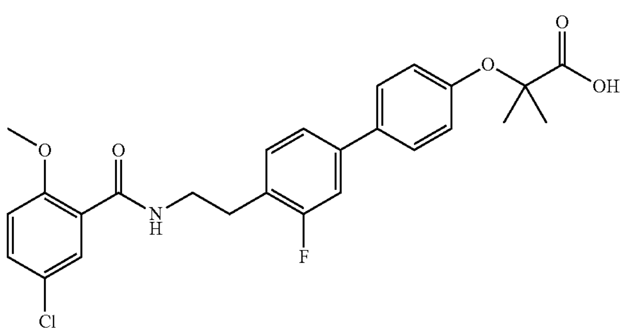 | 2-[(4'-{2-[(5-chloro-2-methoxybenzoyl)amino]ethyl}-3'-fluorobiphenyl-4-yl)oxy]-2-methylpropanoic acid |
| 55. | 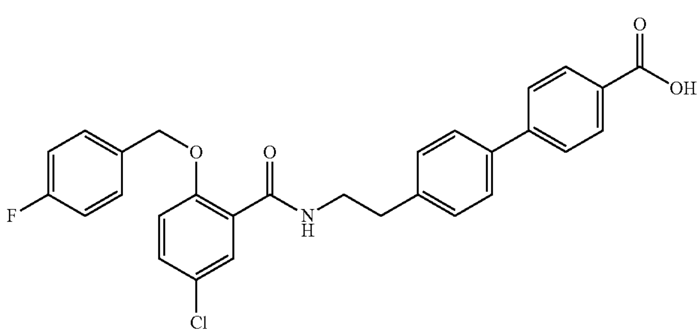 | 4'-[2-({5-chloro-2-[(4-fluorobenzyl)oxy]benzoyl}amino)ethyl]biphenyl-4-carboxylic acid |

-continued

| | Structure | Name |
|---|---|---|
| 56. | 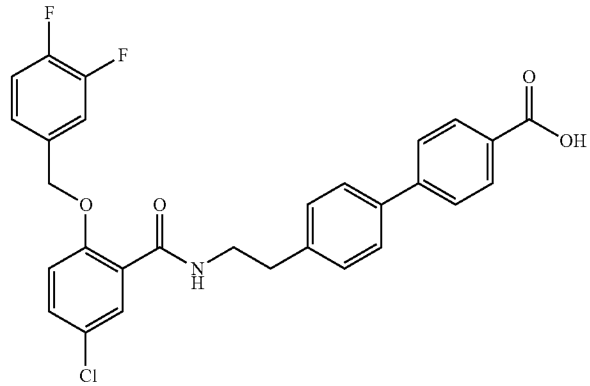 | 4'-[2-({5-chloro-2-[(3,4-difluorobenzyl)oxy]benzoyl}amino]ethyl]biphenyl-4-carboxylic acid |
| 57. | 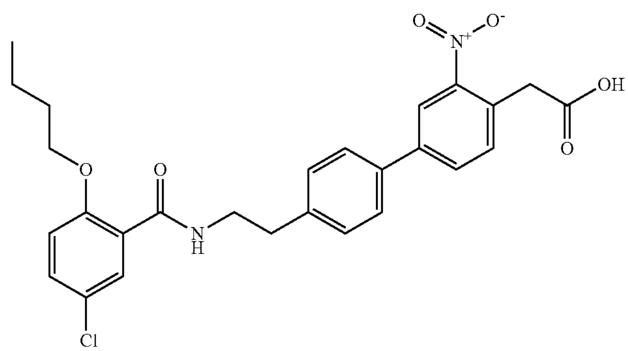 | (4'-{2-[(2-butoxy-5-chlorobenzoyl)amino]ethyl}-3-nitrobiphenyl-4-yl)acetic acid |
| 58. | 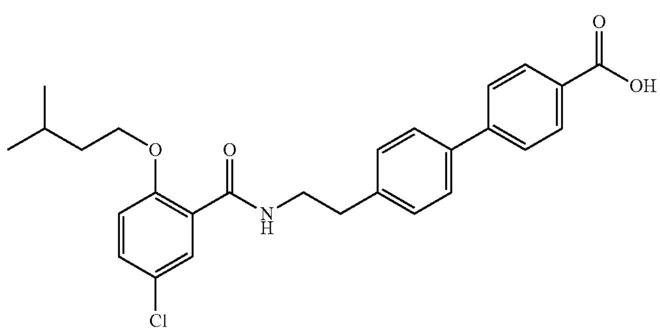 | 4'-(2-{[5-chloro-2-(3-methylbutoxy)benzoyl]amino}ethyl)biphenyl-4-carboxylic acid |
| 59. | 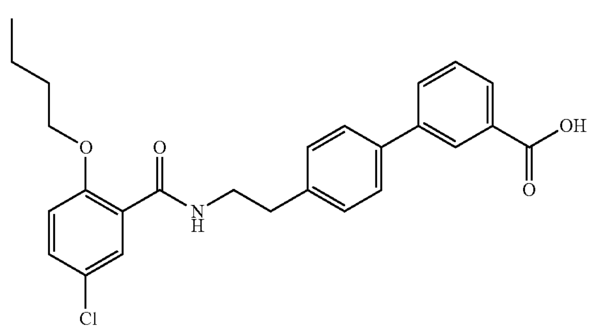 | 4'-{2-[(2-butoxy-5-chlorobenzoyl)amino]ethyl}biphenyl-3-carboxylic acid |

-continued

| | Structure | Name |
|---|---|---|
| 60. | 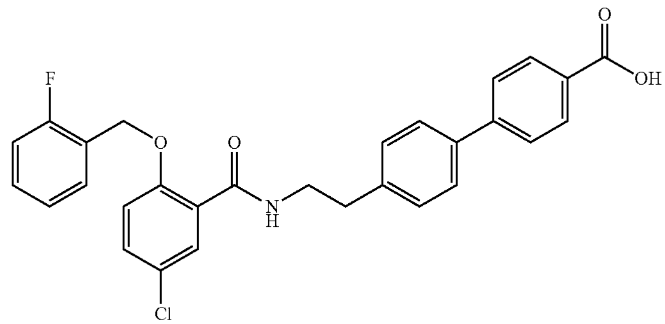 | 4'-[2-([5-chloro-2-[(2-fluorobenzyl)oxy]benzoyl}amino)ethyl]biphenyl-4-carboxylic acid |
| 61. | 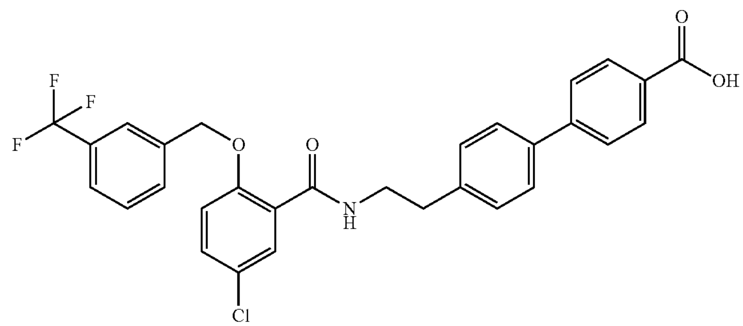 | 4'-{2-[(5-chloro-2-{[3-(trifluoromethyl)benzyl]oxy}benzoyl)amino]ethyl}biphenyl-4-carboxylic acid |
| 62. | 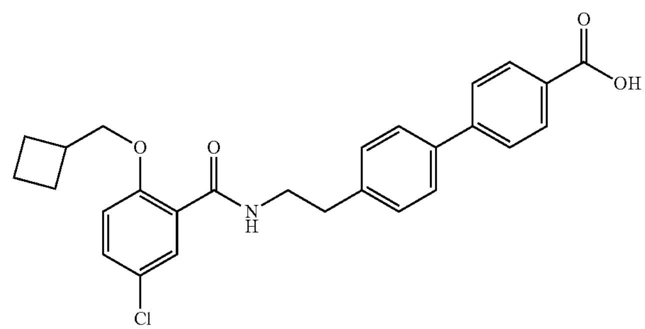 | 4'-(2-{[5-chloro-2-(cyclobutylmethoxy)benzoyl]amino}ethyl)biphenyl-4-carboxylic acid |
| 63. | 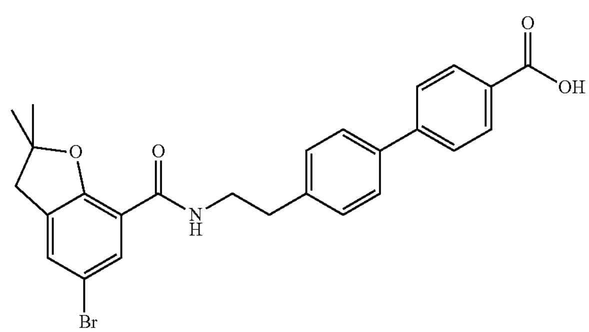 | 4'-(2-{[(5-bromo-2,2-dimethyl-2,3-dihydro-1-benzofuran-7-yl)carbonyl]amino}ethyl)biphenyl-4-carboxylic acid |
| 64. | 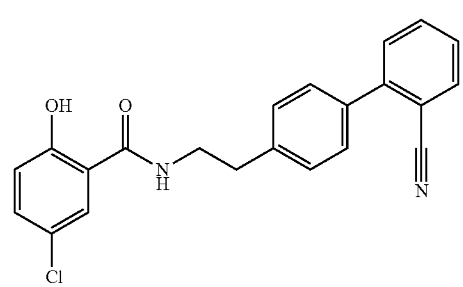 | 5-chloro-N-[2-(2'-cyanobiphenyl-4-yl)ethyl]-2-hydroxybenzamide |

-continued

| | Structure | Name |
|---|---|---|
| 65. | 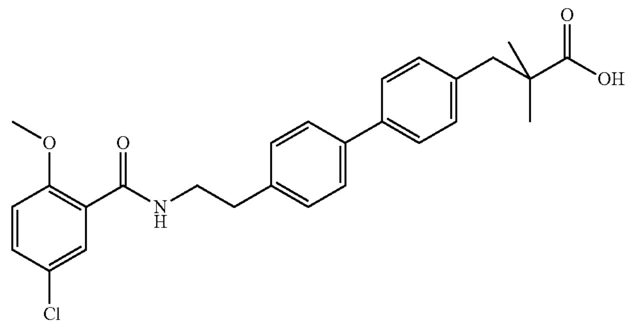 | 3-(4'-{2-[(5-chloro-2-methoxybenzoyl)amino]ethyl}biphenyl-4-yl)-2,2-dimethylpropanoic acid |
| 66. | 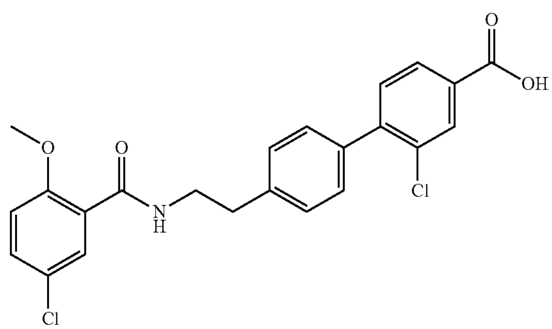 | 2-chloro-4'-{2-[(5-chloro-2-methoxybenzoyl)amino]ethyl}biphenyl-4-carboxylic acid |
| 67. | 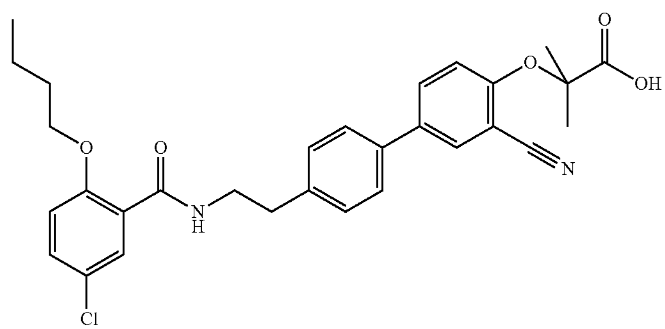 | 2-[(4'-{2-[(2-butoxy-5-chlorobenzoyl)amino]ethyl}-3-cyanobiphenyl-4-yl)oxy]-2-methylpropanoic acid |
| 68. | 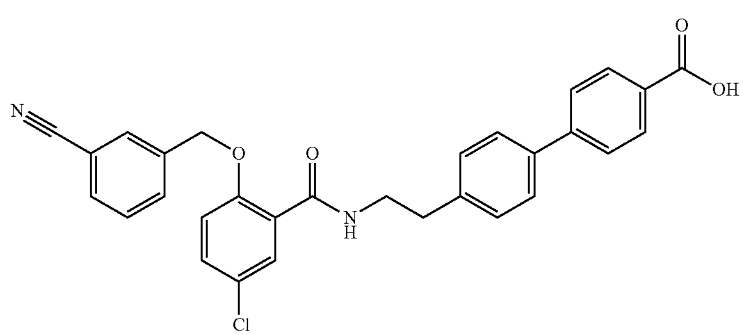 | 4'-[2-({5-chloro-2-[(3-cyanobenzyl)oxy]benzoyl}amino)ethyl]biphenyl-4-carboxylic acid |

| | Structure | Name |
|---|---|---|
| 69. | 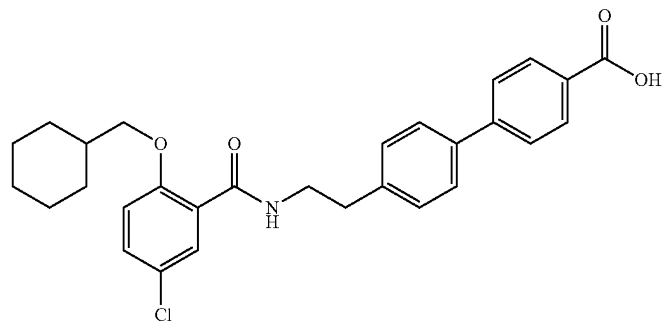 | 4'-(2-{[5-chloro-2-(cyclohexylmethoxy)benzoyl]amino}ethyl)biphenyl-4-carboxylic acid |
| 70. | 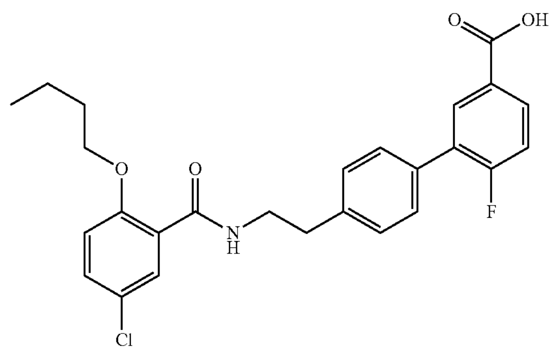 | 4'-{2-[(2-butoxy-5-chlorobenzoyl)amino]ethyl}-6-fluorobiphenyl-3-carboxylic acid |
| 71. | 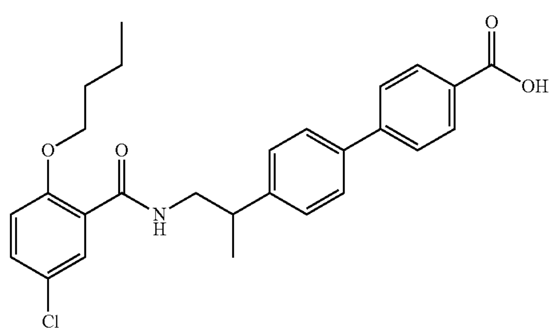 | 4'-{2-[(2-butoxy-5-chlorobenzoyl)amino]-1-methyl-ethyl}-biphenyl-4-carboxylic acid |
| 72. | 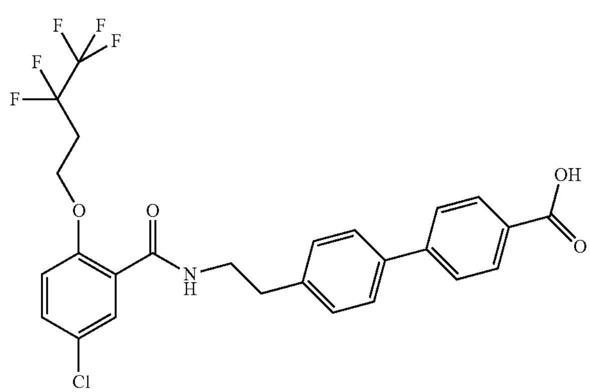 | 4'-(2-{[5-chloro-2-(3,3,4,4,4-pentafluorobutoxy)benzoyl]amino}ethyl)biphenyl-4-carboxylic acid |

| | Structure | Name |
|---|---|---|
| 73. | 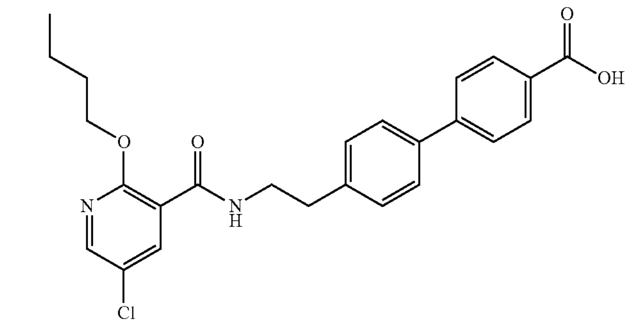 | 4'-(2-{[(2-butoxy-5-chloropyridin-3-yl)carbonyl]amino}ethyl)biphenyl-4-carboxylic acid |
| 74. | 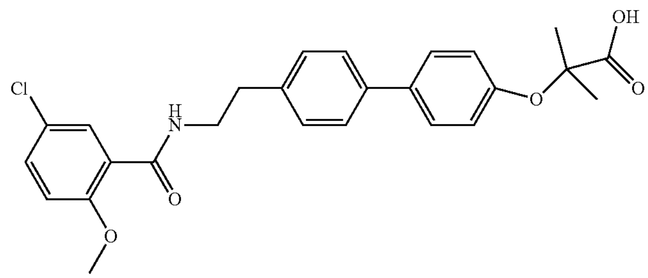 | 2-[(4'-{2-[(5-chloro-2-methoxybenzoyl)amino]ethyl}biphenyl-4-yl)oxy]-2-methylpropanoic acid |
| 75. | 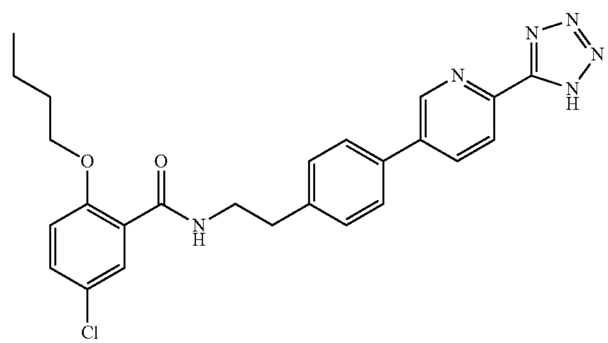 | 2-butoxy-5-chloro-N-(2-{4-[6-(1H-tetrazol-5-yl)pyridin-3-yl]phenyl}ethyl)benzamide |
| 76. | 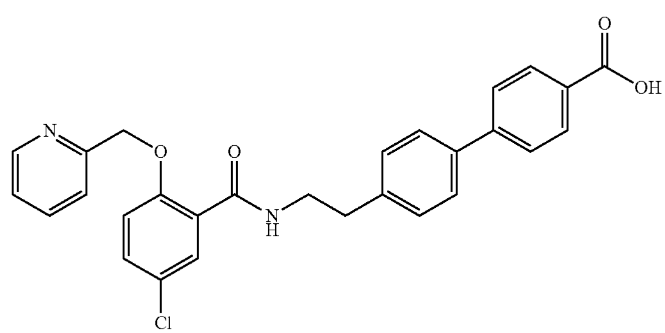 | 4'-(2-{[5-chloro-2-(pyridin-2-ylmethoxy)benzoyl]amino}ethyl)biphenyl-4-carboxylic acid |
| 77. | 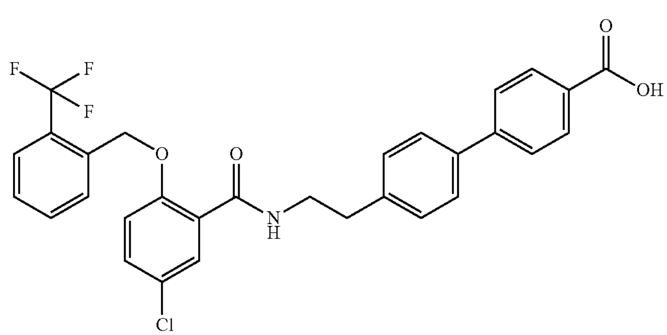 | 4'-{2-[(5-chloro-2-{[2-(trifluoromethyl)benzyl]oxy}benzoyl)amino]ethyl}biphenyl-4-carboxylic acid |

-continued

| | Structure | Name |
|---|---|---|
| 78. | 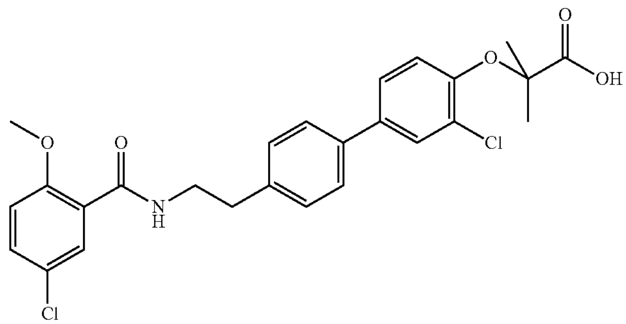 | 2-[(3-chloro-4'-{2-[(5-chloro-2-methoxybenzoyl)amino]ethyl}biphenyl-4-yl)oxy]-2-methylpropanoic acid |
| 79. | 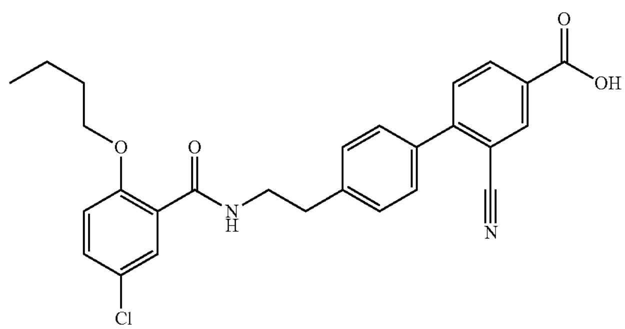 | 4'-{2-[(2-butoxy-5-chlorobenzoyl)amino]ethyl}-2-cyanobiphenyl-4-carboxylic acid |
| 80. | 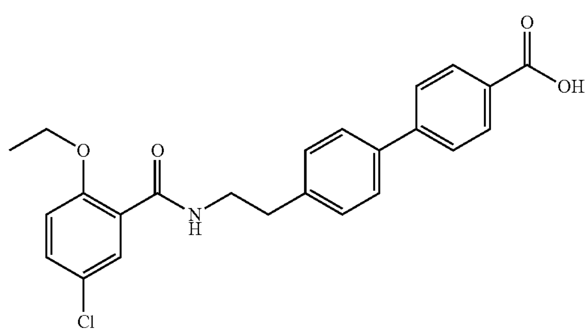 | 4'-{2-[(5-chloro-2-ethoxybenzoyl)amino]ethyl}biphenyl-4-carboxylic acid |
| 81. | 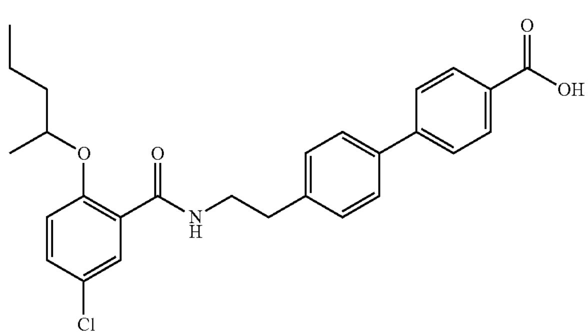 | 4'-(2-{[5-chloro-2-(1-methylbutoxy)benzoyl]amino}ethyl)biphenyl-4-carboxylic acid |

| | Structure | Name |
|---|---|---|
| 82. | 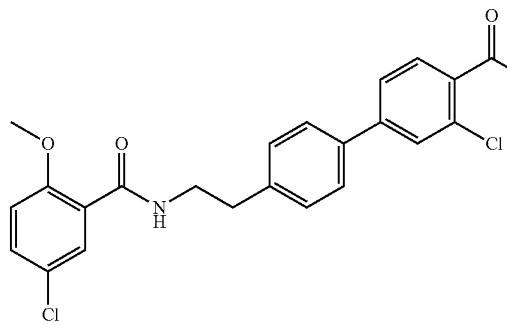 | 3-chloro-4'-{2-[(5-chloro-2-methoxybenzoyl)amino]ethyl}biphenyl-4-carboxylic acid |
| 83. | 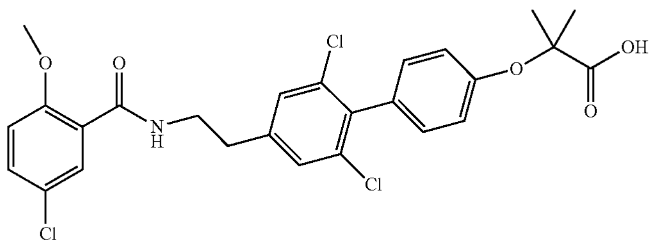 | 2-[(2',6'-dichloro-4'-{2-[(5-chloro-2-methoxybenzoyl)amino]ethyl}biphenyl-4-yl)oxy]-2-methylpropanoic acid |
| 84. | 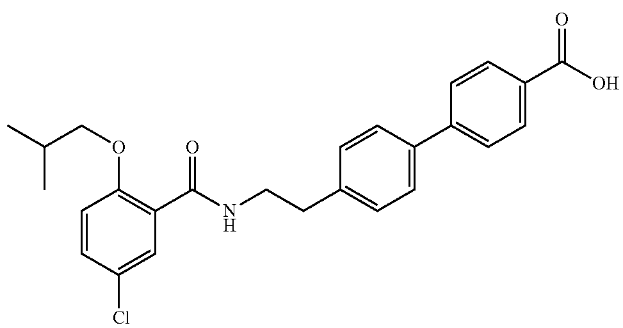 | 4'-{2-[(5-chloro-2-isobutoxybenzoyl)amino]ethyl}biphenyl-4-carboxylic acid |
| 85. | 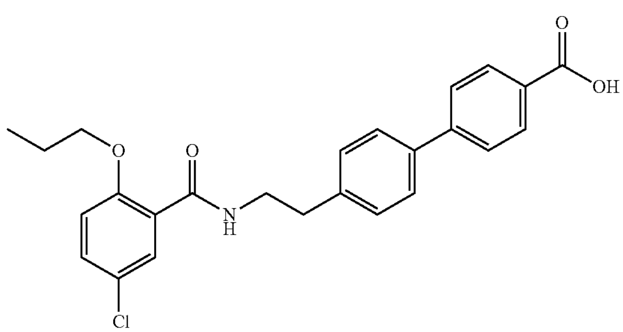 | 4'-{2-[(5-chloro-2-propoxybenzoyl)amino]ethyl}biphenyl-4-carboxylic acid |
| 86. | 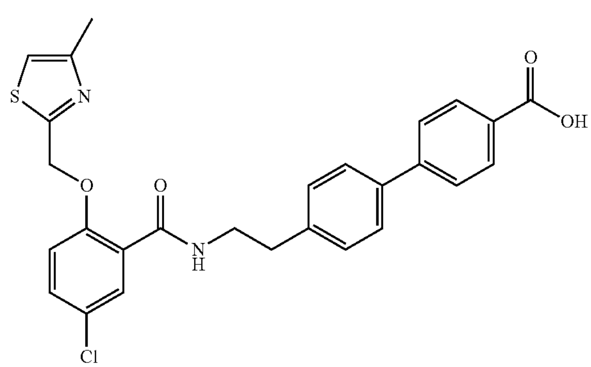 | 4'-[2-({5-chloro-2-[(4-methyl-1,3-thiazol-2-yl)methoxy]benzoyl}amino)ethyl]biphenyl-4-carboxylic acid |

-continued

| | Structure | Name |
|---|---|---|
| 87. | 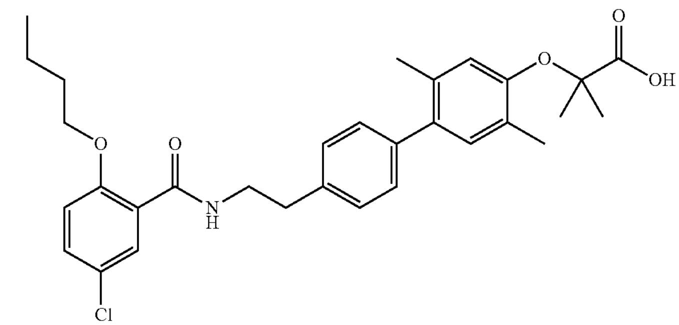 | 2-[(4'-{2-[(2-butoxy-5-chlorobenzoyl)amino]ethyl}-2,5-dimethylbiphenyl-4-yl)oxy]-2-methylpropanoic acid |
| 88. | 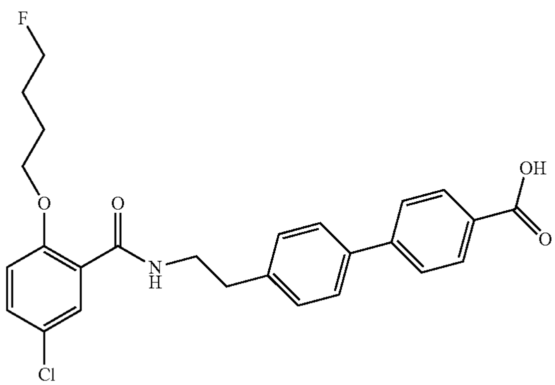 | 4'-(2-{[5-chloro-2-(4-fluorobutoxy)benzoyl]amino}ethyl)biphenyl-4-carboxylic acid |
| 89. | 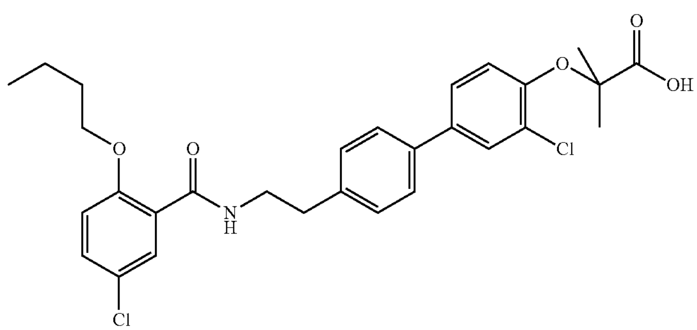 | 2-[(4'-{2-[(2-butoxy-5-chlorobenzoyl)amino]ethyl}-3-chlorobiphenyl-4-yl)oxy]-2-methylpropanoic acid |
| 90. | 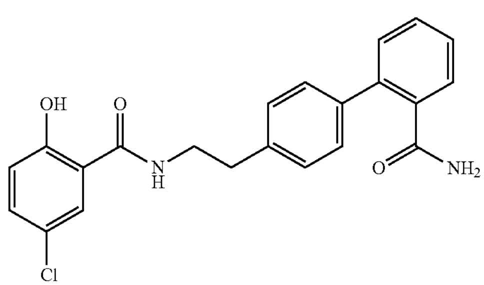 | 4'-{2-[(5-chloro-2-hydroxybenzoyl)amino]ethyl}biphenyl-2-carboxamide |
| 91. | 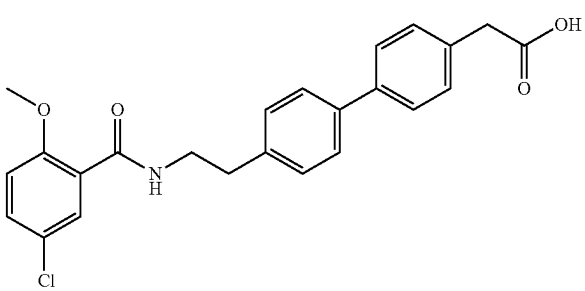 | (4'-{2-[(5-chloro-2-methoxybenzoyl)amino]ethyl}biphenyl-4-yl)acetic acid |

| | Structure | Name |
|---|---|---|
| 92. | 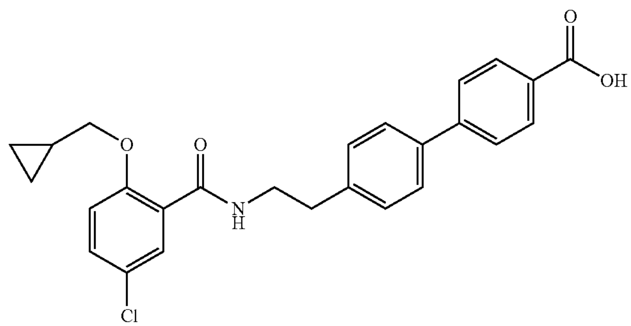 | 4'-(2-{[5-chloro-2-(cyclopropylmethoxy)benzoyl]amino}ethyl)biphenyl-4-carboxylic acid |
| 93. | 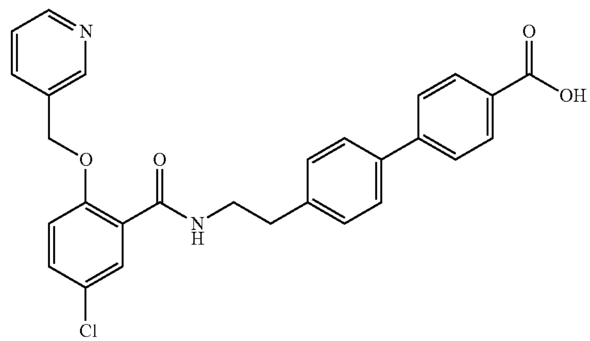 | 4'-(2-{[5-chloro-2-(pyridin-3-ylmethoxy)benzoyl]amino}ethyl)biphenyl-4-carboxylic acid |
| 94. | 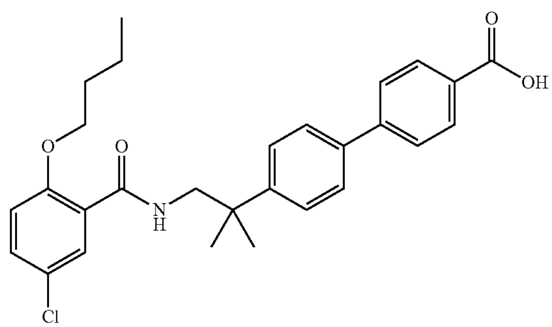 | 4'-{2-[(2-butoxy-5-chlorobenzoyl)amino]-1,1-dimethylethyl}biphenyl-4-carboxylic acid |
| 95. | 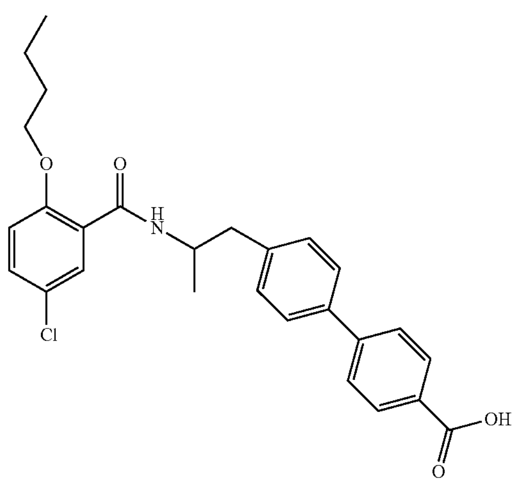 | 4'-{2-[(2-butoxy-5-chlorobenzoyl)amino]propyl}-biphenyl-4-carboxylic acid |

-continued

| | Structure | Name |
|---|---|---|
| 96. | 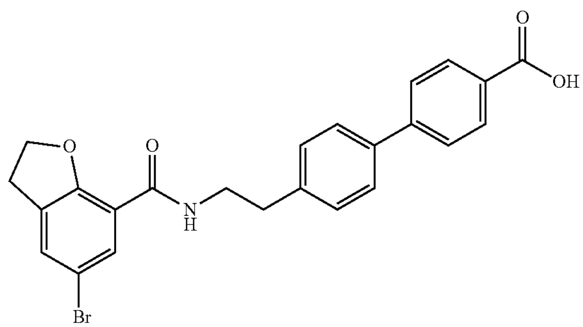 | 4'-(2-{[(5-bromo-2,3-dihydro-1-benzofuran-7-yl)carbonyl]amino}ethyl)biphenyl-4-carboxylic acid |
| 97. | 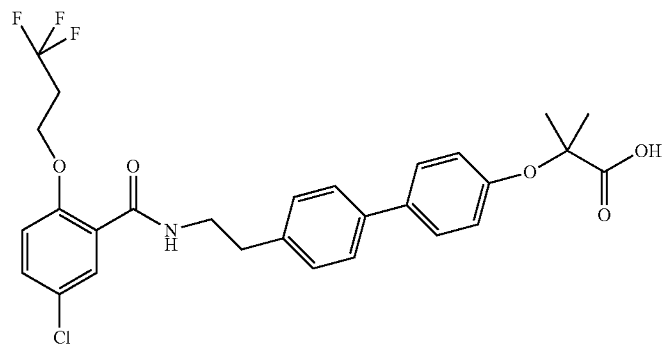 | 2-{[4'-(2-{[5-chloro-2-(3,3,3-trifluoropropoxy)benzoyl]amino}ethyl)biphenyl-4-yl]oxyl-2-methylpropanoic acid |
| 98. | 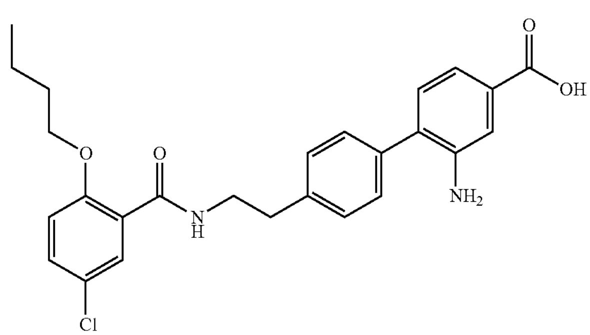 | 2-amino-4'-{2-[(2-butoxy-5-chlorobenzoyl)amino]ethyl}biphenyl-4-carboxylic acid |
| 99. | 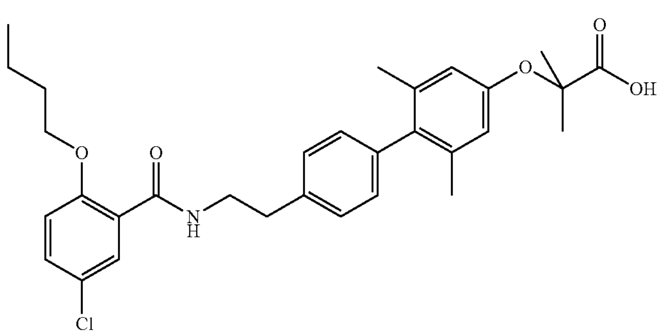 | 2-[(4'-{2-[(2-butoxy-5-chlorobenzoyl)amino]ethyl}-2,6-dimethylbiphenyl-4-yl)oxy]-2-methylpropanoic acid |

-continued

| | Structure | Name |
|---|---|---|
| 100. | 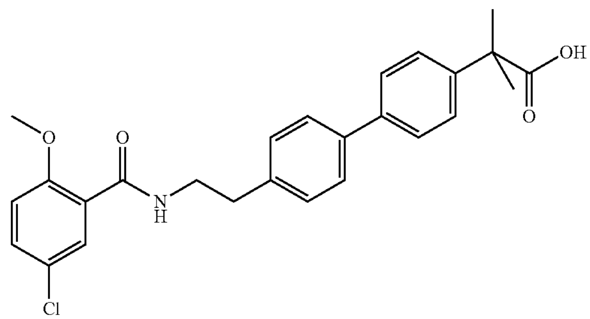 | 2-(4'-{2-[(5-chloro-2-methoxybenzoyl)amino]ethyl}biphenyl-4-yl)-2-methylpropanoic acid |
| 101. | 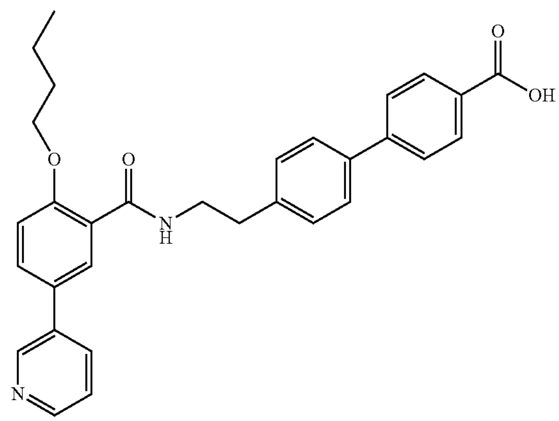 | 4'-{2-[(2-butoxy-5-pyridin-3-ylbenzoyl)amino]ethyl}biphenyl-4-carboxylic acid |
| 102. | 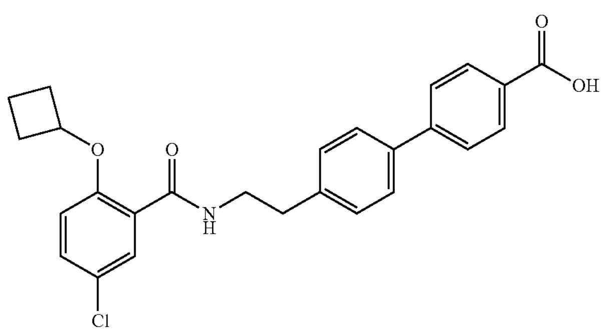 | 4'-(2-{[5-chloro-2-(cyclobutyloxy)benzoyl]amino}ethyl)-biphenyl-4-carboxylic acid |
| 103. | 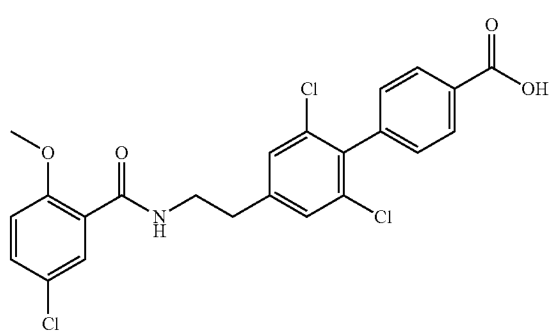 | 2',6'-dichloro-4'-{2-[(5-chloro-2-methoxybenzoyl)amino]ethyl}biphenyl-4-carboxylic acid |

-continued

| | Structure | Name |
|---|---|---|
| 104. | 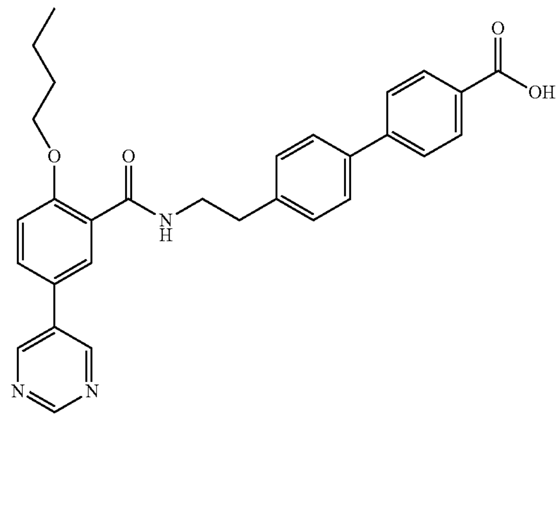 | 4'-{2-[(2-butoxy-5-pyrimidin-5-ylbenzoyl)amino]ethyl}biphenyl-4-carboxylic acid |
| 105. | 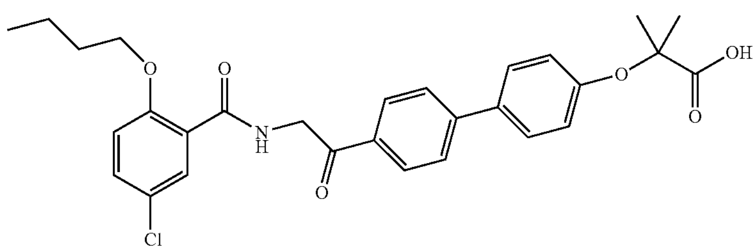 | 2-({4'-[N-(2-butoxy-5-chlorobenzoyl)glycyl]biphenyl-4-yl}oxy)-2-methylpropanoic acid |
| 106. | 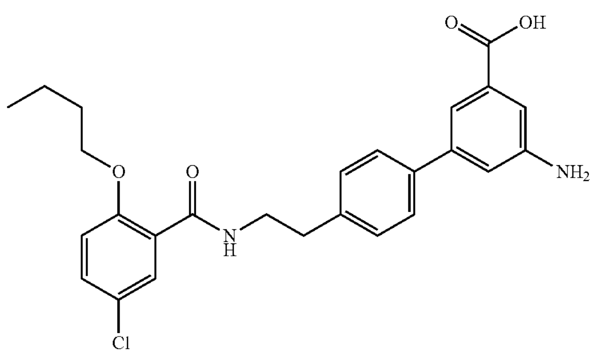 | 5-amino-4'-{2-[(2-butoxy-5-chlorobenzoyl)amino]ethyl}biphenyl-3-carboxylic acid |
| 107. | 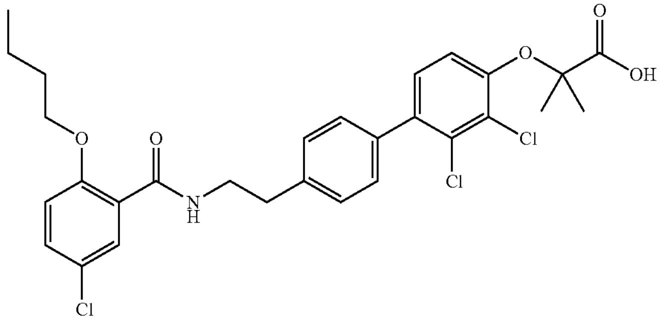 | 2-[(4'-{2-[(2-butoxy-5-chlorobenzoyl)amino]ethyl}-2,3-dichlorobiphenyl-4-yl)oxyl-2-methylpropanoic acid |

-continued
| | Structure | Name |
|---|---|---|
| 108. | 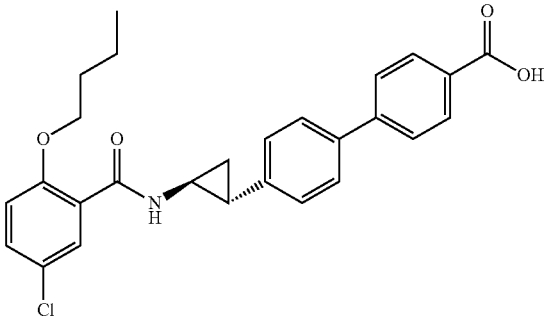 | 4'-{(1R,2S)-2-[(2-butoxy-5-chlorobenzoyl)amino]cyclopropyl}-biphenyl-4-carboxylic acid |
| 109. | 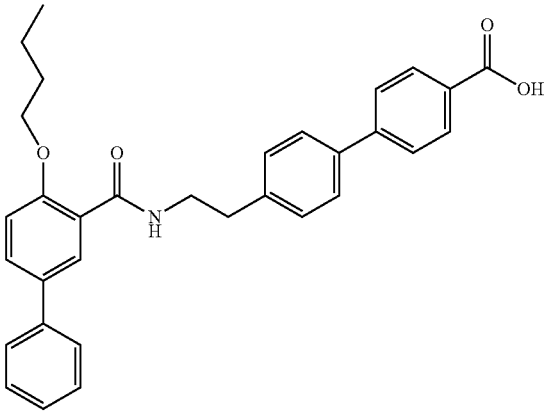 | 4'-(2-{[(4-butoxybiphenyl-3-yl)carbonyl]amino}ethyl)biphenyl-4-carboxylic acid |
| 110. | 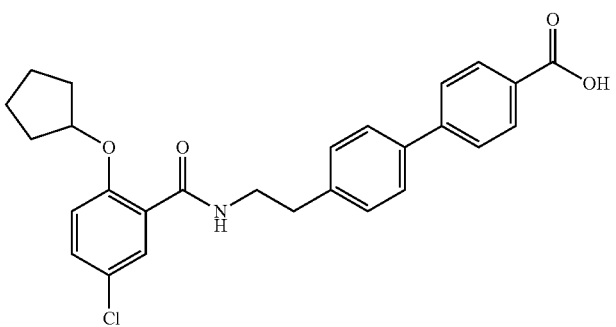 | 4'-(2-{[5-chloro-2-(cyclopentyloxy)benzoyl]amino}ethyl)biphenyl-4-carboxylic acid |
| 111. | 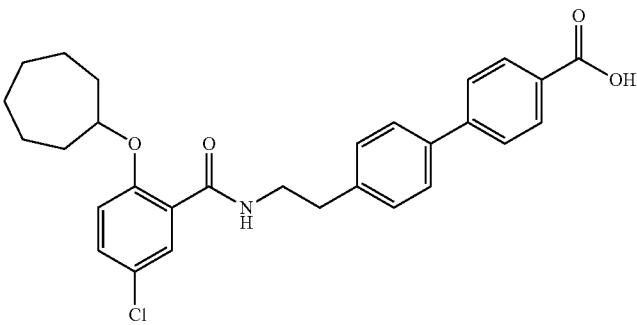 | 4'-(2-{[5-chloro-2-(cycloheptyloxy)benzoyl]amino}ethyl)biphenyl-4-carboxylic acid |

-continued
| | Structure | Name |
|---|---|---|
| 112. | 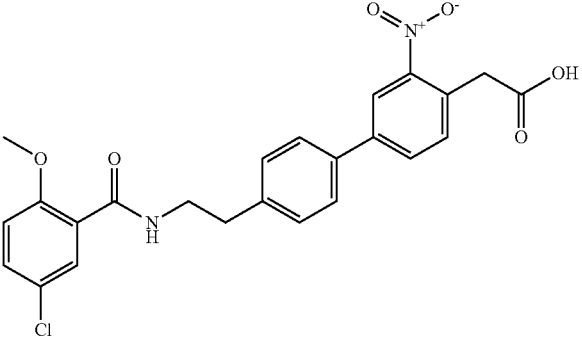 | (4'-{2-[(5-chloro-2-methoxybenzoyl)amino]ethyl}-3-nitrobiphenyl-4-yl)acetic acid |
| 113. | 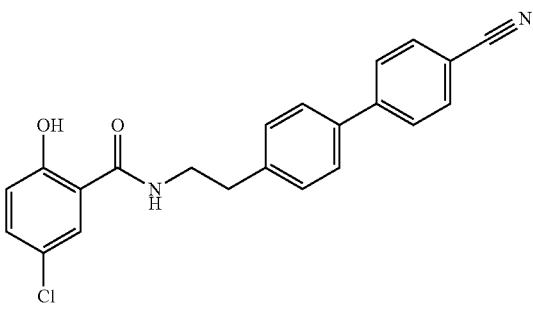 | 5-chloro-N-[2-(4'-cyanobiphenyl-4-yl)ethyl]-2-hydroxybenzamide |
| 114. | 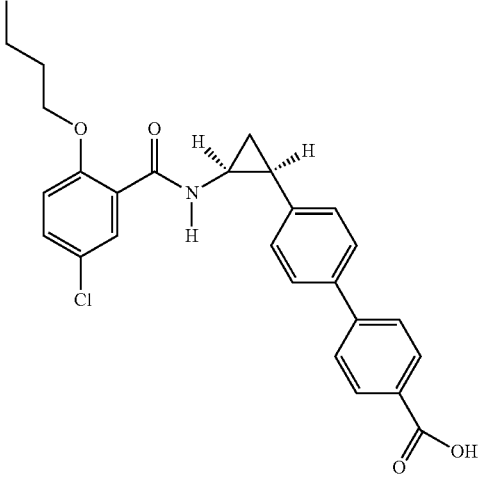 | 4'-{(1S,2S)-2-[(2-butoxy-5-chlorobenzoyl)amino]cyclopropyl}-biphenyl-4-carboxylic acid |
| 115. | 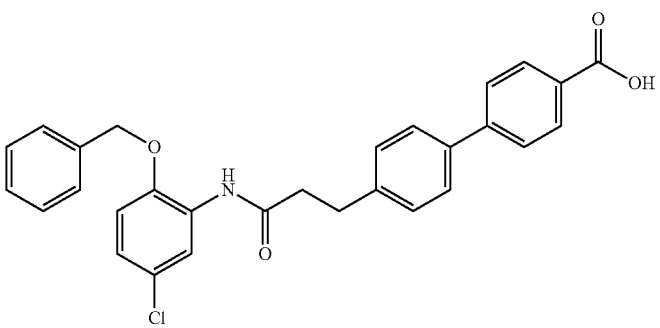 | 4'-(3-{[2-(benzyloxy)-5-chlorophenyl]amino}-3-oxopropyl)biphenyl-4-carboxylic acid |

-continued

| | Structure | Name |
|---|---|---|
| 116. | 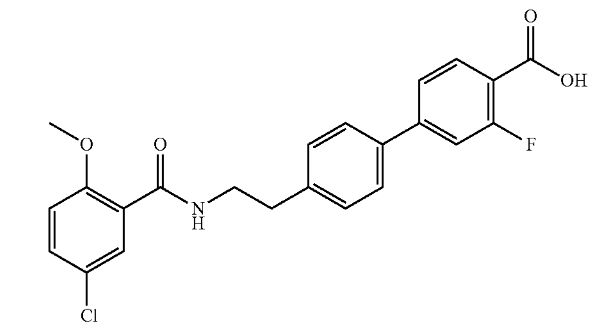 | 4'-{2-[(5-chloro-2-methoxybenzoyl)amino]ethyl}-3-fluorobiphenyl-4-carboxylic acid |
| 117. | 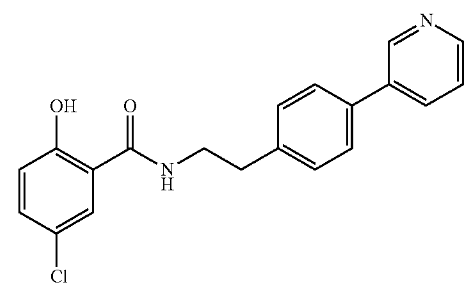 | 5-chloro-2-hydroxy-N-[2-(4-pyridin-3-ylphenyl)ethyl]benzamide |
| 118. | 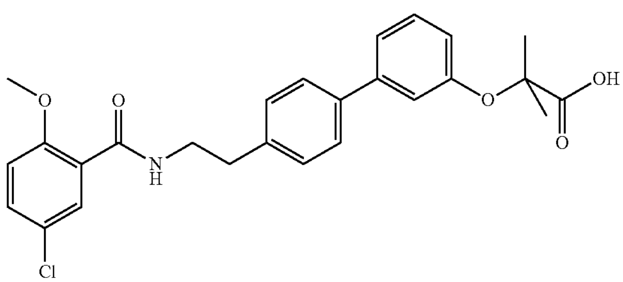 | 2-[(4'-{2-[(5-chloro-2-methoxybenzoyl)amino]ethyl}biphenyl-3-yl)oxy]-2-methylpropanoic acid |
| 119. | 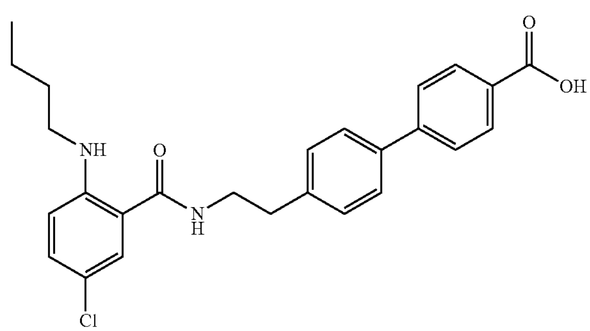 | 4'-(2-{[2-(butylamino)-5-chlorobenzoyl]amino}ethyl)biphenyl-4-carboxylic acid |

-continued
| | Structure | Name |
|---|---|---|
| 120. | 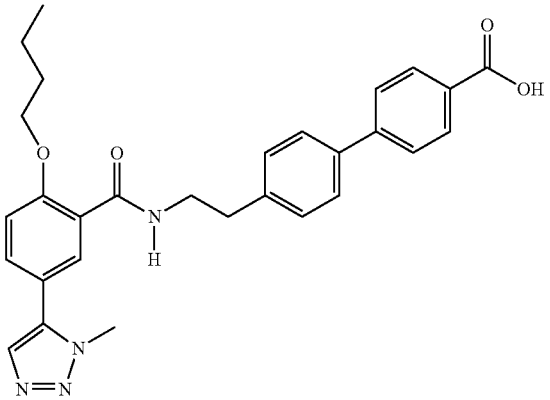 | 4'-(2-{[2-butoxy-5-(1-methyl-1H-1,2,3-triazol-5-yl)benzoyl]amino}ethyl)biphenyl-4-carboxylic acid |
| 121. | 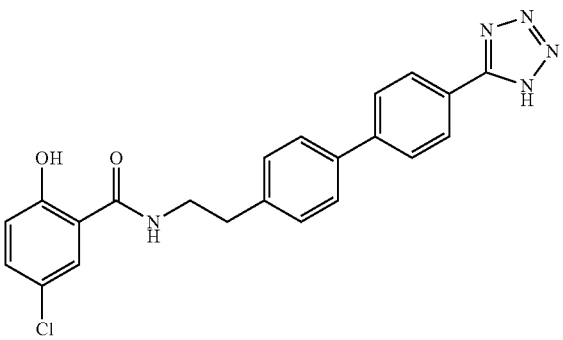 | 5-chloro-2-hydroxy-N-{2-[4'-(1H-tetrazol-5-yl)biphenyl-4-yl]ethyl}benzamide |
| 122. | 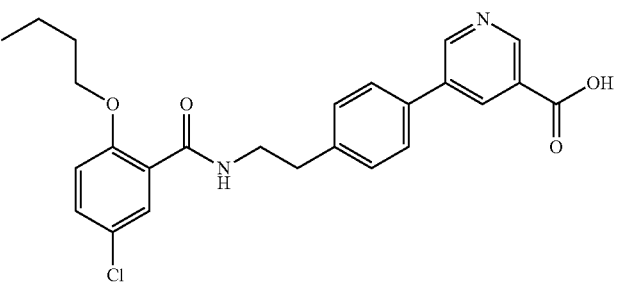 | 5-(4-{2-[(2-butoxy-5-chlorobenzoyl)amino]ethyl}phenyl)-nicotinic acid |
| 123. | 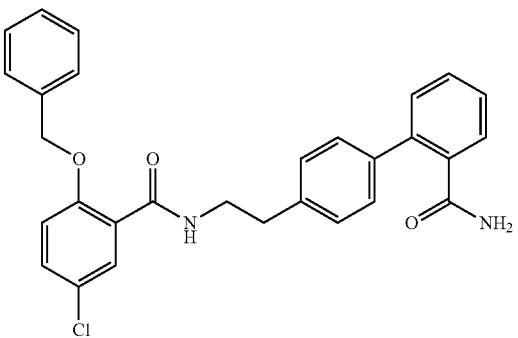 | 4'-(2-{[2-(benzyloxy)-5-chlorobenzoyl]amino}ethyl)biphenyl-2-carboxamide |

-continued

| | Structure | Name |
|---|---|---|
| 124. | 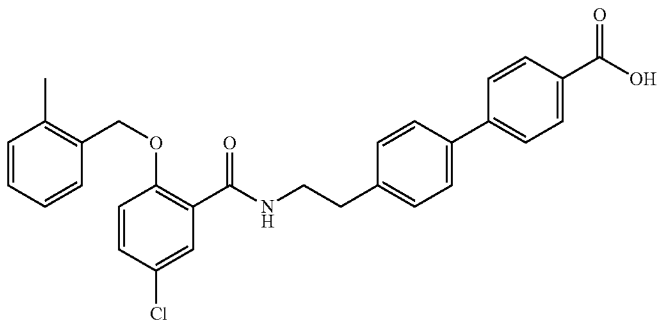 | 4'-[2-({5-chloro-2-[(2-methylbenzyl)oxy]benzoyl}amino)-ethyl]biphenyl-4-carboxylic acid |
| 125. | 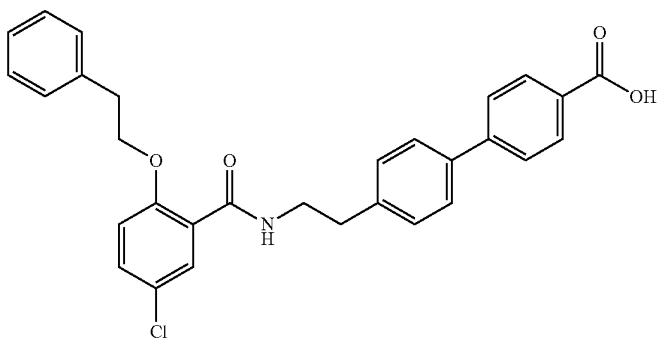 | 4'-(2-{[5-chloro-2-(2-phenylethoxy)benzoyl]amino}ethyl)-biphenyl-4-carboxylic acid |
| 126. | 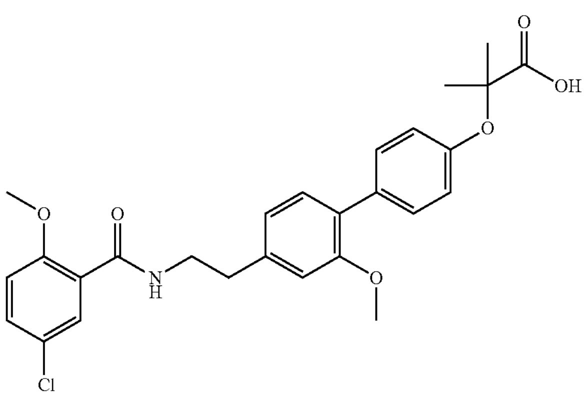 | 2-[(4'-{2-[(5-chloro-2-methoxybenzoyl)amino]ethyl}-2'-methoxybiphenyl-4-yl)oxy]-2-methylpropanoic acid |
| 127. | 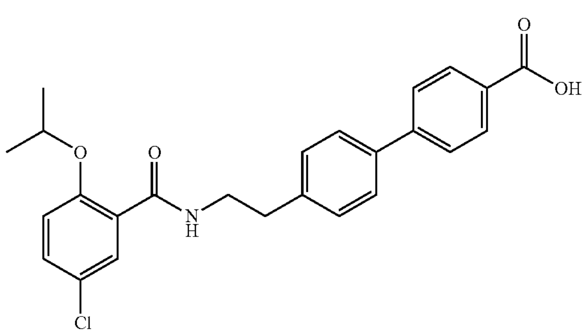 | 4'-{2-[(5-chloro-2-isopropoxybenzoyl)amino]ethyl}-biphenyl-4-carboxylic acid |

-continued

| | Structure | Name |
|---|---|---|
| 128. | 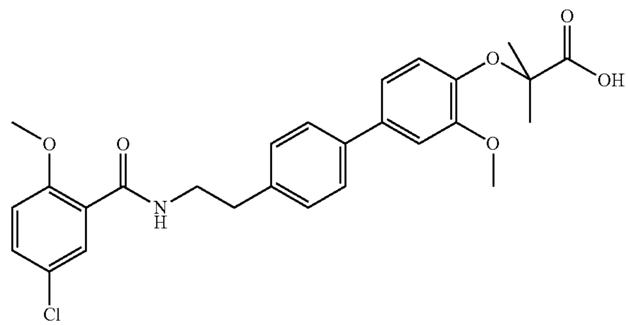 | 2-[(4'-{2-[(5-chloro-2-methoxybenzoyl)amino]ethyl}-3-methoxybiphenyl-4-yl)oxy]-2-methylpropanoic acid |
| 129. | 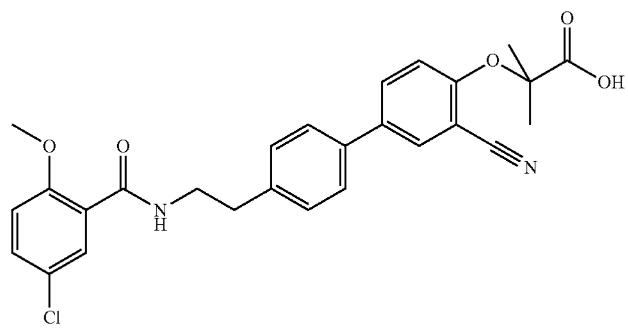 | 2-[(4'-{2-[(5-chloro-2-methoxybenzoyl)amino]ethyl}-3-cyanobiphenyl-4-yl)oxy]-2-methylpropanoic acid |
| 130. | 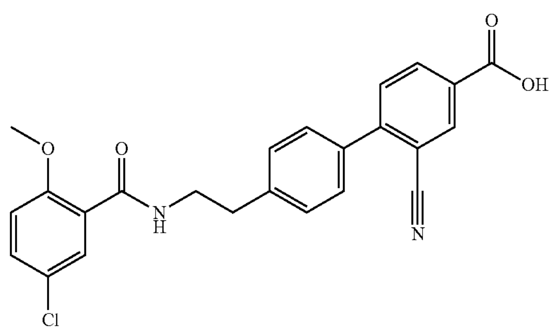 | 4'-{2-[(5-chloro-2-methoxybenzoyl)amino]ethyl}-2-cyanobiphenyl-4-carboxylic acid |
| 131. | 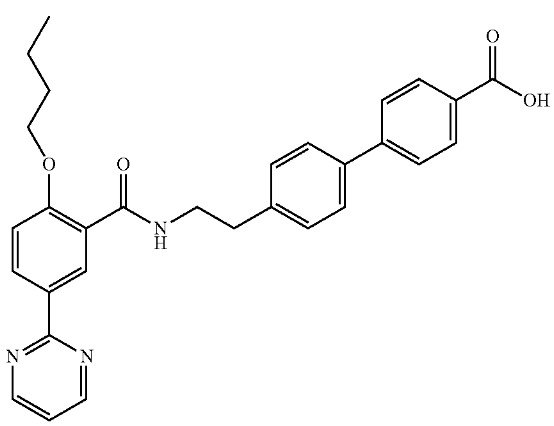 | 4'-{2-[(2-butoxy-5-pyrimidin-2-ylbenzoyl)amino]ethyl}biphenyl-4-carboxylic acid |

-continued

| | Structure | Name |
|---|---|---|
| 132. | 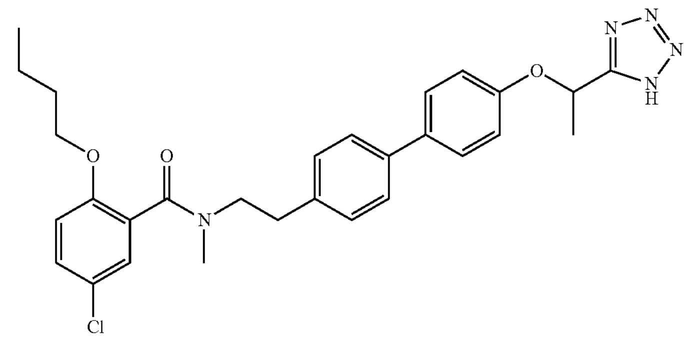 | 2-butoxy-5-chloro-N-methyl-N-(2-{4'-[1-(1H-tetrazol-5-yl)ethoxy[biphenyl-4-yl}ethyl)benzamide |
| 133. | 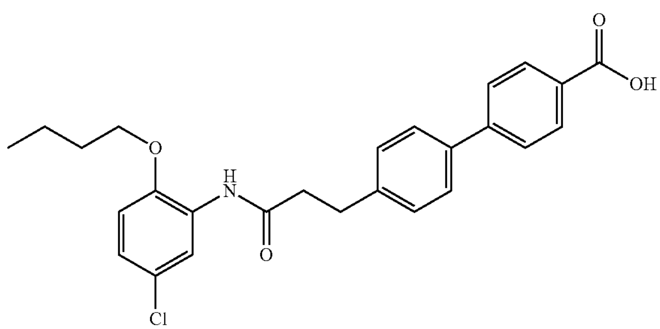 | 4'-{3-[(2-butoxy-5-chlorophenyl)amino]-3-oxopropyl}biphenyl-4-carboxylic cid |
| 134. | 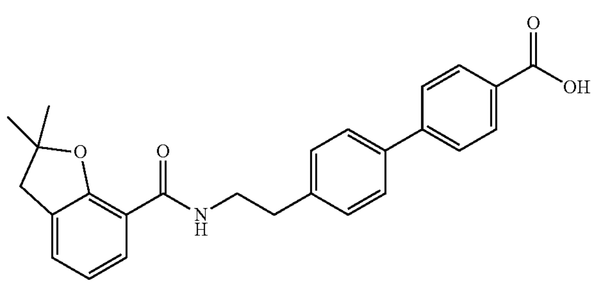 | 4'-(2-{[(2,2-dimethyl-2,3-dihydro-1-benzofuran-7-yl)carbonyl]amino}ethyl)biphenyl-4-carboxylic acid |
| 135. | 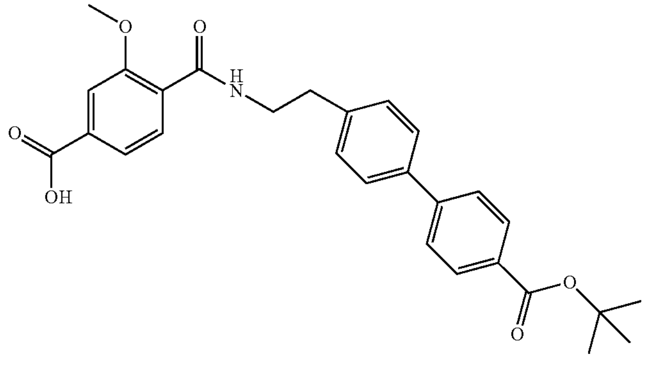 | 4-({2-[4'-(tert-butoxycarbonyl)biphenyl-4-yl]ethyl}carbamoyl)-3-methoxybenzoic acid |

-continued

| | Structure | Name |
|---|---|---|
| 136. | 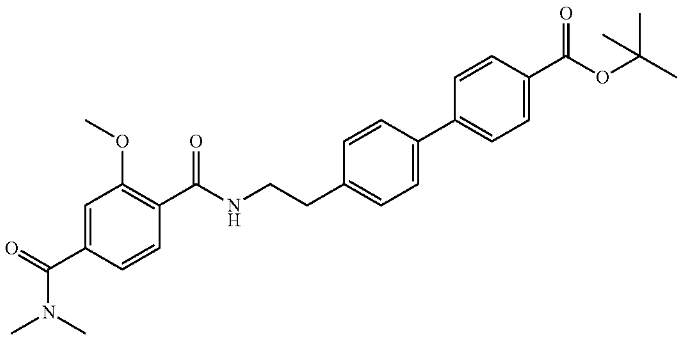 | tert-butyl 4'-(2-{[4-(dimethylcarbamoyl)-2-methoxybenzoyl]amino}ethyl)-biphenyl-4-carboxylate |
| 137. | 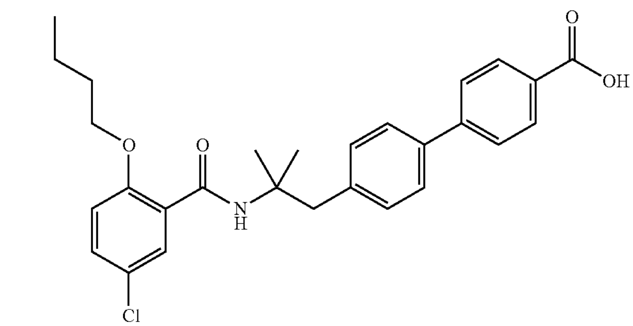 | 4'-{2-[(2-butoxy-5-chloro-benzoyl)amino]-2-methyl-propyl}biphenyl-4-carboxylic acid |
| 138. | 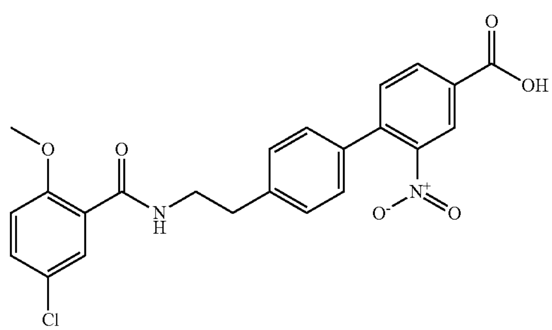 | 4'-{2-[(5-chloro-2-methoxybenzoyl)amino]ethyl}-2-nitrobiphenyl-4-carboxylic acid |
| 139. | 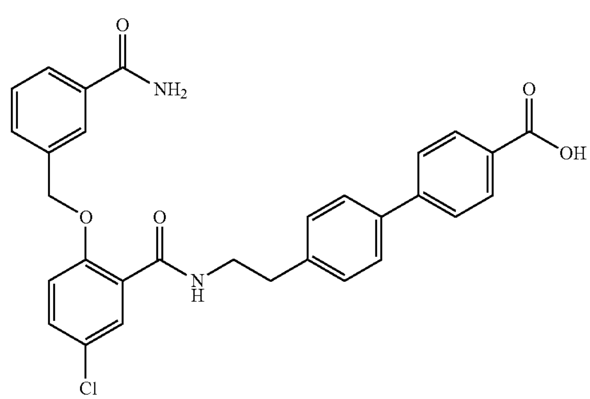 | 4'-[2-({2-[(3-carbamoylbenzyl)oxy]-5-chlorobenzoyl}amino]ethyl]biphenyl-4-carboxylic acid |

-continued

| | Structure | Name |
|---|---|---|
| 140. | 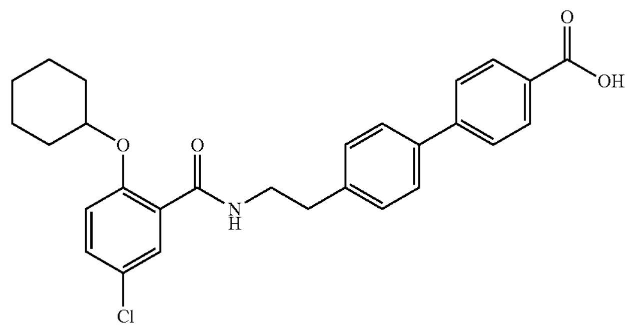 | 4'-(2-{[5-chloro-2-(cyclohexyloxy)benzoyl]amino}ethyl)-biphenyl-4-carboxylic acid |
| 141. | 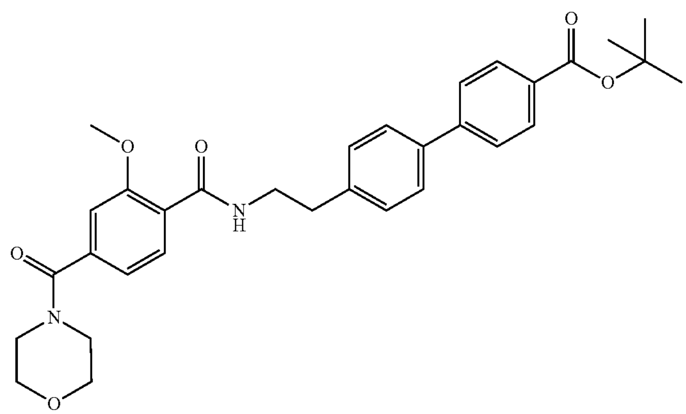 | tert-butyl 4'-(2-{[2-methoxy-4-(morpholin-4-ylcarbonyl)benzoyl]amino}ethyl)-biphenyl-4-carboxylate |
| 142. | 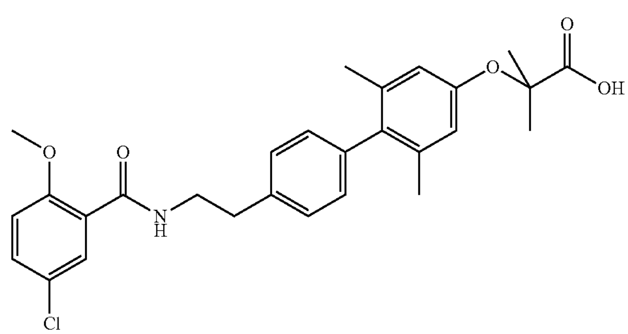 | 2-(4'-{2-[(5-chloro-2-methoxybenzoyl)amino]ethyl}-2,6-dimethylbiphenyl-4-yl)oxy]-2-methylpropanoic acid |
| 143. | 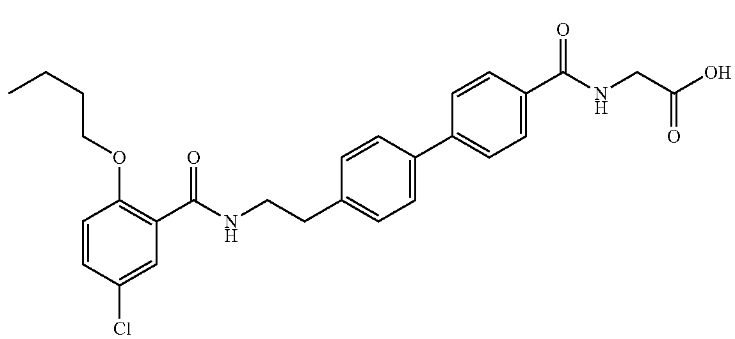 | N-[(4'-{2-[(2-butoxy-5-chlorobenzoyl)amino]ethyl}biphenyl-4-yl)carbonyl]glycine |

-continued

| | Structure | Name |
|---|---|---|
| 144. | 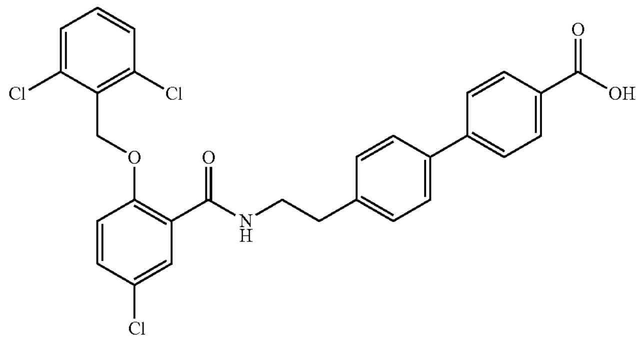 | 4'-[2-({5-chloro-2-[(2,6-dichlorobenzyl)oxy]benzoyl}amino)-ethyl]biphenyl-4-carboxylic acid |
| 145. | 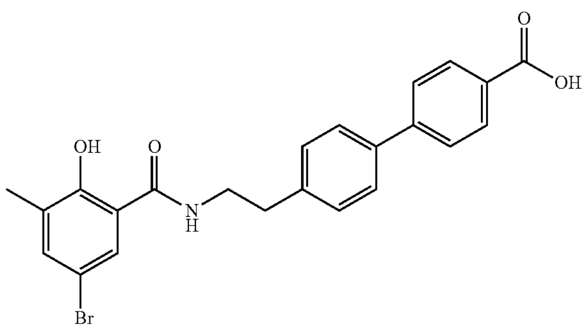 | 4'-{2-[(5-bromo-2-hydroxy-3-methylbenzoyl)amino]ethyl}biphenyl-4-carboxylic acid |
| 146. | 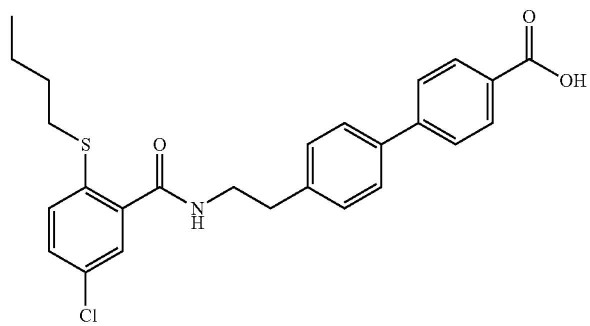 | 4'-(2-{[2-(butylthio)-5-chlorobenzoyl]amino}ethyl)biphenyl-4-carboxylic acid |
| 147. | 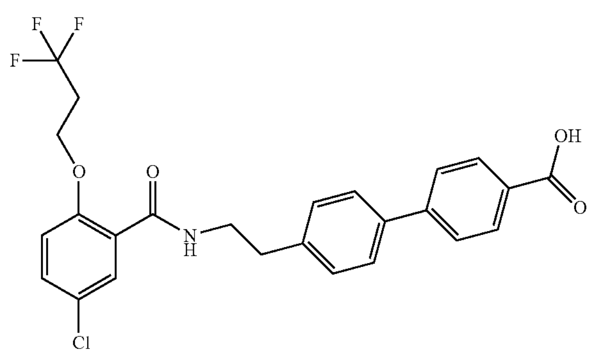 | 4'-(2-{[5-chloro-2-(3,3,3-trifluoropropoxy)benzoyl]amino}ethyl)biphenyl-4-carboxylic acid |

-continued

| | Structure | Name |
|---|---|---|
| 148. | 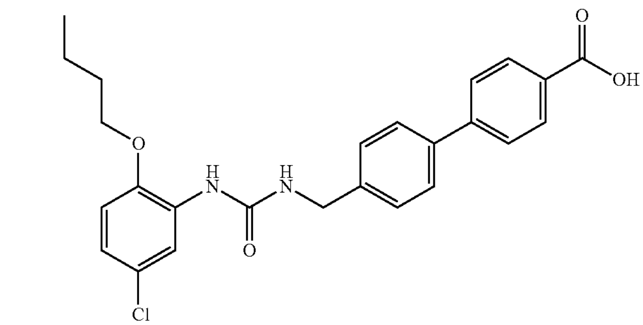 | 4'-({[(2-butoxy-5-chlorophenyl)carbamoyl]amino}methyl)biphenyl-4-carboxylic acid |
| 149. | 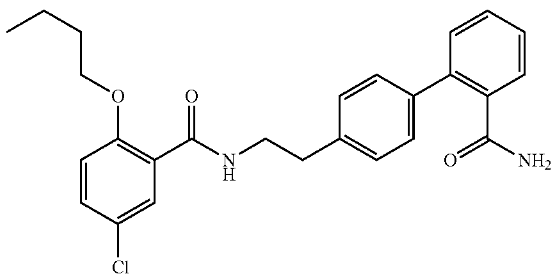 | 4'-{2-[(2-butoxy-5-chlorobenzoyl)amino]ethyl}biphenyl-2-carboxamide |
| 150. | 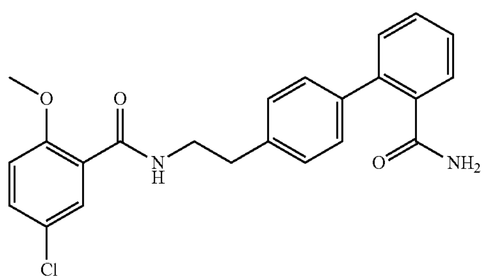 | 4'-{2-[(5-chloro-2-methoxybenzoyl)amino]ethyl}biphenyl-2-carboxamide |
| 151. | 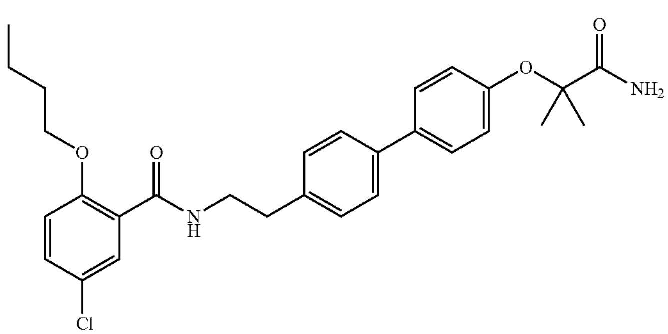 | N-{2-[4'-(2-amino-1,1-dimethyl-2-oxoethoxy)biphenyl-4-yl]ethyl}-2-butoxy-5-chlorobenzamide |
| 152. | 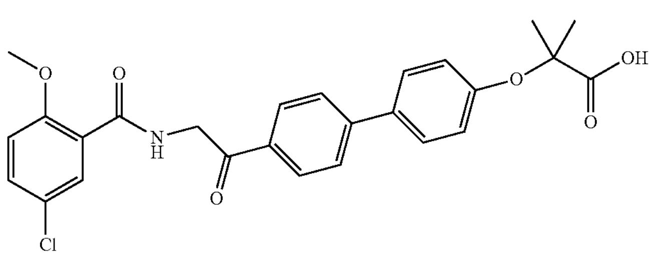 | 2-({4'-[N-(5-chloro-2-methoxybenzoyl)glycyl]biphenyl-4-yl}oxy)-2-methylpropanoic acid |

-continued

| | Structure | Name |
|---|---|---|
| 153. | 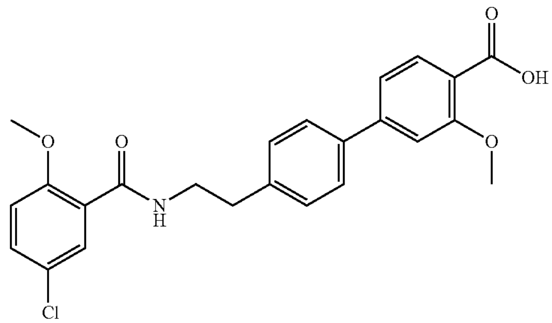 | 4'-{2-[(5-chloro-2-methoxybenzoyl)amino]ethyl}-3-methoxybiphenyl-4-carboxylic acid |
| 154. | 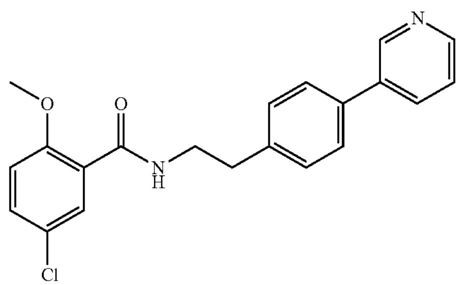 | 5-chloro-2-methoxy-N-[2-(4-pyridin-3-ylphenyl)ethyl]benzamide |
| 155. | 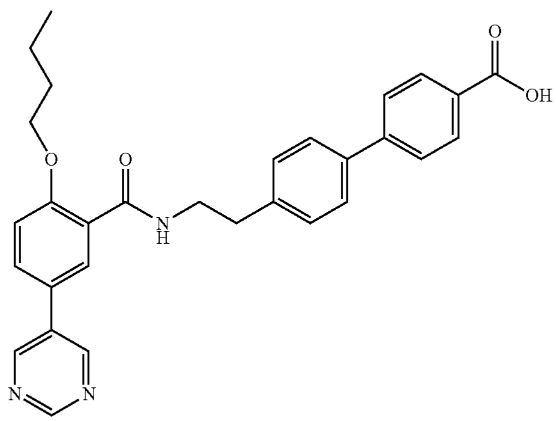 | 4'-[2-(2-Butoxy-5-pyrimidin-5-yl-benzoylamino)-ethyl]-biphenyl-4-carboxylic acid |
| 156. | 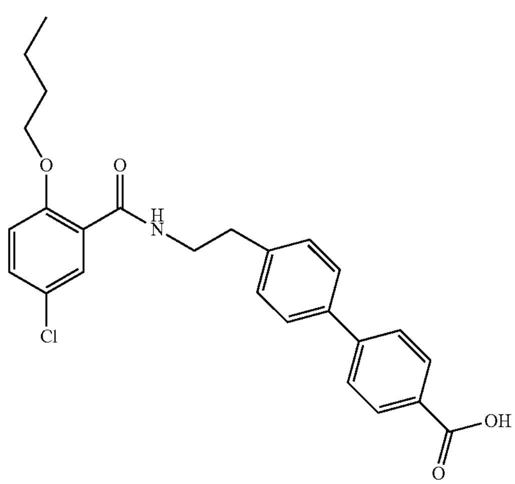 | 4'-{2-[(2-butoxy-5-chloro-benzoyl)amino]ethyl}biphenyl-4-carboxylic acid |

-continued

| | Structure | Name |
|---|---|---|
| 157. | 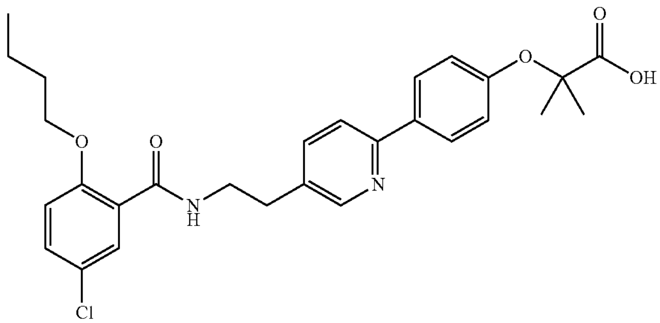 | 2-(4-{5-[2-(2-butoxy-5-chloro-benzoylamino)-ethyl]-pyridin-2-yl}-phenoxy)-2-methyl-propionic acid |
| 158. | 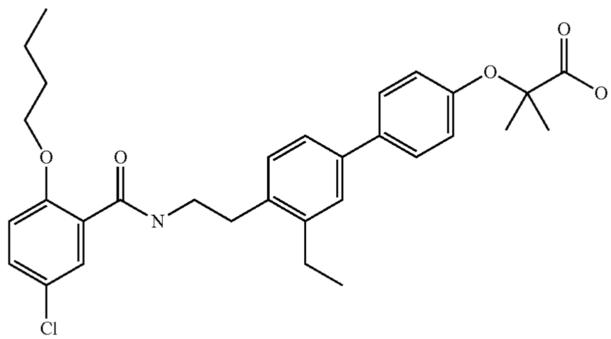 | 2-{4'-[2-(2-butoxy-5-chloro-benzoylamino)-ethyl]-3'-ethyl-biphenyl-4-yloxy}-2-methyl-propionic acid |
| 159. | 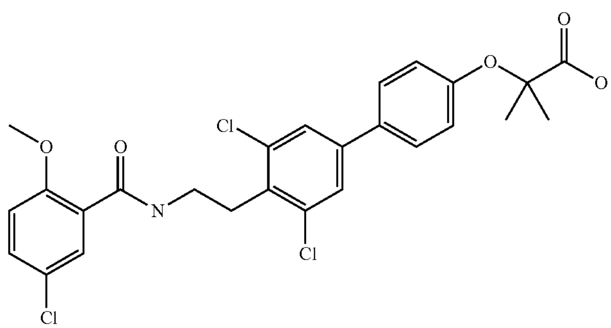 | 2-{3',5'-Dichloro-4'-[2-(5-chloro-2-methoxy-benzoylamino)-ethyl]-biphenyl-4-yloxy}-2-methyl-propionic acid |

In an additional embodiment of the invention there are provided compounds of the formula (I) selected from the group below or a tautomer thereof or a salt thereof:
(4'-{2-[(2-butoxy-5-chlorobenzoyl)amino]ethyl}biphenyl-4-yl)acetic acid;
2-[(4'-{2-[(2-butoxy-5-chlorobenzoyl)amino]ethyl}-2,5-difluorobiphenyl-4-yl)oxy]-2-methylpropanoic acid;
4'-{2-[(2-butoxy-5-chlorobenzoyl)amino]ethyl}-3-chlorobiphenyl-4-carboxylic acid;
2-[(4'-{2-[(2-butoxy-5-chlorobenzoyl)amino]ethyl}-3-fluorobiphenyl-4-yl)oxy]-2-methylpropanoic acid;
2-[(4'-{2-[(5-chloro-2-methoxybenzoyl)amino]ethyl}-2,3-dimethylbiphenyl-4-yl)oxy]-2-methylpropanoic acid;
2-[(4'-{2-[(2-butoxy-5-chlorobenzoyl)amino]ethyl}biphenyl-4-yl)oxy]-2-methylpropanoic acid;
4'-{2-[(2-butoxy-5-chlorobenzoyl)amino]ethyl}-2-nitrobiphenyl-4-carboxylic acid;
2-{[4'-(2-{[2-(benzyloxy)-5-chlorobenzoyl]amino}ethyl)biphenyl-4-yl]oxy}-2-methylpropanoic acid;
2-(benzyloxy)-5-chloro-N-{2-[4'-(1H-tetrazol-5-yl)biphenyl-4-yl]ethyl}benzamide;
2-[(4'-{2-[(5-chloro-2-methoxybenzoyl)amino]ethyl}-2,5-difluorobiphenyl-4-yl)oxy]-2-methylpropanoic acid;
4'-{2-[(2-butoxy-5-chlorobenzoyl)amino]ethyl}-2-chlorobiphenyl-4-carboxylic acid;
2-[(4'-{2-[(5-chloro-2-propoxybenzoyl)amino]ethyl}biphenyl-4-yl)oxy]-2-methylpropanoic acid;
4'-[2-({5-chloro-2-[(3-fluorobenzyl)oxy]benzoyl}amino)ethyl]biphenyl-4-carboxylic acid;
4'-[2-({5-chloro-2-[(3-methoxybenzyl)oxy]benzoyl}amino)ethyl]biphenyl-4-carboxylic acid;
2-[(4'-{2-[(2-butoxy-5-chlorobenzoyl)amino]ethyl}-2-fluorobiphenyl-4-yl)oxy]-2-methylpropanoic acid;
2-butoxy-5-chloro-N-(2-{4'-[1-methyl-1-(1H-tetrazol-5-yl)ethyl]biphenyl-4-yl}ethyl)benzamide;
4'-{2-[(2-butoxy-5-chlorobenzoyl)amino]ethyl}-3-fluorobiphenyl-4-carboxylic acid;
2-[(4'-{2-[(2-butoxy-5-chlorobenzoyl)amino]ethyl}-3-methoxybiphenyl-4-yl)oxy]-2-methylpropanoic acid;
4'-(2-{[5-chloro-2-(hexyloxy)benzoyl]amino}ethyl)biphenyl-4-carboxylic acid;
2-[(4'-{2-[(2-butoxy-5-chlorobenzoyl)amino]ethyl}biphenyl-3-yl)oxy]-2-methylpropanoic acid;
2-{[4'-(2-{[5-chloro-2-(4,4,4-trifluorobutoxy)benzoyl]amino}ethyl)biphenyl-4-yl]oxy}-2-methylpropanoic acid;

4'-(2-{[5-chloro-2-(pentyloxy)benzoyl]amino}ethyl)biphenyl-4-carboxylic acid;
4'-(2-{[5-chloro-2-(heptyloxy)benzoyl]amino}ethyl)biphenyl-4-carboxylic acid;
4'-[2-({5-chloro-2-[(4-methylpentyl)oxy]benzoyl}amino)ethyl]biphenyl-4-carboxylic acid;
2-[(2,3-dichloro-4'-{2-[(5-chloro-2-methoxybenzoyl)amino]ethyl}biphenyl-4-yl)oxy]-2-methylpropanoic acid;
2-butoxy-5-chloro-N-{2-[4'-(1H-tetrazol-5-ylmethyl)biphenyl-4-yl]ethyl}benzamide;
4'-{2-[(2-butoxy-5-chlorobenzoyl)amino]ethyl}-2-methylbiphenyl-4-carboxylic acid;
2-[(4'-{2-[(2-butoxy-5-chlorobenzoyl)amino]ethyl}-3-methylbiphenyl-4-yl)oxy]-2-methylpropanoic acid;
2-[(4'-{2-[(2-butoxy-5-chlorobenzoyl)amino]ethyl}-2-methylbiphenyl-4-yl)oxy]-2-methylpropanoic acid;
2-[(2-chloro-4'-{2-[(5-chloro-2-methoxybenzoyl)amino]ethyl}biphenyl-4-yl)oxy]-2-methylpropanoic acid;
4'-[2-({5-chloro-2-[(3-methylbenzyl)oxy]benzoyl}amino)ethyl]biphenyl-4-carboxylic acid;
2-[(4'-{2-[(5-chloro-2-methoxybenzoyl)amino]ethyl}-2-methylbiphenyl-4-yl)oxy]-2-methylpropanoic acid;
2-[(4'-{2-[(2-butoxy-5-chlorobenzoyl)amino]ethyl}-2,3-dimethylbiphenyl-4-yl)oxy]-2-methylpropanoic acid;
2-[(4'-{2-[(5-chloro-2-methoxybenzoyl)amino]ethyl}-3-methylbiphenyl-4-yl)oxy]-2-methylpropanoic acid;
4'-[2-({5-chloro-2-[(4-methylbenzyl)oxy]benzoyl}amino)ethyl]biphenyl-4-carboxylic acid;
4'-[2-({5-chloro-2-[(6-hydroxyhexyl)oxy]benzoyl}amino)ethyl]biphenyl-4-carboxylic acid;
2-[(4'-{2-[(5-chloro-2-methoxybenzoyl)amino]ethyl}-2-fluorobiphenyl-4-yl)oxy]-2-methylpropanoic acid;
2-[(4'-{2-[(2-butoxy-5-chlorobenzoyl)amino]ethyl}-2-chlorobiphenyl-4-yl)oxy]-2-methylpropanoic acid;
2-[(4'-{2-[(5-chloro-2-isopropoxybenzoyl)amino]ethyl}biphenyl-4-yl)oxy]-2-methylpropanoic acid;
4'-{2-[(2-butoxy-5-chlorobenzoyl)amino]ethyl}-3-methoxybiphenyl-4-carboxylic acid;
2-{[4'-(2-{[5-chloro-2-(3,3,4,4,4-pentafluorobutoxy)benzoyl]amino}ethyl)biphenyl-4-yl]oxy}-2-methylpropanoic acid;
2-[(4'-{2-[(5-chloro-2-methoxybenzoyl)amino]ethyl}-2,5-dimethylbiphenyl-4-yl)oxy]-2-methylpropanoic acid;
4'-[2-({2-[2-(benzyloxy)ethoxy]-5-chlorobenzoyl}amino)ethyl]biphenyl-4-carboxylic acid;
2-{[4'-(2-{[5-chloro-2-(4-fluorobutoxy)benzoyl]amino}ethyl)biphenyl-4-yl]oxy}-2-methylpropanoic acid;
4'-{2-[(2-butoxy-5-chlorobenzoyl)amino]ethyl}-5-fluorobiphenyl-3-carboxylic acid
2-[(4'-{2-[(5-chloro-2-methoxybenzoyl)amino]ethyl}-3-fluorobiphenyl-4-yl)oxy]-2-methylpropanoic acid;
3-(4'-{2-[(2-butoxy-5-chlorobenzoyl)amino]ethyl}biphenyl-4-yl)-2,2-dimethylpropanoic acid;
4'-{2-[(5-bromo-2-butoxybenzoyl)amino]ethyl}biphenyl-4-carboxylic acid;
2-[(4'-{2-[(5-chloro-2-ethoxybenzoyl)amino]ethyl}biphenyl-4-yl)oxy]-2-methylpropanoic acid;
4'-(2-{[5-chloro-2-(4,4,4-trifluorobutoxy)benzoyl]amino}ethyl)biphenyl-4-carboxylic acid;
3-(4'-{2-[(2-butoxy-5-chlorobenzoyl)amino]ethyl}biphenyl-4-yl)propanoic acid;
4'-{2-[(2-butoxy-5-chlorobenzoyl)amino]ethyl}-5-nitrobiphenyl-3-carboxylic acid;
2-(4'-{2-[(2-butoxy-5-chlorobenzoyl)amino]ethyl}biphenyl-4-yl)-2-methylpropanoic acid;
2-[(4'-{2-[(5-chloro-2-methoxybenzoyl)amino]ethyl}-3'-fluorobiphenyl-4-yl)oxy]-2-methylpropanoic acid;
4'-[2-({5-chloro-2-[(4-fluorobenzyl)oxy]benzoyl}amino)ethyl]biphenyl-4-carboxylic acid;
4'-[2-({5-chloro-2-[(3,4-difluorobenzyl)oxy]benzoyl}amino)ethyl]biphenyl-4-carboxylic acid;
(4'-{2-[(2-butoxy-5-chlorobenzoyl)amino]ethyl}-3-nitrobiphenyl-4-yl)acetic acid;
4'-(2-{[5-chloro-2-(3-methylbutoxy)benzoyl]amino}ethyl)biphenyl-4-carboxylic acid;
4'-{2-[(2-butoxy-5-chlorobenzoyl)amino]ethyl}biphenyl-3-carboxylic acid;
4'-[2-({5-chloro-2-[(2-fluorobenzyl)oxy]benzoyl}amino)ethyl]biphenyl-4-carboxylic acid;
4'-{2-[(5-chloro-2-{[3-(trifluoromethyl)benzyl]oxy}benzoyl)amino]ethyl}biphenyl-4-carboxylic acid;
4'-(2-{[5-chloro-2-(cyclobutylmethoxy)benzoyl]amino}ethyl)biphenyl-4-carboxylic acid;
4'-(2-{[(5-bromo-2,2-dimethyl-2,3-dihydro-1-benzofuran-7-yl)carbonyl]amino}ethyl)-biphenyl-4-carboxylic acid;
5-chloro-N-[2-(2'-cyanobiphenyl-4-yl)ethyl]-2-hydroxybenzamide;
3-(4'-{2-[(5-chloro-2-methoxybenzoyl)amino]ethyl}biphenyl-4-yl)-2,2-dimethylpropanoic acid;
2-chloro-4'-{2-[(5-chloro-2-methoxybenzoyl)amino]ethyl}biphenyl-4-carboxylic acid;
2-[(4'-{2-[(2-butoxy-5-chlorobenzoyl)amino]ethyl}-3-cyanobiphenyl-4-yl)oxy]-2-methylpropanoic acid;
4'-[2-({5-chloro-2-[(3-cyanobenzyl)oxy]benzoyl}amino)ethyl]biphenyl-4-carboxylic acid;
4'-(2-{[5-chloro-2-(cyclohexylmethoxy)benzoyl]amino}ethyl)biphenyl-4-carboxylic acid;
4'-{2-[(2-butoxy-5-chlorobenzoyl)amino]ethyl}-6-fluorobiphenyl-3-carboxylic acid;
4'-{2-[(2-butoxy-5-chlorobenzoyl)amino]-1-methylethyl}biphenyl-4-carboxylic acid;
4'-(2-{[5-chloro-2-(3,3,4,4,4-pentafluorobutoxy)benzoyl]amino}ethyl)biphenyl-4-carboxylic acid;
4'-(2-{[(2-butoxy-5-chloropyridin-3-yl)carbonyl]amino}ethyl)biphenyl-4-carboxylic acid;
2-[(4'-{2-[(5-chloro-2-methoxybenzoyl)amino]ethyl}biphenyl-4-yl)oxy]-2-methylpropanoic acid;
2-butoxy-5-chloro-N-(2-{4-[6-(1H-tetrazol-5-yl)pyridin-3-yl]phenyl}ethyl)benzamide;
4'-(2-{[5-chloro-2-(pyridin-2-ylmethoxy)benzoyl]amino}ethyl)biphenyl-4-carboxylic acid;
4'-{2-[(5-chloro-2-{[2-(trifluoromethyl)benzyl]oxy}benzoyl)amino]ethyl}biphenyl-4-carboxylic acid;
2-[(3-chloro-4'-{2-[(5-chloro-2-methoxybenzoyl)amino]ethyl}biphenyl-4-yl)oxy]-2-methylpropanoic acid;
4'-{2-[(2-butoxy-5-chlorobenzoyl)amino]ethyl}-2-cyanobiphenyl-4-carboxylic acid;
4'-{2-[(5-chloro-2-ethoxybenzoyl)amino]ethyl}biphenyl-4-carboxylic acid;
4'-(2-{[5-chloro-2-(1-methylbutoxy)benzoyl]amino}ethyl)biphenyl-4-carboxylic acid;
3-chloro-4'-{2-[(5-chloro-2-methoxybenzoyl)amino]ethyl}biphenyl-4-carboxylic acid;
2-[(2',6'-dichloro-4'-{2-[(5-chloro-2-methoxybenzoyl)amino]ethyl}biphenyl-4-yl)oxy]-2-methylpropanoic acid;
4'-{2-[(5-chloro-2-isobutoxybenzoyl)amino]ethyl}biphenyl-4-carboxylic acid;
4'-{2-[(5-chloro-2-propoxybenzoyl)amino]ethyl}biphenyl-4-carboxylic acid;
4'-[2-({5-chloro-2-[(4-methyl-1,3-thiazol-2-yl)methoxy]benzoyl}amino)ethyl]biphenyl-4-carboxylic acid;

2-[(4'-{2-[(2-butoxy-5-chlorobenzoyl)amino]ethyl}-2,5-dimethylbiphenyl-4-yl)oxy]-2-methylpropanoic acid;
4'-(2-{[5-chloro-2-(4-fluorobutoxy)benzoyl]amino}ethyl)biphenyl-4-carboxylic acid;
2-[(4'-{2-[(2-butoxy-5-chlorobenzoyl)amino]ethyl}-3-chlorobiphenyl-4-yl)oxy]-2-methylpropanoic acid;
4'-{2-[(5-chloro-2-hydroxybenzoyl)amino]ethyl}biphenyl-2-carboxamide;
(4'-{2-[(5-chloro-2-methoxybenzoyl)amino]ethyl}biphenyl-4-yl)acetic acid;
4'-(2-{[5-chloro-2-(cyclopropylmethoxy)benzoyl]amino}ethyl)biphenyl-4-carboxylic acid;
4'-(2-{[5-chloro-2-(pyridin-3-ylmethoxy)benzoyl]amino}ethyl)biphenyl-4-carboxylic acid;
4'-{2-[(2-butoxy-5-chlorobenzoyl)amino]-1,1-dimethylethyl}biphenyl-4-carboxylic acid;
4'-{2-[(2-butoxy-5-chlorobenzoyl)amino]propyl}biphenyl-4-carboxylic acid;
4'-(2-{[(5-bromo-2,3-dihydro-1-benzofuran-7-yl)carbonyl]amino}ethyl)biphenyl-4-carboxylic acid;
2-{[4'-(2-{[5-chloro-2-(3,3,3-trifluoropropoxy)benzoyl]amino}ethyl)biphenyl-4-yl]oxy}-2-methylpropanoic acid;
2-amino-4'-{2-[(2-butoxy-5-chlorobenzoyl)amino]ethyl}biphenyl-4-carboxylic acid;
2-[(4'-{2-[(2-butoxy-5-chlorobenzoyl)amino]ethyl}-2,6-dimethylbiphenyl-4-yl)oxy]-2-methylpropanoic acid;
2-(4'-{2-[(5-chloro-2-methoxybenzoyl)amino]ethyl}biphenyl-4-yl)-2-methylpropanoic acid;
4'-{2-[(2-butoxy-5-pyridin-3-ylbenzoyl)amino]ethyl}biphenyl-4-carboxylic acid;
4'-(2-{[5-chloro-2-(cyclobutyloxy)benzoyl]amino}ethyl)biphenyl-4-carboxylic acid;
4'-{2-[(2-butoxy-5-chlorobenzoyl)amino]ethyl}biphenyl-4-carboxylic acid;
2-(4-{5-[2-(2-butoxy-5-chloro-benzoylamino)-ethyl]-pyridin-2-yl}-phenoxy)-2-methyl-propionic acid;
2-{4'-[2-(2-butoxy-5-chloro-benzoylamino)-ethyl]-3'-ethyl-biphenyl-4-yloxy}-2-methyl-propionic acid
2-{3',5'-Dichloro-4'-[2-(5-chloro-2-methoxy-benzoylamino)-ethyl]-biphenyl-4-yloxy}-2-methyl-propionic acid In all the compounds disclosed in this application, in the event the nomenclature is in conflict with the structure, it shall be understood that the compound is defined by the structure.

Some of the compounds of formula (I) can exist in more than one tautomeric form. The invention includes methods using all such tautomers.

The compounds of the invention are only those which are contemplated to be chemically stable as will be appreciated by those skilled in the art. For example, a compound that would have a dangling valency or carbanion is not a compound contemplated by the present invention.

The invention includes pharmaceutically acceptable derivatives of compounds of formula (I). A "pharmaceutically acceptable derivative" refers to any pharmaceutically acceptable salt or ester, or any other compound that, upon administration to a patient, is capable of providing (directly or indirectly) a compound useful for the invention, or a pharmacologically active metabolite, or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric, and benzenesulfonic acids. Other acids, such as oxalic acid, while not themselves pharmaceutically acceptable per se, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium, and N—(C1-C4 alkyl)4+ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation, and reduction. Specifically, when a prodrug is administered to a patient, the prodrug may be transformed into a compound disclosed hereinabove, thereby imparting the desired pharmacological effect.

General Synthetic Methods

The invention additionally provides for methods for making the compounds of the formula (I). Specific, exemplary procedures are provided in the Synthetic Examples section.

As illustrated in Scheme I, compounds of formula I may be prepared by coupling of a 2-alkoxybenzoicacid II with an amine III using EDC, DDC, or other coupling reagents. The amide nitrogen may be optionally alkylated by reaction with an alkylating reagent ($R_9Y$), such as an alkyl chloride, bromide, iodide, or triflate, in the presence of a suitable base.

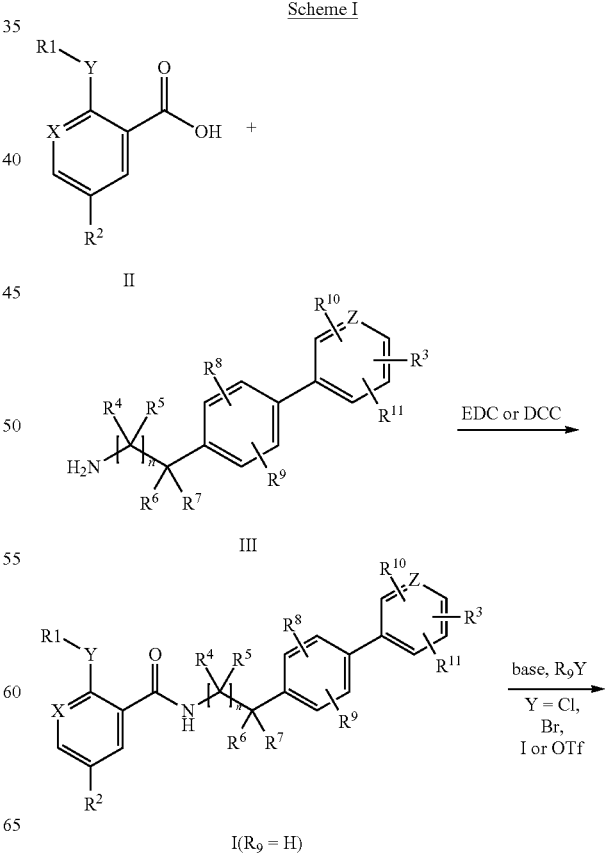

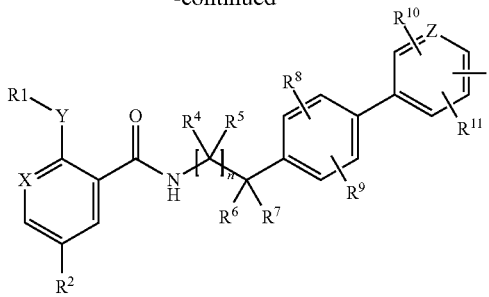

I (R$_9$ is alkyl)

The amine III may be prepared from a protected amine analog IV, where P is a suitable protecting group, such as a t-Boc group, and an organometallic reagent V via cross coupling reactions catalyzed by a transition metal, such as palladium followed by deprotection as illustrated in Scheme II.

Scheme II

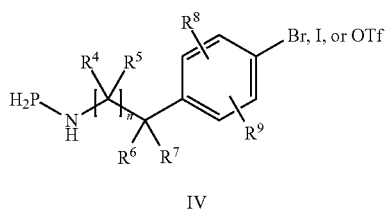

IV
P = Protecting Group

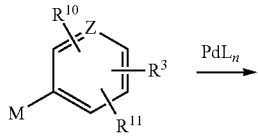

V
M = B, Sn, Zn etc

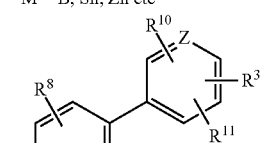

VI

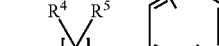

III

Alternatively, compounds of formula I may be prepared according to Scheme III. The benzoic acid derivative II may be coupled with an amine analog IV to provide VII, which may be further coupled with an organometallic reagent to provide compounds of formula I.

Scheme III

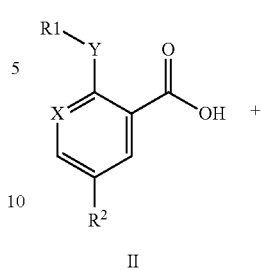

II

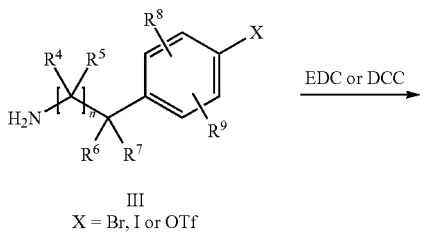

III
X = Br, I or OTf

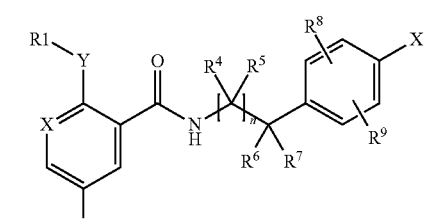

VII

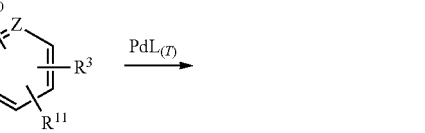

V
M = B, Sn, Zn etc

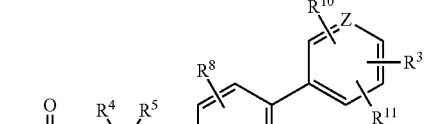

I

Another route useful in preparation of compounds of formula I is shown in Scheme IV. A 2-hydroxybenzoic acid analog II' may be coupled with an amine using standard methods such as EDC or DCC to produce compounds of formula I'. Compounds of formula I' can be reacted with an alkylating reagent R$_1$Y, where Y may be a Cl, Br, I, or TfO, in the presence of a suitable base, to generate compounds of formula I.

Scheme IV
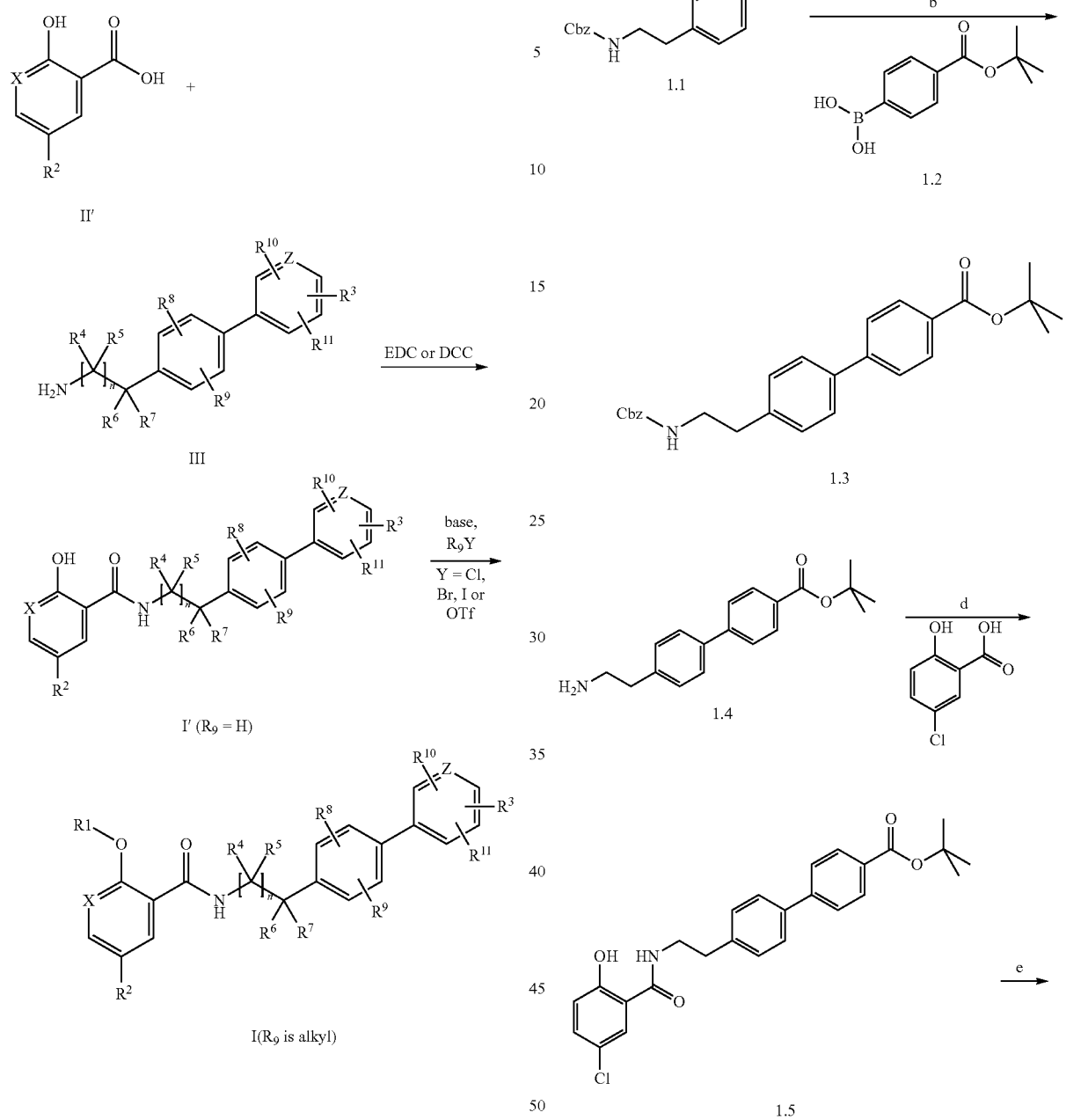
SYNTHETIC EXAMPLES
Synthesis of 4'-(2-{[5-chloro-2-(pentyloxy)benzoyl]amino}ethyl)biphenyl-4-carboxylic acid (Compound 22)
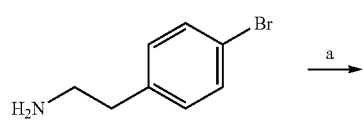

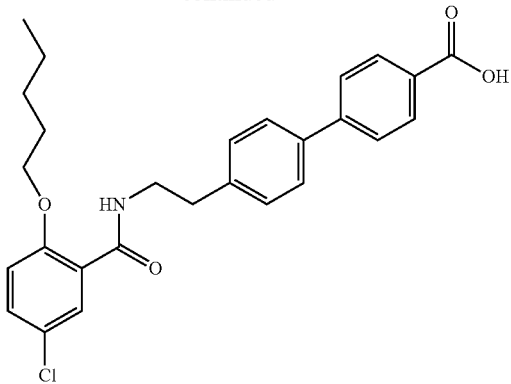

22

Reagents and Conditions: a) CbzCl, Et₃N, CH₂Cl₂, −30→23° C., 5 h; b) PdCl₂(dppf), 2 M aq. Na₂CO₃, DME, 85° C., 18 h; c) H₂, 10% Pd—C, CH₂Cl₂-EtOH, 6 h; d) EDC, HOBt, i-Pr₂NEt, DMF, 14 h; e) Alkyl bromide, Cs₂CO₃ or K₂CO₃ or NaHCO₃ (for 1° alkyl bromide), 80° C.; f) TFA, CH₂Cl₂, 23° C., 5-15 h.

A solution of 4-bromophenylethyl amine (4.7 g, 23.5 mmol) and Et₃N (6.5 mL, 47.0 mmol) in 100 mL of CH₂Cl₂ is cooled to −30° C. Benzyl chloroformate (4 ml, 28.2 mmol) is added drop-wise. The reaction mixture is allowed to warm up to 23° C. slowly and stirred for 5 h. The reaction mixture is poured into crushed ice-water and extracted with CH₂Cl₂ (100 mL×3). The organic layer is washed with water, brine, and dried over Na₂SO₄, and concentrated in vacuo. The crude product is purified by passing through a silica gel pad and eluting with 5% MeOH in CH₂Cl₂ and then 1:2 EtOAc-hexanes to give the desired intermediate 1.1 (7.5 g, 97%) as a white solid.

To a solution of the bromide obtained above (5.5 g, 16.5 mmol) and the boronic acid 1.2 (7.3 g, 33 mmol) in 50 mL of DMF is added an aq. Na₂CO₃ solution (2 M, 22 mL, 44 mmol). The mixture is purged with Ar₂ for 10 min PdCl₂ (dppf) (672 mg, 0.82 mmol) is then added. The reaction is stirred under Ar₂ at 85° C. for 18 h. After cooling the reaction mixture is poured into water (200 mL). The mixture then is extracted with EtOAc (50 mL×3). The organic layer is separated and dried over Na₂SO₄ and concentrated in vacuo. The crude product is purified by chromatography to provide the desired product 1.3 (5.5 g, 77%).

The above carbamate 1.3 is dissolved in CH₂Cl₂ (57 mL) and then EtOH (570 mL) is added, followed by 10% Pd/C (1.5 g). The mixture is then stirred under 1 atmosphere H₂ for 6 h. The reaction mixture is filtered through a pad of diatomaceous earth and the solid residues are rinsed with EtOH. The filtrate is concentrated in vacuo to give the desired amine 1.4 as a white solid (4.9 g, 100%).

A mixture of 5-chloro-2-hydroxybenzoic acid (2.1 g, 12.2 mmol), the above amine (3.0 g, 10.1 mmol), EDC (2.9 g, 15.1 mmol), HOBt (2.0 g, 15.0 mmol), Hunig's base (2.8 mL, 16.1 mmol) in 20 mL of DMF is stirred at 23° C. for 14 h. The reaction mixture is diluted with EtOAc (200 mL), washed with 1 M NaHSO₄, sat. aq. NaHCO₃, water, brine, dried over Na₂SO₄, and concentrated in vacuo. The crude product is triturated in 25 mL of 1:1 hexane-EtOAc to give the desired amide 1.5 (2.54 g, 56%).

The above amide 1.5 (70 mg, 0.16 mmol) is dissolved in 1 mL DMF. Pentyl bromide (100 mg, 0.66 mmol) is then added followed by Cs₂CO₃ (100 mg, 0.31 mmol). The mixture is stirred at 85° C. for 14 h. The reaction mixture is diluted with EtOAc and washed with water three times and dried over Na₂SO₄, and concentrated in vacuo to give the desired product 1.6 (76 mg, 94%).

The above ester 1.6 (55 mg, 0.11 mmol) is dissolved in 2 mL of CH₂Cl₂. TFA (0.5 ml) is then added and the mixture is stirred at 23° C. for 5 h. The solvents are removed in vacuo, the residue is dissolved in 2 mL of MeOH, and diluted with 10 mL of 0.1 M aq. NaOH. The mixture is then extracted with 20 mL of ether. The aqueous layer is separated and acidified with 3 N HCl to pH 2, and extracted with 50 mL of EtOAc. The EtOAc extract is washed with brine, dried over Na₂SO₄, and concentrated in vacuo to give the title compound 22 (48 mg, 98%).

Example 2

Synthesis of 4'-{2-[(2-butoxy-5-chlorobenzoyl)amino]ethyl}biphenyl-4-carboxylic acid (Compound 156)

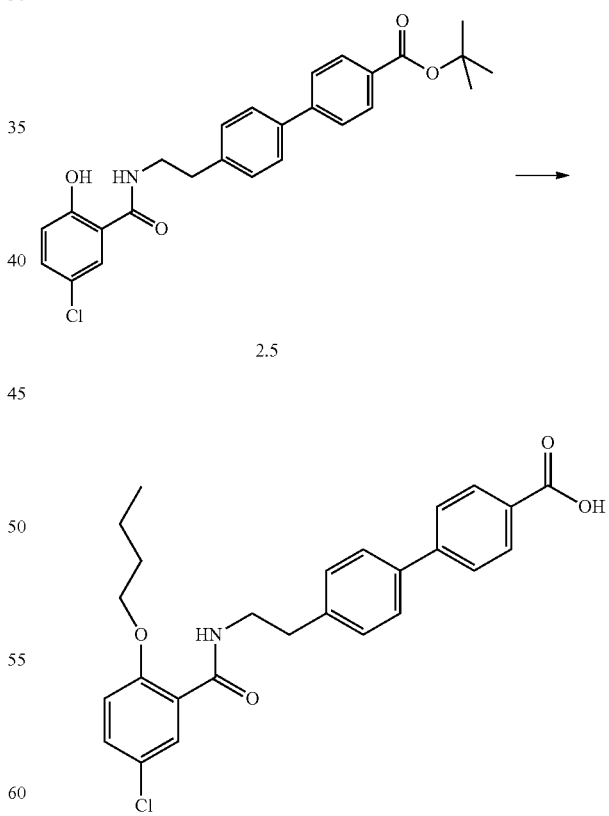

Compound 156 is prepared from intermediate 2.5 and n-BuBr by the same procedure as the preparation of compound 7.

Example 3
Synthesis of 2-{[4'-(2-{[5-chloro-2-(4,4,4-trifluorobutoxy)benzoyl]amino}ethyl)-biphenyl-4-yl]oxy}-2-methylpropanoic acid (Compound 21)
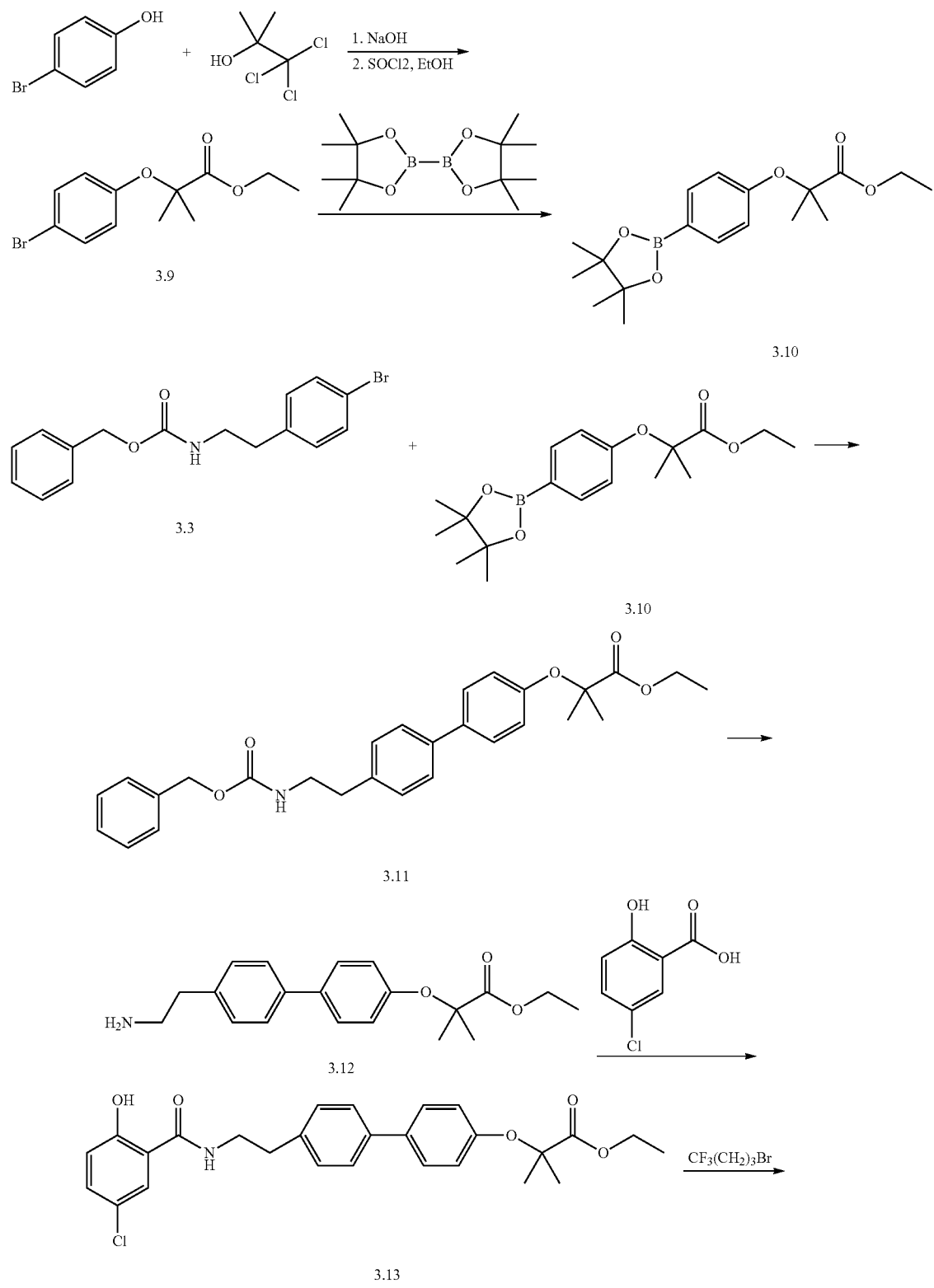

-continued

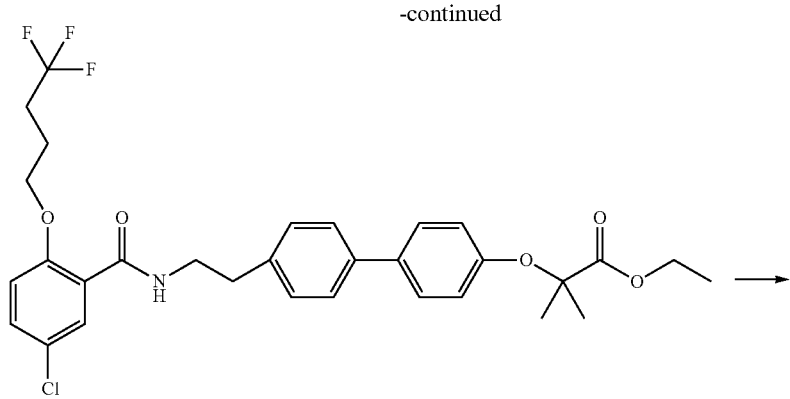

3.14

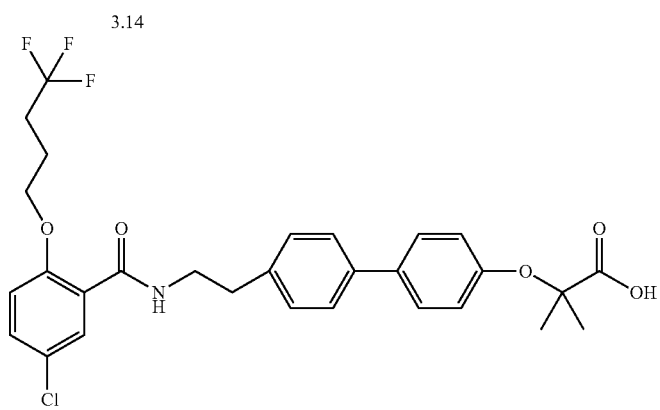

21

4-Bromophenol (10 g, 57.8 mmol, 1 eq.) and 1,1,1-trichloro-2-methyl-2-propanol hemihydrate (20.5 g, 115.6 mmol, 2 eq.) in 200 mL acetone is treated with solid NaOH (18.5 g, 462.4 mmol, 8 eq.) and the reaction mixture is stirred at ambient temperature overnight. The solvent is removed under reduced pressure and the resulting residue is dissolved in 10 mL water. The resulting solution is acidified with 3 N HCl and extracted with ether. The extracts are washed twice with brine and dried over anhydrous MgSO$_4$. The filtered solvent is removed under reduced pressure to give 2.5 g crude product.

The crude carboxylic acid (2.5 g) is dissolved in 200 mL EtOH without further purification and SOCl$_2$ (4.83 mL, 57.8 mmol, 1 eq.) is added drop-wise to the stirring solution at ambient temperature. The mixture is then heated to reflux and stirred for 6 h. The reaction mixture is concentrated under reduced pressure. The residue is dissolved in the 100 mL ether and washed with water, saturated aqueous NaHCO3, and saturated brine successively. The organic layer is dried over anhydrous MgSO4 and concentrated under reduced pressure after filtration. The crude product is purified with a combi-flash column (20%-40% EtOAc/hexane, on 40 g column) to yield yellow oil as product 3.9 (14.0 g, 48.8 mmol, 84.4%).

A solution of 2-(4-bromo-phenoxy)-2-methyl-propionic acid ethyl ester (9, 35 mmol, 1 eq.), bis(pinacolato)diboron (11 g, 43 mmol, 1.2 eq.), and KOAc (7 g, 72 mmol, 2 eq.) in 100 mL anhydrous DMSO is purged with Argon for 10 min The PdCl$_2$(dppf) (1.5 g, 1.9 mmol, 0.1 eq.) catalyst is then added and the reaction mixture is sealed in a seal tube and stirred at 100° C. overnight. After cooling down, the reaction mixture is diluted with EtOAc and washed with water and brine. The organic layer is dried over Na$_2$SO$_4$, filtered and concentrated to give a dark oil that is purified on a combiflash column (40%-60% EtOAc in hexane, 40 g column) and yields 10 (11 g, 33 mmol, 94%) as a white solid.

A solution of intermediate 3.3 (2 g, 6 mmol, 1 eq.) and intermediate 3.10 (2 g, 6 mmol, 1 eq.) in DMF is purged with Ar$_2$ for 10 min. Pd(dppf)Cl$_2$ (122 mg, 0.15 mmol, 0.4 eq.) and 8 mL 2N Na$_2$CO$_3$/H$_2$O are then added and the resulting reaction mixture is sealed in a tube and heated to 120° C. in a microwave oven for 30 min The reaction mixture is diluted with EtOAc and washed with water and brine. The organic layer is dried over Na$_2$SO$_4$, filtered and concentrated to give a dark oil that is purified by flash column (40%~60% EtOAc/hexanes, 40 g column) yielding intermediate 3.11 as a light greenish oil (2 g, 4.3 mmol, 72%).

Intermediate 3.11 (1.6 g, 3.5 mmol, 1 eq.) is dissolved in 150 mL of EtOH/DCM (10:1). 5% Pd/C is added to the solution and the resulting suspension is stirred under hydrogen for 3.12 hours. The reaction mixture is filtered through diatomaceous earth and washed with ethanol. After the solvent is evaporated under reduce pressure, intermediate 3.12 is obtained as white solid (1.13 g, 3.5 mmol, 99%).

A solution of ethyl amino-biphenyl-2-methyl-propionic acid ethyl ester (12, 690 mg, 2.1 mmol, 1 eq.) and 5-chloro-salicylic acid (727 mg, 4.2 mmol, 2 eq.), in 10 mL DMF is treated with EDC (802 mg, 4.2 mmol, 2 eq.), HOBT (569 mg, 4.2 mmol, 2 eq.) and DMAP (26 mg, 0.2 mmol, 0.2 eq.). After stirring at ambient temperature for 48 h, the reaction mixture is extracted between EtOAc and water. The organic layer is washed with saturated NaHCO$_3$, saturated NaCl solution, and water. After drying over Na$_2$SO$_4$, the organic solvent is filtered and evaporated under reduce pressure. The crude product is loaded onto a Biotage column with 1 mL of CH$_2$Cl$_2$.

The column is eluted with 10% EtOAc/hexanes to yield 3.13 as a white solid (1.6 g, 3.5 mmol, 1 eq.).

Intermediate 3.13 (70 mg, 0.15 mmol, 1 eq.), in 1 mL DMF is treated with NaHCO$_3$ (60 mg, 0.73 mmol, 5 eq.) and then 4-bromo-1,1,1-trifluoro-butane (88 mg, 0.45 mmol, 3 eq.) is added drop-wise. The reaction mixture is heated to 120° C. for 30 min by microwave. After cooling down to room temperature, 10 mL water is added and the reaction is extracted with 50 mL EtOAc and washed with water. After the organic layer is dried over NaSO$_4$, filtered, and evaporated under reduced pressure, crude product is obtained. The crude product is loaded on the pre-TLC and developed with hexanes/EtOAc (3:1) to yield clear 3.14 as a thick oil (84 mg, 0.14 mmol, 97%).

A solution of 3.14 (40 mg, 0.07 mmol, 1 eq.), in 0.5 mL THF/MeOH (1:1) is treated with 70 µl 2N NaOH/H$_2$O solution and the resulting reaction mixture is stirred at 50° C. for 2 h. The solvent is evaporated and 1 mL water is added to the residue. The residue is acidified carefully with 1 N HCl and the resulting solution is extracted with EtOAc. The organic solvent is dried, filtered, and evaporated under reduced pressure to yield the title compound 21 as a white solid (36 mg, 0.06 mmol, 95%).

Example 4

Synthesis of 2-[(4'-{2-[(2-butoxy-5-chlorobenzoyl)amino]ethyl}biphenyl-4-yl)oxy]-2-methylpropanoic acid (Compound 6)

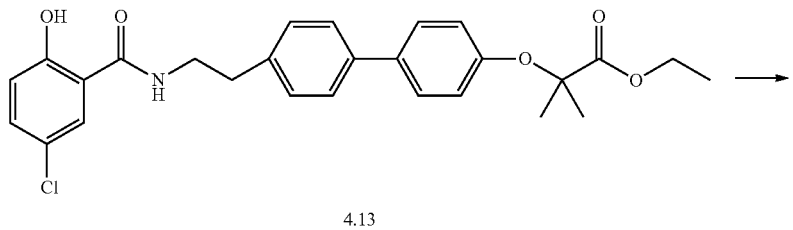

4.13

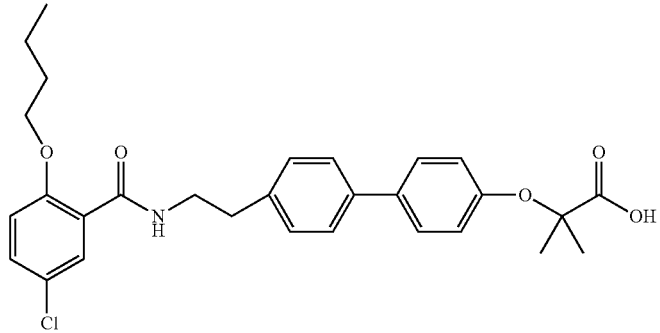

6

Compound 6 is synthesized from 4.13 and n-BuBr using the same procedure as described for the preparation of intermediate 3.15 in the above Example.

Example 5

Synthesis of 4'-{2-[(5-bromo-2-butoxybenzoyl)amino]ethyl}-biphenyl-4-carboxylic acid (Compound 48)

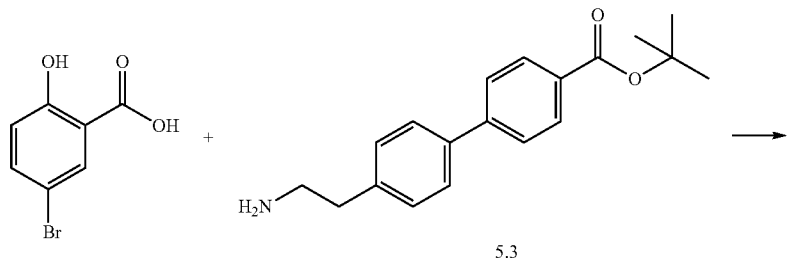

5.3

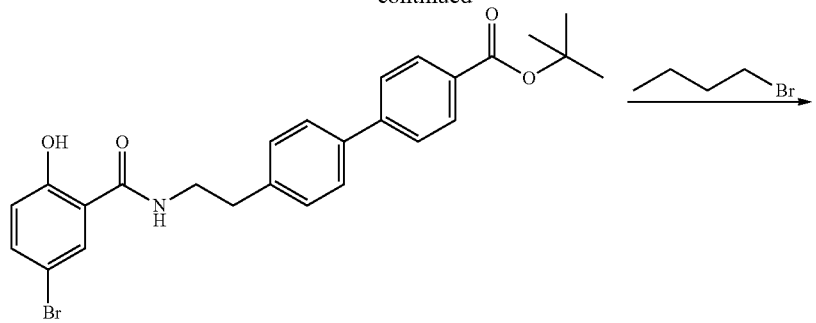

5.17

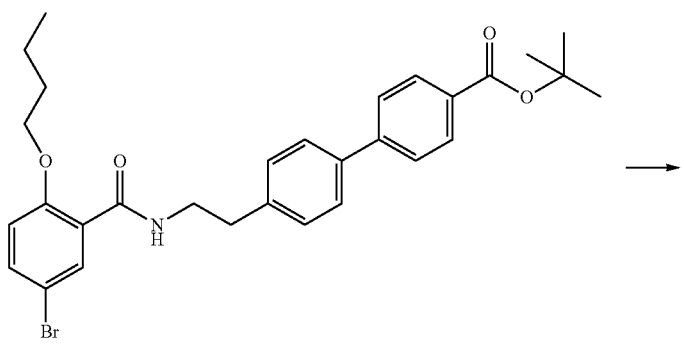

5.18

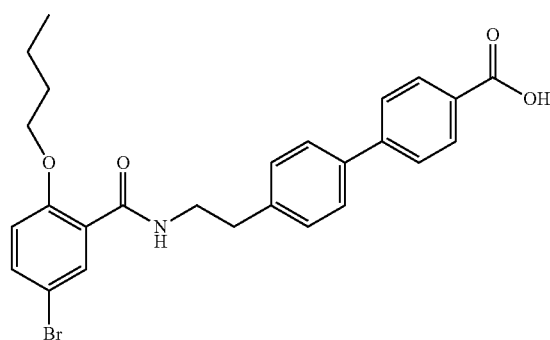

48

To a solution of 5-bromosalicylic acid (300 mg, 1.24 mmol), amine 5.3 (359 mg, 1.21 mmol), and HOBT (202 mg, 1.49 mmol) in DMF (10 mL) is added EDC (358 mg, 1.87 mmol) followed by DMAP. The mixture is stirred at room temperature overnight. After removal of the solvent, the mixture is purified by silica gel chromatography using 0-40% ethyl acetate-hexane (gradient) to give 500 mg of product 5.17.

To a solution of 5.17 (100 mg, 0.20 mmol) in DMF (2 mL) is add NaHCO$_3$ (68 mg, 0.81 mmol) followed by n-butyl bromide (55 mg, 0.40 mmol). The mixture is heated at 60° C. for 4 hours, cooled to room temperature, and concentrated. Purification of the residue by silica gel chromatography using 0-40% ethyl acetate-hexane (gradient) gives 98 mg of intermediate 5.18.

To a solution of ester 5.18 (58 mg, 0.105 mmol) in dichloromethane (1.5 mL) is added trifluoroacetic acid (0.5 mL). The mixture is stirred at room temperature overnight. Removal of the solvent gives 48 mg of the title compound 48 as white solid.

Example 6

Synthesis of 4'-{2-[(2-butoxy-5-pyrimidin-5-ylbenzoyl)amino]ethyl}-biphenyl-4-carboxylic acid (Compound 104)

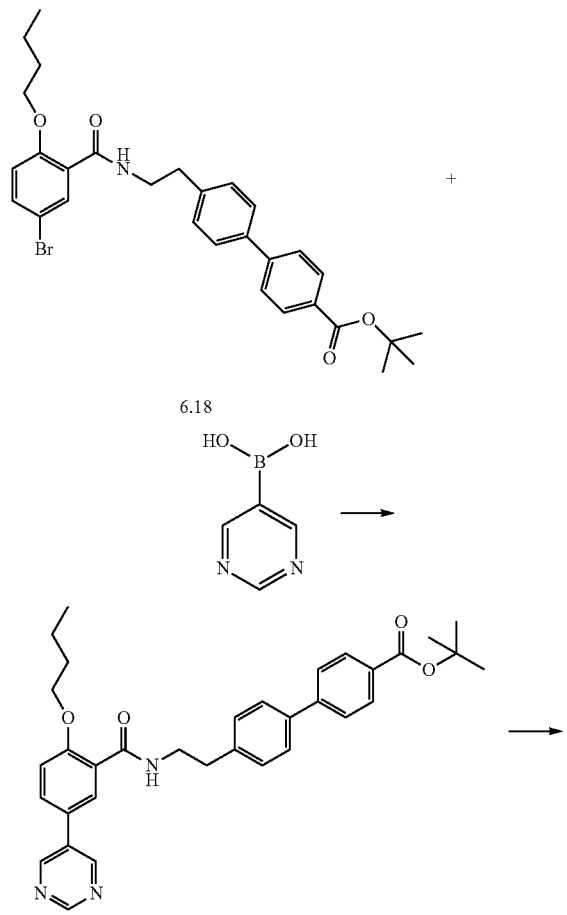

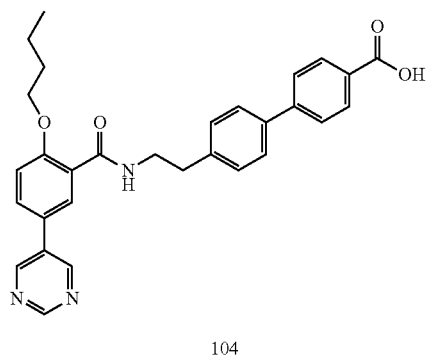

104

To a solution of bromide 6.18 (56 mg, 0.10 mmol) and 3,5-pyrimidineboronic acid (22 mg, 0.18 mmol.) in DMF (5 mL) is added sodium carbonate solution (2M, 0.2 mL, 0.4 mmol). The mixture is degassed using $N_2$ for 5 min before $PdCl_2(dppf)CH_2Cl_2$ (7 mg, 0.01 mmol.) is added. The mixture is heated at 90° C. overnight. The mixture is concentrated and purified by silica gel chromatography using MeOH-DCM 0-5% (gradient) to give 67 mg of the cross coupling product.

The product from above (46 mg, 0.077 mmol) is dissolved in DCM (2 mL) and treated with trifluoroacetic acid (TFA, 0.2 mL). The mixture is stirred at room temperature overnight and concentrated. The residue is washed with acetonitrile to give 29 mg of the title compound 104 as a white solid.

Example 7

Synthesis of 4'-{2-[(2-butoxy-5-chlorobenzoyl)amino]propyl}biphenyl-4-carboxylic acid (Compound 95)

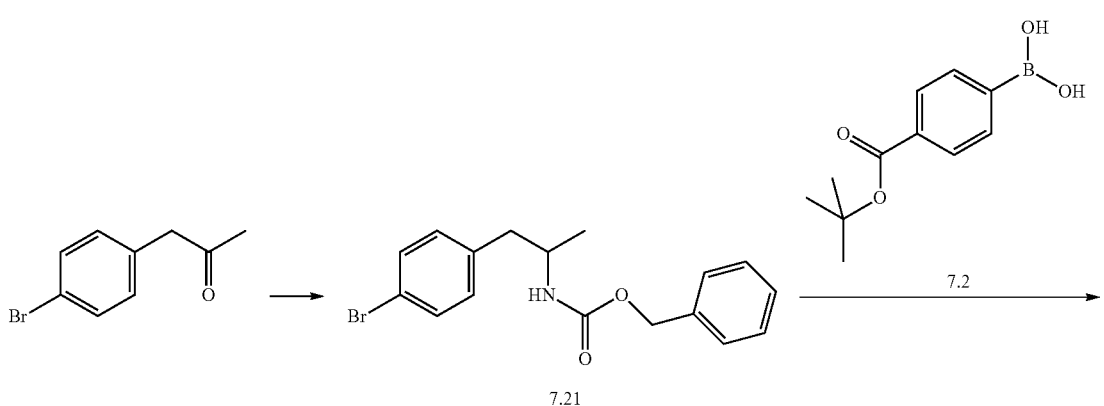

-continued

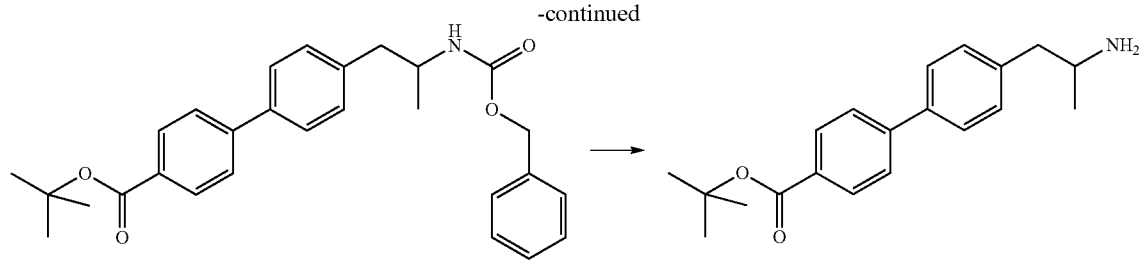

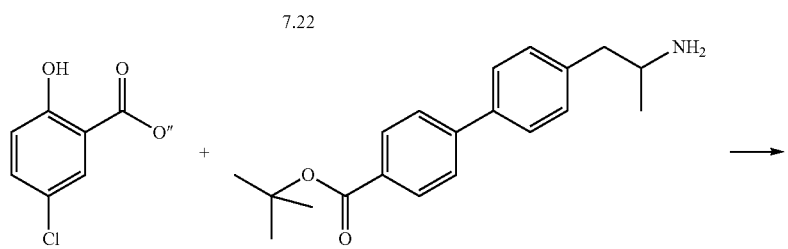

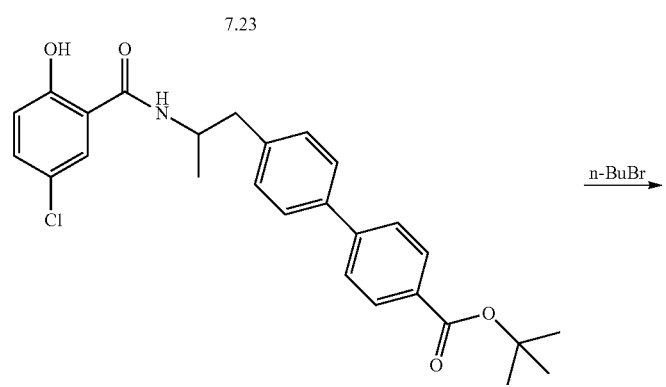

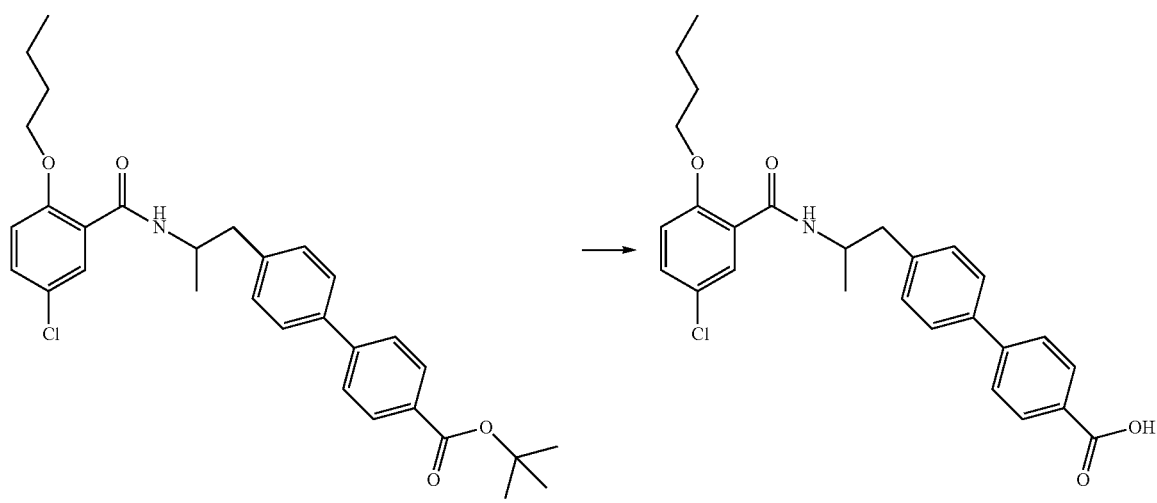

To a solution of 4-bromophenylacetone (2 g, 9.4 mmol) in methanol (50 mL) is added ammonium acetate (10.8 g, 140 mmol) followed by Na(CN)BH$_3$ (3 g, 48 mmol). The mixture is heated to 70° C. (reflux) overnight. After cooling to 0° C., H$_2$O (100 mL) is added. 50% NaOH solution is then added to the mixture to adjust pH to ~10. The mixture is then stirred at room temperature for 2 hours, extracted with DCM (100 mL×3), dried with Na$_2$SO$_4$ and concentrated to give 2.37 g of the crude reductive amination product as a yellowish oil.

To a solution of the crude product from above (1 g, ~4.67 mmol) in DCM cooled to 0° C. is added TEA (3 mL, 21.4 mmol) followed by CbzCl (0.7 mL, 4.67 mmol) drop-wise. The mixture is then stirred at room temperature overnight. The mixture is poured into H$_2$O (50 mL), extracted with DCM, dried with Na$_2$SO$_4$, and concentrated. Silica gel chromatography of the residue using 25% ethyl acetate-hexane gives 710 mg of intermediate 7.21.

To a solution of bromide 7.21 (500 mg, 1.44 mmol) and boronic acid 2 (319 mg, 1.44 mmol) in DMF (10 mL) is added cesium carbonate (936 mg, 2.87 mmol) followed by palladium acetate (16 mg, 0.072 mmol). The mixture is degassed using an Ar stream and stirred at 90° C. overnight. The mixture is cooled to room temperature, filtered through diatomaceous earth, and partitioned between EtOAc, and water. The organic layer is dried over $Na_2SO_4$ and concentrated. Silica gel chromatography of the residue provides 360 mg of intermediate 7.22

To a mixture of 7.22 (340 mg, 0.76 mmol) and Pd—C (10%, 80 mg) in EtOAc (5 mL) and MeOH (5 mL) is added cyclohexene (5 mL). The mixture is then heated in a sealed vial under $N_2$ at 70° C. overnight. The mixture is cooled, filtered, and concentrated to give the crude amine 7.23.

To a solution of 7.23 (0.7 mmol), 5-chlorosalicyclic acid (150 mg, 0.87 mmol) in DMF (5 mL) is added HOBT (235 mg, 1.74 mmol) then EDC (333 mg, 1.74 mmol) followed by DMAP (10 mg). The mixture is stirred at room temperature overnight and concentrated. SGC with 20% E-H gives ~500 mg of yellowish oil. The product thus obtained may be further purified by SGC using 0-15% E-H to give 105 mg of 7.24 as a white solid.

To a solution of compound 7.24 (85 mg, 0.18 mmol) in DMF (5 mL) is added $NaHCO_3$ (43 mg, 0.52 mmol) then butyl bromide (37 microL, 0.34 mmol). The mixture is heated at 60° C. overnight under $N_2$, concentrated and purified by GSC using 0-5% DCM-MeOH to give 95 mg of 7.25 as thick oil, which turned into a glassy material upon drying under vacuum (99%).

To a solution of 7.25 (70 mg, 0.13 mmol) in DCM (1 mL) is added TFA (0.2 mL). The mixture is stirred at room temperature for 4 hours and concentrated to give 61 mg of the title compound 95.

Example 8

Synthesis of 4'-[2-(2-butoxy-5-chlorobenzoylamino)-1-methyl-ethyl]-biphenyl-4-carboxylic acid (Compound 71)

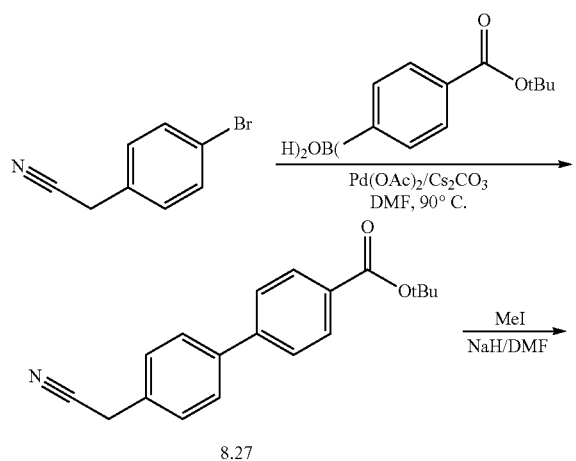

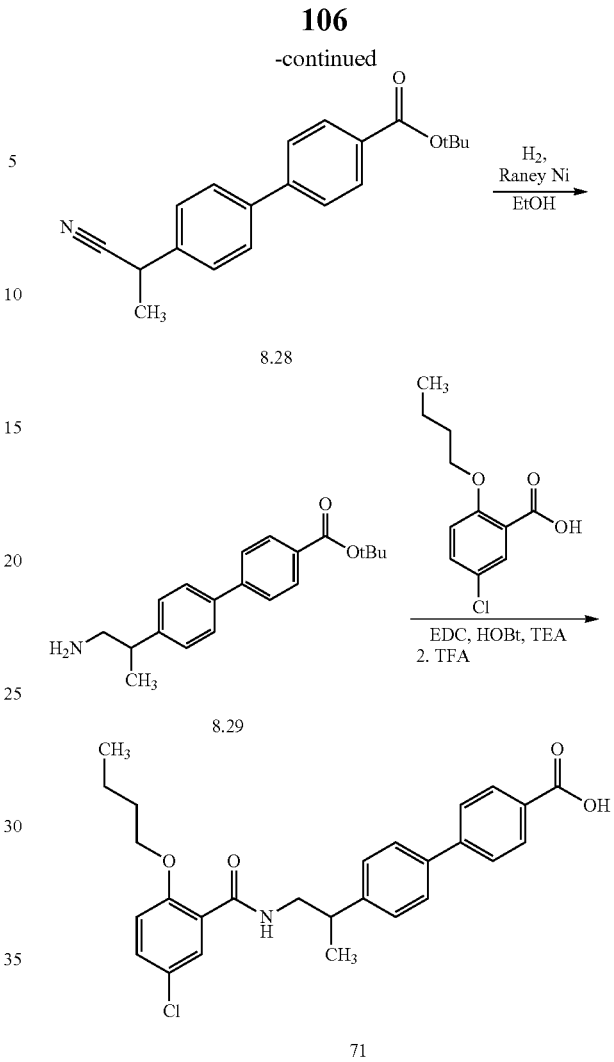

Into a 250 mL round-bottomed flask are placed 4-bromophenyl acetonitrile (2.5 g, 12.7 mmol), (4-t-butylcarbonyl)boronic acid (2.82 g, 12.7 mmol), and palladium (II) acetate (0.25 g, 1.11 mmol). A 2 M solution of $Cs_2CO_3$ (10.5 mL) is added to the flask followed by DMF (50 mL) and the mixture is heated at 90° C. for 18 h. The reaction mixture is cooled, diluted with EtOAc (100 mL), and washed with water (5×100 mL), 2 M HCl (50 mL), and brine (100 mL). The organic layer is dried over $Na_2SO_4$, filtered, concentrated to dryness, and the resulting residue may be purified by flash silica gel chromatography (eluent: 15% EtOAc in hexanes) to give 8.27 (1.25 g, 37%) as a yellow solid.

Sodium hydride (60% in mineral oil, 34 mg, 0.85 mmol) is placed into a 100 mL round-bottomed flask and washed with hexanes. A solution of biphenyl acetonitrile 8.27 (0.25 g, 0.85 mmol) in DMF (15 mL) is added to the flask, and its contents is stirred for 30 min at room temperature. Iodomethane (0.12 g, 0.85 mmol) is then added and the reaction mixture stirred overnight. The reaction mixture is diluted with EtOAc (25 mL) and washed with brine (7×25 mL). The organic layer is separated, dried over $Na_2SO_4$, filtered and evaporated to dryness to give a crude solid that is purified by flash silica gel chromatography (eluent: 15% EtOAc in hexanes). Fractions are combined and evaporated to give 8.28 (0.2 g, 77%) as a light yellow solid.

Nitrile 8.28 (0.3 g, 1.0 mmol) is dissolved in MeOH and added to 50% Raney nickel and subjected to hydrogenation at 50 psi overnight in a Parr shaker The reaction mixture is filtered through a short pad of diatomaceous earth and concentrated to dryness to give 0.20 g of crude 8.29 (67%) of as a dark yellow solid that is usable for the next reaction without purification.

Amine 8.29 (0.20 g, 0.64 mmol), 2-butoxy-5-chlorobenzoic acid (0.15 g, 0.65 mmol), EDC.HCl (0.15 g, 0.77 mmol), HOBt (0.10 g, 0.77 mmol) and TEA (0.08 g, 0.77 mmol) are dissolved in CHCl$_3$ (10 mL) and stirred overnight. The reaction mixture is washed with water (10 mL), 1 M HCl (2×10 mL), and brine (10 mL), dried over Na$_2$SO$_4$, filtered and evaporated to dryness to give the crude product. Purification by flash silica gel chromatography (eluent: 20% EtOAc in hexanes) gives the t-butyl ester of 71 (0.10 g, 30%) as an off-white solid. The t-butyl ester (0.10 g, 0.24 mmol) is dissolved in 3:1 CH$_2$Cl$_2$/TFA (40 mL), stirred for 12 h, and evaporated to dryness to give the title compound 71 (80 mg, 88%) as an off-white solid.

Example 9

Synthesis of 4'-[2-(2-butoxy-5-chloro-benzoylamino)-1,1-dimethyl-ethyl]-biphenyl-4-carboxylic acid (Compound 94)

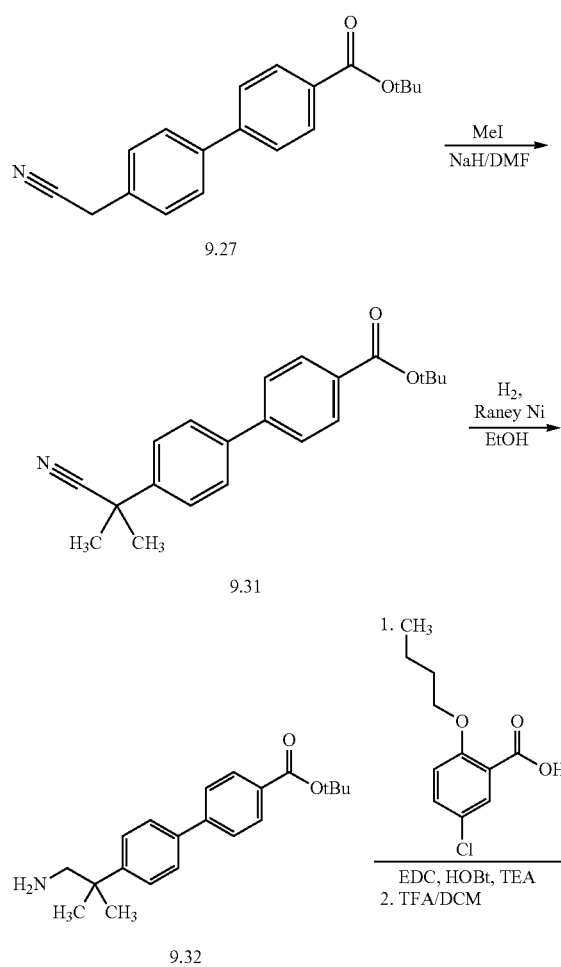

-continued

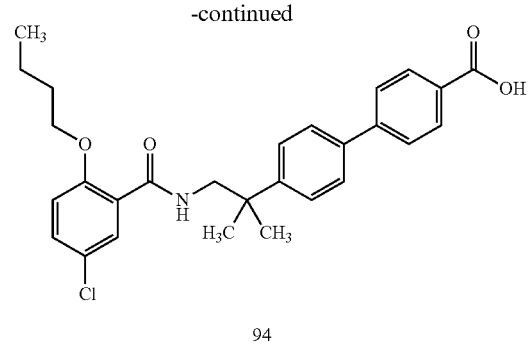

94

Sodium hydride (60% in mineral oil, 0.19 g, 4.7 mmol) is weighed into a 100 mL round-bottomed flask and washed with hexanes. A solution of 9.27 (0.55 g, 1.9 mmol) in DMF (20 mL) is added to the flask, and its contents is stirred for 30 min at room temperature. Iodomethane (0.80 g, 5.6 mmol) is then added and the reaction mixture stirred overnight. The reaction mixture is diluted with EtOAc (50 mL) and washed with brine (7×50 mL). The organic layer is separated, dried over Na$_2$SO$_4$, filtered and evaporated to dryness to give a crude solid which is purified by flash silica gel chromatography (eluent: 15% EtOAc in hexanes). Fractions are combined and evaporated to give 9.31 (0.35 g, 58%) as a yellow solid.

Nitrile 9.31 (0.35 g, 1.1 mmol) is dissolved in MeOH and added to 50% Raney nickel (0.2 g) and subjected to hydrogenation at 45 psi overnight in a Parr shaker. The reaction mixture is filtered through a short pad of diatomaceous earth and concentrated to dryness to give 0.21 g (49%) of crude 9.32 as a dark yellow solid that is usable for the next reaction without purification.

Amine 9.32 (0.17 g, 0.53 mmol), 2-butoxy-5-chlorobenzoic acid (0.12 g, 0.53 mmol), EDC.HCl (0.12 g, 0.64 mmol), HOBt (86 mg, 0.64 mmol) and TEA (64 mg, 0.64 mmol) are dissolved in CHCl$_3$ (10 mL) and stirred overnight. The reaction mixture is washed with water (10 mL), 1 M HCl (2×10 mL), and brine (10 mL), dried over Na$_2$SO$_4$, filtered and evaporated to dryness to give the crude product. Purification by flash silica gel chromatography (eluent: 20% EtOAc in hexanes) gives the t-butyl ester of 28 (0.12 g, 50%) as an off-white solid. The t-butyl ester (0.12 g, 0.22 mmol) is dissolved in 3:1 CH$_2$Cl$_2$/TFA (40 mL), stirred for 12 h and evaporated to dryness to give the title compound 94 (51 mg, 50%) as an off-white solid.

Example 10

Synthesis of 4'-[2-(2-Butoxy-5-chloro-benzoylamino)-2-methyl-propyl]biphenyl-4-carboxylic acid (Compound 137)

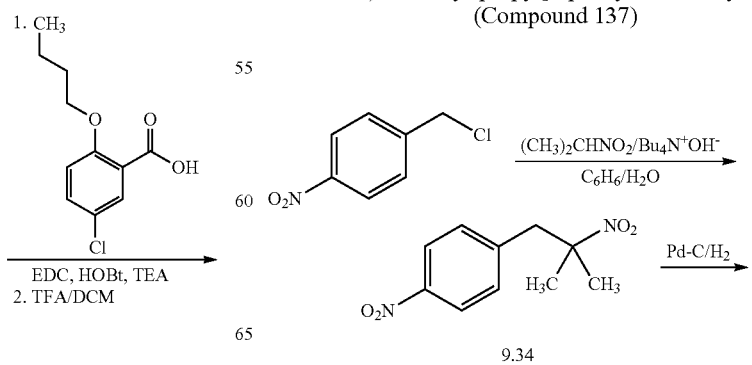

109

-continued

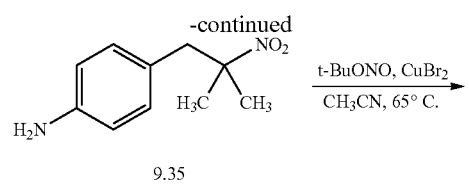
9.35

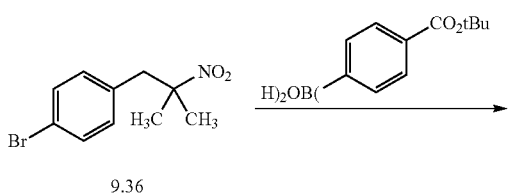
9.36

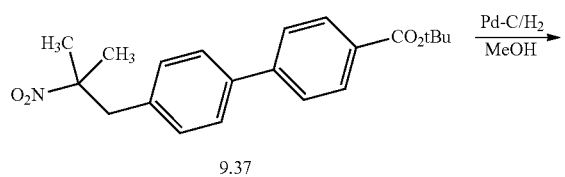
9.37

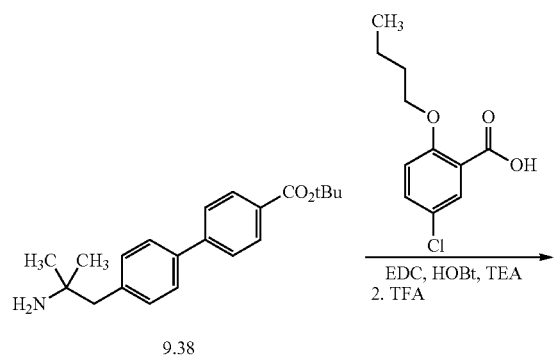
9.38

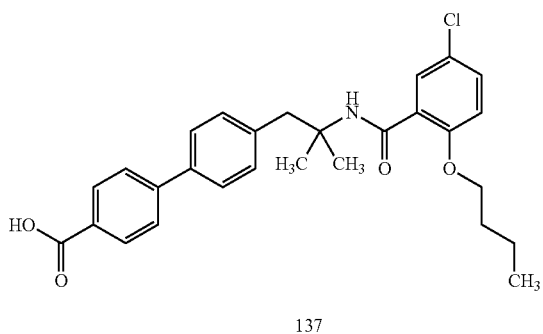
137

A solution of 4-nitrobenzyl chloride (2.0 g, 11.7 mmol) in benzene (15 mL) is stirred under nitrogen with a solution of 2-nitropropane (1.5 g, 16.8 mmol) and 1 M tetrabutylammonium hydroxide in water (25 mL) for 3 h. More benzene (100 mL) is added to the reaction mixture followed by the separation of phases, drying of the organic layer over $Na_2SO_4$, filtration to remove the drying agent and the evaporation of solvents. The resulting crude solid is purified by flash silica gel chromatography (eluent: 15% EtOAc in hexanes) to give 10.34 (1.6 g, 62%).

To a solution of 10.34 (1.5 g, 6.7 mmol) in MeOH (50 mL) is added 10 wt. % Pd—C (0.7 g, 0.67 mmol). The reaction mixture is then subjected to hydrogenation at 1 atm and is stopped when 10.34 is totally consumed. The diamine overreduction product is separated from the desired monoamine product by a flash silica gel chromatography (eluent: 50% $CH_2Cl_2$ in hexanes) to give 10.35 (0.65 g, 50%).

t-Butyl nitrite (0.52 g, 5.0 mmol) and $CuBr_2$ (0.94 g, 4.0 mmol) are weighed into a 100 mL 3-necked round-bottomed flask fitted with a condenser, addition funnel and a gas outlet tube. Anhydrous acetonitrile (10 mL) is added and the mixture is heated to 65° C. A solution of 10.35 (0.65 g, 3.4 mmol) in acetonitrile (7 mL) is added to the heated reaction mixture drop wise with vigorous stirring. Heating and stirring is continued for 16 h after which the resulting black reaction mixture is cooled and poured into 20% aqueous HCl (100 mL). The aqueous acetonitrile mixture is extracted with diethyl ether (2×100 mL) and the combined ether extracts are dried over $MgSO_4$, filtered and evaporated to dryness to give a yellow viscous oil (0.84 g, 99%). $^1H$ NMR analysis indicates the product is a 3:1 mixture of the desired 4-bromo compound 10.36 and the 3,4-dibromo by-product. This mixture is taken to the next step without further purification.

Into a 50 mL round-bottomed flask are weighed crude 10.36 (0.63 g, 2.4 mmol), (4-t-butylcarbonyl)boronic acid (0.73 g, 3.3 mmol), and palladium (II) acetate (73 mg, 0.33 mmol). A 2 M solution of $Cs_2CO_3$ (3.0 mL) is added to the flask followed by DMF (20 mL), and the mixture is heated at 90° C. for 18 h. The reaction mixture is cooled, diluted with EtOAc (10 mL) and washed with water (5×10 mL), 2 M HCl (10 mL) and brine (10 mL). The organic layer is dried over $Na_2SO_4$, filtered, concentrated to dryness and the resulting residue is purified by trituration with MeOH to give 10.37 (0.12 g, 22%) as an off-white solid.

A solution of the biphenyl nitro compound 10.37 (0.12 g, 0.34 mmol) in MeOH (25 mL) is added to 10 wt. % Pd—C and subjected to hydrogenation at 40 psi overnight. The reaction mixture is filtered through a short pad of diatomaceous earth and the filtrate evaporated to dryness to give crude 10.38 (71 mg, 67%) as a viscous oil which is taken to the next step without purification.

Crude amine 10.38 (71 mg, 0.22 mmol), 2-butoxy-5-chlorobenzoic acid (49 mg, 0.22 mmol), EDC.HCl (50.2 mg, 0.26 mmol), HOBt (35.3 mg, 0.26 mmol) and TEA (26.4 mg, 0.26 mmol) are dissolved in $CHCl_3$ (10 mL) and stirred overnight. The reaction mixture is washed with water (10 mL), 1 M HCl (2×10 mL) and brine (10 mL), dried over $Na_2SO_4$, filtered and evaporated to dryness to give the crude product. Purification by preparative TLC (eluent: 100% $CH_2Cl_2$) gives the t-butyl ester of compound 137 (18 mg, 12%) as an off-white solid. The t-butyl ester (18 mg, 0.033 mmol) is dissolved in 50% TFA in $CH_2Cl_2$ (5 mL), stirred for 12 h, and evaporated to dryness to give crude compound 137. After trituration with EtOAc and hexanes, the title compound 137 (3 mg, 19%) is isolated as an off-white solid.

Example 11
Synthesis of 4'-{(1S,2S)-2-[(2-butoxy-5-chloroben-zoyl)amino]cyclopropyl}-biphenyl-4-carboxylic acid (Compound 114)
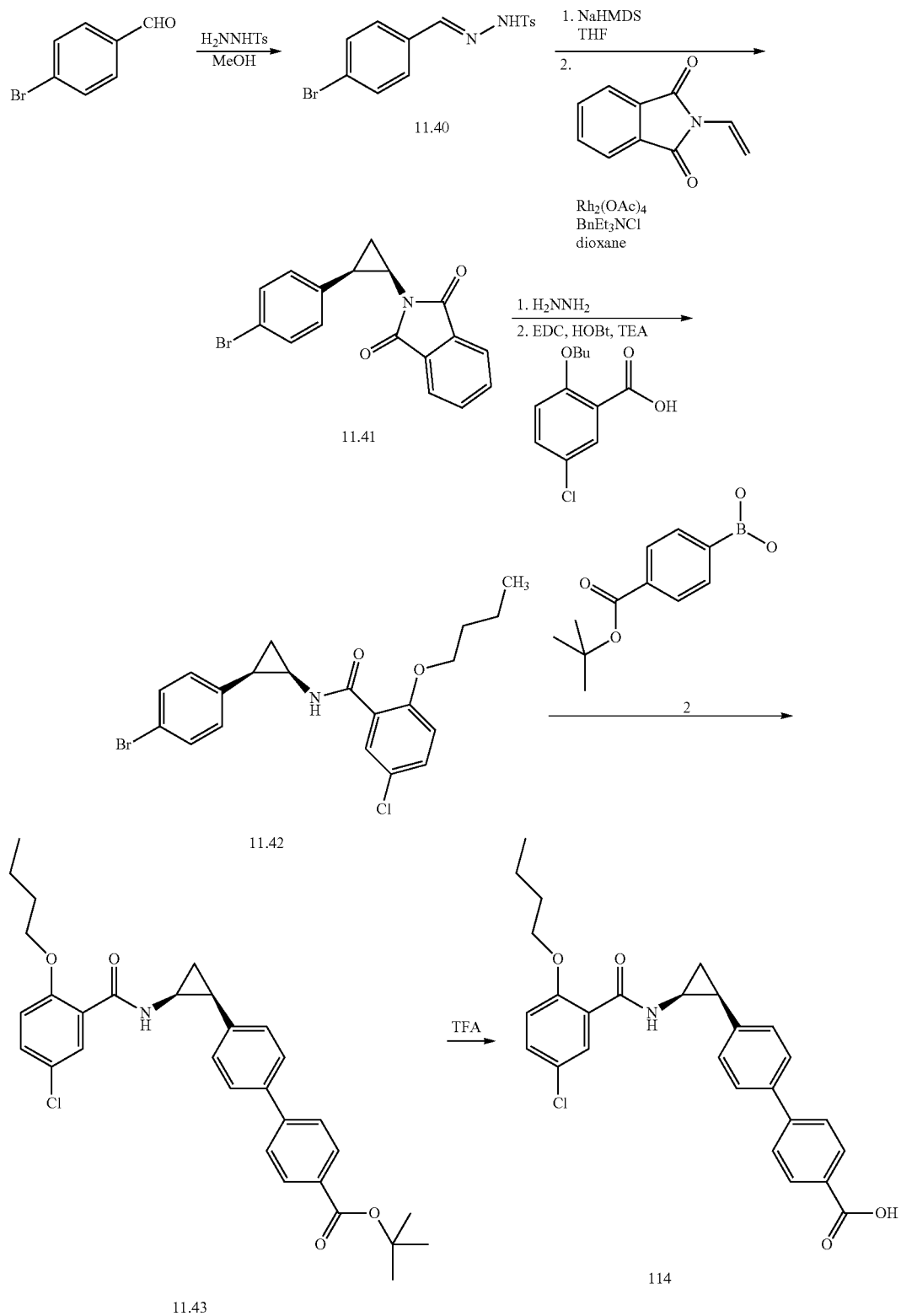

4-Bromobenzaldehyde (6.0 g, 32.4 mmol) is added in portions to a suspension of tosylhydrazide (6.93 g, 37.2 mmol) in MeOH (30 mL). The mixture is stirred for 1 h at room temperature then cooled to 0° C. and filtered. The white solid is washed with cold MeOH and dried to afford 11.40 (9.2 g, 80%).

A solution of the hydrazone 11.40 (2.5 g, 7.1 mmol) in anhydrous THF (60 mL) is cooled to −78° C. and 1 M sodium hexamethyldisilazane (7.1 mL, 7.1 mmol) is added. The mixture is maintained at −78° C. for 15 min then allowed to warm to room temperature. The solvent is removed under vacuum leaving a light yellow residue which is suspended in 1,4-dioxane (100 mL). To the suspension is added N-vinylphthalimide (7.3 g, 42.1 mmol), benzyltriethylammonium chloride (0.20 g, 0.88 mmol), and rhodium diacetate dimer (38 mg, 0.086 mmol). The resulting mixture is heated to 50° C. for 48 h. EtOAc (200 mL) is added and the mixture is washed with water (4×100 mL). The organic layer is separated, dried over $Na_2SO_4$, filtered and evaporated to dryness to give the crude solid that is purified by a flash silica gel chromatography (eluent: 10% EtOAc in hexanes) to give 11.41 (1.0 g, 40%) as a white solid.

A solution of hydrazine monohydrate (52.6 mg, 1.1 mmol) in ethanol (5 mL) is added to a suspension of cis-4-bromophenyl-cyclopropyl phthalimide 11.41 (0.30 g, 0.88 mmol) in ethanol (10 mL). After stirring for 15 h at 40° C., the reaction mixture is filtered and the filtrate evaporated leaving a viscous oil. To the oil is added 2-butoxy-5-chlorobenzoic acid (0.20 g, 0.88 mmol), EDC.HCl (0.20 g, 1.1 mmol), HOBt (0.14 g, 1.1 mmol) and TEA (0.11 g, 1.1 mmol). The mixture is dissolved in $CHCl_3$ (10 mL) and stirred overnight. The reaction mixture is washed with water (10 mL), 2 M HCl (2×10 mL), brine (10 mL), dried over $Na_2SO_4$, filtered and evaporated to dryness to give the crude product that is purified by flash silica gel chromatography (eluent: 10% EtOAc in hexanes). Evaporation of the solvents gives 11.42 (68 mg, 18%) as a white solid;

To a solution of compound 11.42 and boronic acid 11.2 (12 mg, 0.028 mmol) in DMF (0.5 mL) is added sodium carbonate solution (2M, 0.1 mL). The mixture is degassed using $N_2$ for 5 min before PdCl2(dppf).DCM (2 mg, 0.002 mmol) is added. The mixture is then heated at 70° C. overnight and concentrated. The residue is purified by prep-TLC (33% E-H) to give 12 mg of 11.43 as white solid.

To a solution of 11.43 (10 mg, 0.019 mmol) in THF (0.5 mL) is added 10% KOH solution (0.1 mL). The mixture is heated at 50° C. overnight and concentrated. The residue is suspended in 2 mL of water and acidified with solid citric acid to pH ~5. The precipitate is collected by centrifugation, washed with water (2×1 mL), dried under vacuum to give 6 mg title compound 114 as white solid.

Example 12

Synthesis of 4'-{(1R,2S)-2-[(2-butoxy-5-chlorobenzoyl)amino]-cyclopropyl}biphenyl-4-carboxylic acid (Compound 108)

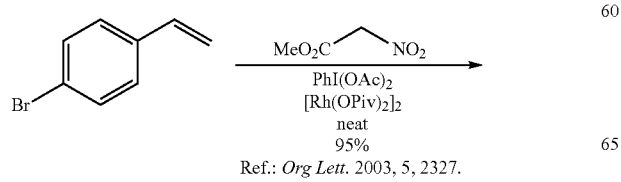

Ref.: Org Lett. 2003, 5, 2327.

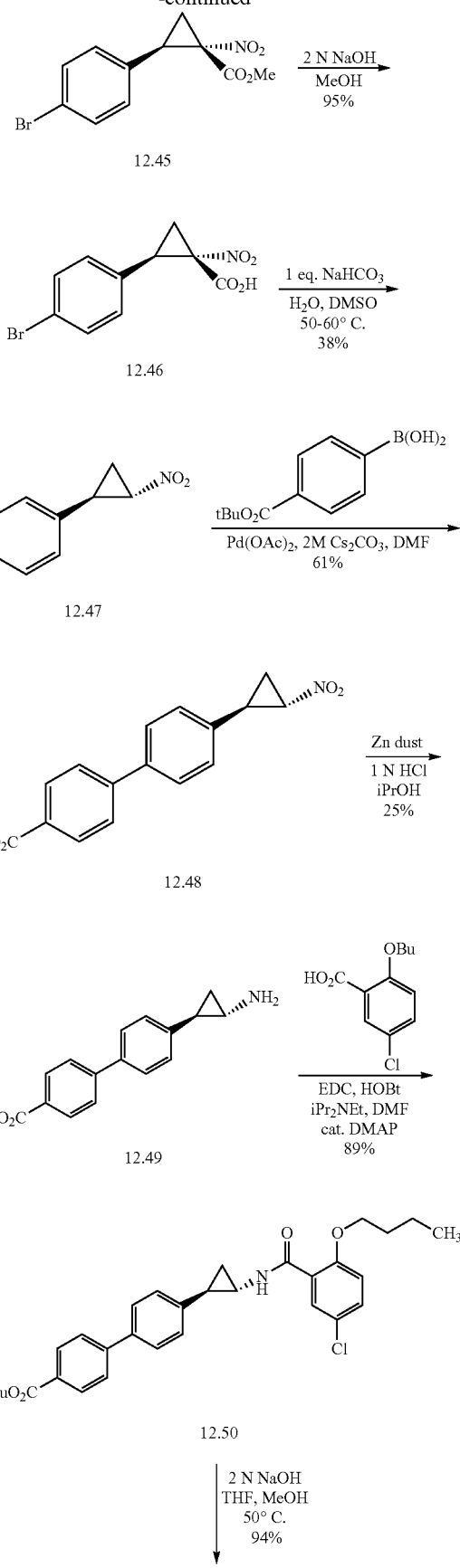

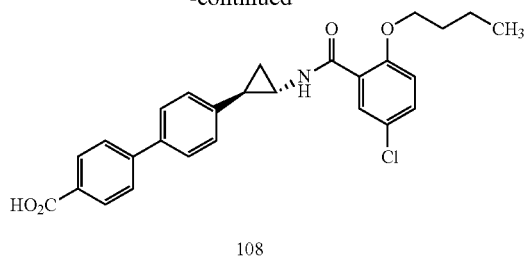

108

To a mixture of 4-bromostyrene (5.75 g, 31.4 mmol) and rhodium (II) trimethylacetate dimer (47 mg, 0.077 mmol) is added methyl nitroacetate (934 mg, 7.85 mmol) followed by iodobenzene diacetate (3.43 g, 10.65 mmol). After stirring at room temperature for 48 h, the crude mixture is applied directly to a silica gel column and flash chromatographed (hexanes to 93:7 hexanes/ethyl acetate) to afford 12.45 (2.24 g, 95%) as a colorless oil.

To a solution of ester 12.45 (900 mg, 2.87 mmol) in methanol (30 mL) is added 2 N NaOH (6 mL). After stirring overnight at room temperature, TLC analysis indicates complete consumption of the starting material. The solvent is removed at reduced pressure, and the residue is diluted with water and acidified to pH 2 with concentrated hydrochloric acid. The mixture is extracted with ethyl acetate (3×50 mL) and the combined extracts are washed with brine, dried over sodium sulfate, filtered, and concentrated at reduced pressure to afford 12.46 (775 mg, 95%) as a white foam.

A solution of acid 12.46 (2.40 g, 8.39 mmol) and sodium bicarbonate (705 mg, 8.39 mmol) in DMSO (40 mL) and water (4 mL) is heated to 60° C. for 30 min The mixture is cooled, acidified with 1 N HCl, and extracted with ethyl acetate (3×50 mL). The extracts are combined, washed with brine (5×100 mL), dried over sodium sulfate, filtered, and concentrated at reduced pressure. The residue is flash chromatographed (silica gel, hexanes to 95:5 hexanes/ethyl acetate) to afford trans-12.47 (770 mg, 38%) as an oil.

A 2 M cesium carbonate solution (1.75 mL) is added to a solution of nitrocyclopropane trans-12.47 (345 mg, 1.43 mmol) and 4-(tert-butoxycarbonyl)phenyl boronic acid (290 mg, 1.31 mmol) in DMF (10 mL). The mixture is degassed with three evacuation and argon backfill cycles. Palladium acetate (30 mg, 0.13 mmol) is added, and the solution is degassed again and heated to 80° C. After 5 h, the mixture is cooled. Ethyl acetate and 1 N HCl are added, and the mixture is filtered through diatomaceous earth. The filtrate layers are separated, and the aqueous layer is extracted with ethyl acetate (2×30 mL). The organic layers are combined, washed with brine, dried over sodium sulfate, filtered, and concentrated at reduced pressure. The residue is flash chromatographed (Biotage 12 M silica cartridge, hexanes to 92:8 hexanes/ethyl acetate) to afford 12.48 (270 mg, 61%) as a white solid.

Zinc dust (700 mg, 10.71 mmol) is added in portions over 10 min to a suspension of nitrocyclopropane 12.48 (180 mg, 0.53 mmol) in 2-propanol (11 mL) and 1 N HCl (5.4 mL). After stirring at room temperature for 45 min, saturated sodium bicarbonate is added, and the mixture is filtered through diatomaceous earth. The filter cake is rinsed thoroughly with ethyl acetate, and the filtrate layers are separated. The aqueous layer is extracted with ethyl acetate (2×30 mL), and the organic layers are combined, washed with brine, dried over sodium sulfate, filtered, and concentrated at reduced pressure. The residue is flash chromatographed (silica gel, dichloromethane to 99:1 dichloromethane/10% conc. ammonium hydroxide in methanol) to afford 12.49 (41 mg, 25%) as a white solid.

EDC (83 mg, 0.43 mmol), HOBt (60 mg, 0.44 mmol), Hunig's base (86 mg, 0.66 mmol) and DMAP (3 mg, 0.024 mmol) are added to a stirred solution of amine 49 (68 mg, 0.22 mmol) and 2-butoxy-5-chlorobenoic acid (86 mg, 0.38 mmol) in DMF (2 mL). After stirring overnight at room temperature, ethyl acetate and water are added. The layers are separated, and the aqueous layer is extracted with ethyl acetate (2×20 mL). The organic extracts are combined, washed with brine (5×20 mL), dried over sodium sulfate, filtered, and concentrated at reduced pressure. The residue is flash chromatographed (hexanes to 93:7 hexanes/ethyl acetate) to afford amide 12.50 (101 mg, 89%) as a foam.

A 2 N NaOH solution (3 mL) is added to a solution of amide 12.50 (80 mg, 0.15 mmol) in methanol (5 mL) and THF (5 mL). After stirring overnight at 50° C., the solution is cooled and the volatiles are removed at reduced pressure. The residue is diluted with water, and acidified to pH 3 with 1 N HCl. The resulting white solid is isolated by filtration and dried at reduced pressure to afford the title compound 108 (67 mg, 94%); mp 218-222° C.

Example 13

Synthesis of 2-{4'-[2-(2-butoxy-5-chloro-benzoylamino)-ethyl]-3'-ethyl-biphenyl-4-yloxy}-2-methylpropionic acid (Compound 158)

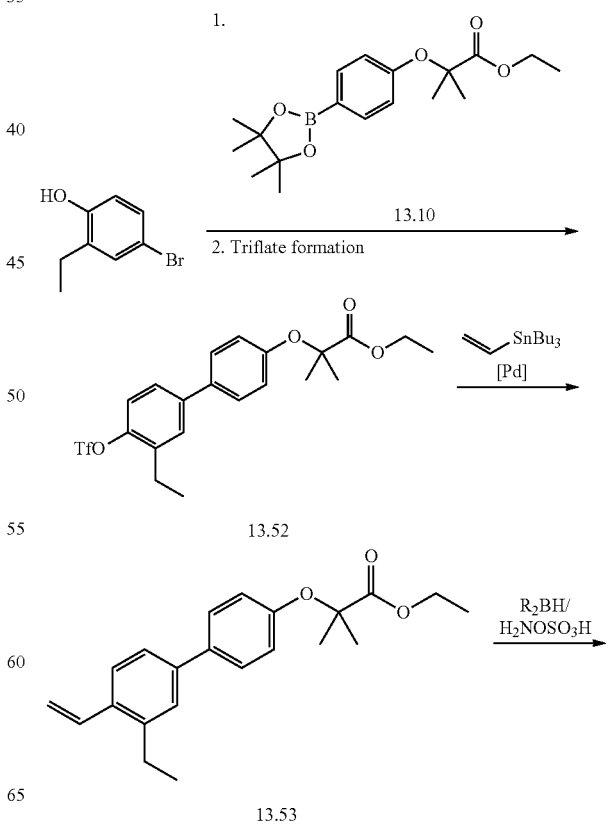

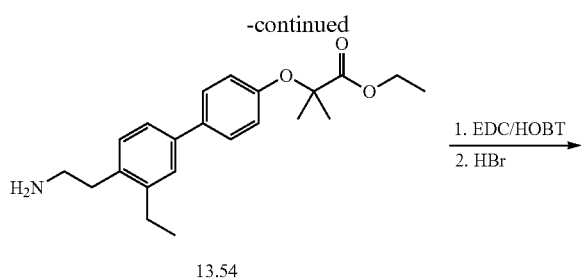

13.54

158

To a solution of 4-bromo-2-ethylphenol (535 mg, 2.66 mmol) and boronic ester 13.10 (750 mg, 2.24 mmol) in DMF (7 mL) is added PdCl$_2$(dppf)CH$_2$Cl$_2$ (46 mg, 0.021 mmol) then Na$_2$CO$_3$ solution (2M, 3 mL). The mixture is degassed using Ar stream for 10 min, sealed under Ar and then heated at 80° C. overnight. The mixture is concentrated. The residue is suspended in 10% citric acid and extracted with EtOAc. The organic layer is dried with Na$_2$SO$_4$, concentrated, and purified by SGC to give 545 mg of cross coupling product.

The product above (470 mg, 1.43 mmol) is dissolved in dioxane. To this solution is added Hunig's base (41 microL, 0.23 mmol) and PhNTf$_2$ (614 mg, 1.74 mmol). The mixture is stirred at 60° C. for 24 hours and concentrate. The residue is purified by SGC to give 560 mg of product 13.52 as a white solid.

A mixture of compound 52 (257 mg, 0.56 mmol), dry LiCl (54 mg, 1.27 mmol) and bis(triphenylphosphine)palladium (II) chloride (20 mg, 0.028 mmol) in 1 mL of dry DMF is degassed with Ar for 10 min before tributyltin (265 mg, 0.84 mmol) is added. The mixture is degassed 5 min more and sealed in a vial under Ar. The mixture is heated at 90° C. for 6 hours. After removal of DMF, the residue is purified by SGC using 0-10% E-H to give 72 mg of colorless oil (compound 13.53, yield 68%).

To a solution of compound 13.53 (100 mg, 0.3 mmol) in THF (0.2 mL) is added catecholborane (1M, 350 microL, 0.35 mmol) then tris(triphenylphosphine)rhodium(I) chloride (3 mg, 0.030 mmol) under Ar. The mixture is stirred at room temperature for 14 hours. To this mixture, MeOH (1 mL) is carefully added at 0° C. Hydroxylamine sulfonic acid (260 mg, 2.3 mmol) is added next followed by NaOH (2M, 0.3 mL). The mixture is stirred at 25° C. for 24 hours. LC-MS shows a major product peak (ES+ 339). The mixture is cooled to 0° C., adjusted to pH ~4, and filtered. The filtrate is purified directly by reverse phase HPLC to give 35 mg of compound 13.54 as yellowish oil.

To a solution of 5-chloro-2-butoxyoxy-benzoic acid (20 mg, 0.087 mmol) in DMF (0.2 mL) is added HOBT (12 mg, 0.087 mmol) then EDC (17 mg, 0.087 mmol). The mixture is stirred at room temperature for 2 hours. To this mixture is then added compound 13.54 (19 mg, 0.053 mmol) followed by Hunig's base (46 microL, 0.262 mmol) and DMAP (2 mg, 0.016 mmol). The mixture is stirred at room temperature overnight and then heated at 50° C. for 2 hours. The mixture is concentrated and the residue purified by Prep-TLC using 30% E-H to give 26 mg of coupling product (ester), yield 53%.

To a solution of ester 13.54 (2 mg, 0.004 mmol) in 0.1 mL of acetic acid is added 0.1 mL of 48% HBr—H$_2$O solution. The mixture is stirred at room temperature for 18 h and concentrated. The residue is purified by Prep-TLC (silica gel) to give ~1 mg of the title compound 158.

Example 14

Synthesis of 2-[(4'-{2-[(5-chloro-2-methoxybenzoyl)amino]ethyl}-3'-fluorobiphenyl-4-yl)oxy]-2-methyl-propanoic acid (Compound 54)

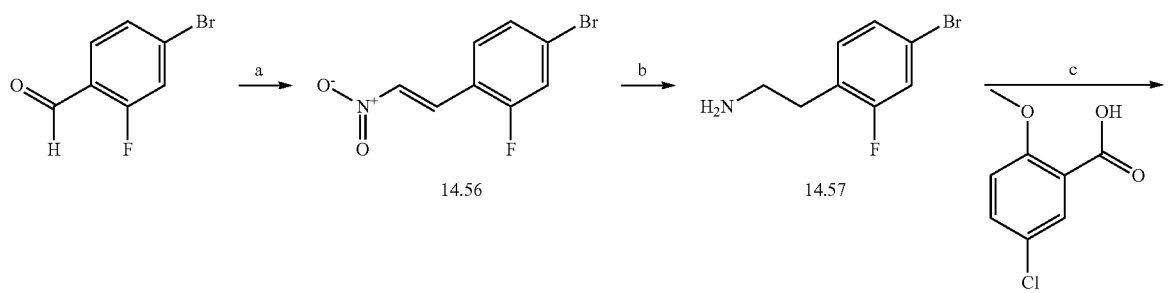

14.56      14.57

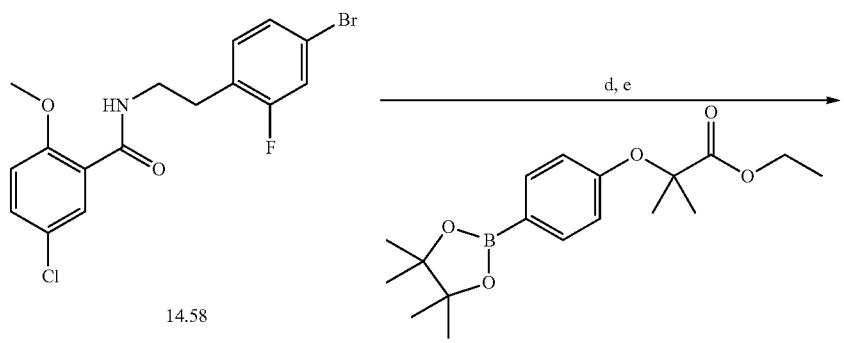

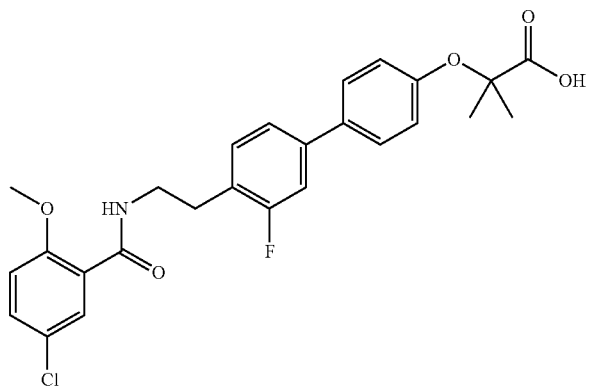

54

Reagents and Conditions: a) MeNO₂, NH₄Ac, HOAc, 110° C., 3 h; b) LiBH₄, TMSCl, 23° C., 24 h; c) EDC, HOBt, i-Pr₂NEt, DMF, 15 h; d) PdCl₂(dppf)CH₂Cl₂, 2 M aq. Na₂CO₃, DME, 85° C., 14 h; e) NaOH, THF-MeOH, 70° C., 2 h. (795-025).

A mixture of 4-bromo-2-fluorobenzaldehyde (4 g, 19.7 mmol), nitromethane (10 mL, 1643.8 mmol), and ammonium acetate (1.4 g, 23.0 mmol) in 6 mL HOAc is heated at 110° C. for 3 h. The reaction mixture is cooled down, diluted with water and extracted with EtOAc. The extract is washed with 2 M NaOH, sat. Na₂CO₃, brine, dried over Na₂SO₄, and concentrated in vacuo. The crude product is purified by chromatography to give the desired olefin 14.56 (3.7 g, 76%).

A solution of Me₃SiCl (1 M, 3 ml, 3 mmol) in THF is added to a solution of LiBH₄ (2 M, 0.7 ml, 1.4 mmol) in THF (5 mL) under Ar₂. After 5 min, 56 (180 mg, 0.73 mmol) is added in 2 mL THF and the mixture is stirred at 23° C. for 24 h. The reaction is carefully quenched by adding 10 mL of methanol at 0° C. After the solvents are removed in vacuo, the residue is diluted with CH₂Cl₂, washed with 0.5 M aq. NaOH, brine, dried over Na₂SO₄, and concentrated to give 150 mg of crude product 14.57 as a brown oil that is usable in the next step without further purification.

A mixture of 5-chloro-2-methoxybenzoic acid (100 mg, 0.54 mmol), the above amine (150 mg, 0.69 mmol), EDC (150 mg, 0.78 mmol), HOBt (110 mg, 0.81 mmol), Hunig's base (0.2 mL, 1.15 mmol) in 1 mL of DMF is stirred at 23° C. for 14 h. The reaction mixture is diluted with EtOAc, washed with water, brine, dried over Na₂SO₄, and concentrated in vacuo. The crude product is purified by chromatography to give the desired amide 14.58 (120 mg, 57% in 2 steps).

To a solution of the boronic acid pinacol ester (120 mg, 0.36 mmol) in DME (1 mL) is added 14.58 (120 mg, 0.31 mmol). The mixture is purged with Ar₂. PdCl₂(dppf)CH₂Cl₂ (25 mg, 0.031 mmol) is then added followed by an aq. solution of Na₂CO₃ (2 M, 0.31 mL, 0.62 mmol) under Ar₂. The reaction tube is then sealed and the reaction mixture is heated at 85° C. for 14 h. The reaction mixture is diluted with EtOAc, washed with water, brine, dried over Na₂SO₄, and concentrated in vacuo. The crude product is purified by chromatography eluting with 20-50% EtOAc in hexane to give the desired cross coupling product (85 mg, 53%).

To a solution of the above product (80 mg, 0.16 mmol) in 3 mL of 1:1 THF-MeOH is added aq. NaOH (2 M, 0.15 mL, 0.3 mmol). The mixture is heated at 70° C. for 2 h. After cooling down, the reaction mixture is diluted with water, acidified with 3 N HCl to pH 2-3, and extracted with EtOAc, washed with brine, dried over Na₂SO₄, and concentrated in vacuo to give the title compound 54 (65 mg, 86%).

Example 15
Synthesis of 2-(4-{5-[2-(2-butoxy-5-chloro-benzoylamino)-ethyl]-pyridin-2-yl}-phenoxy)-2-methyl-propionic acid (Compound 157)
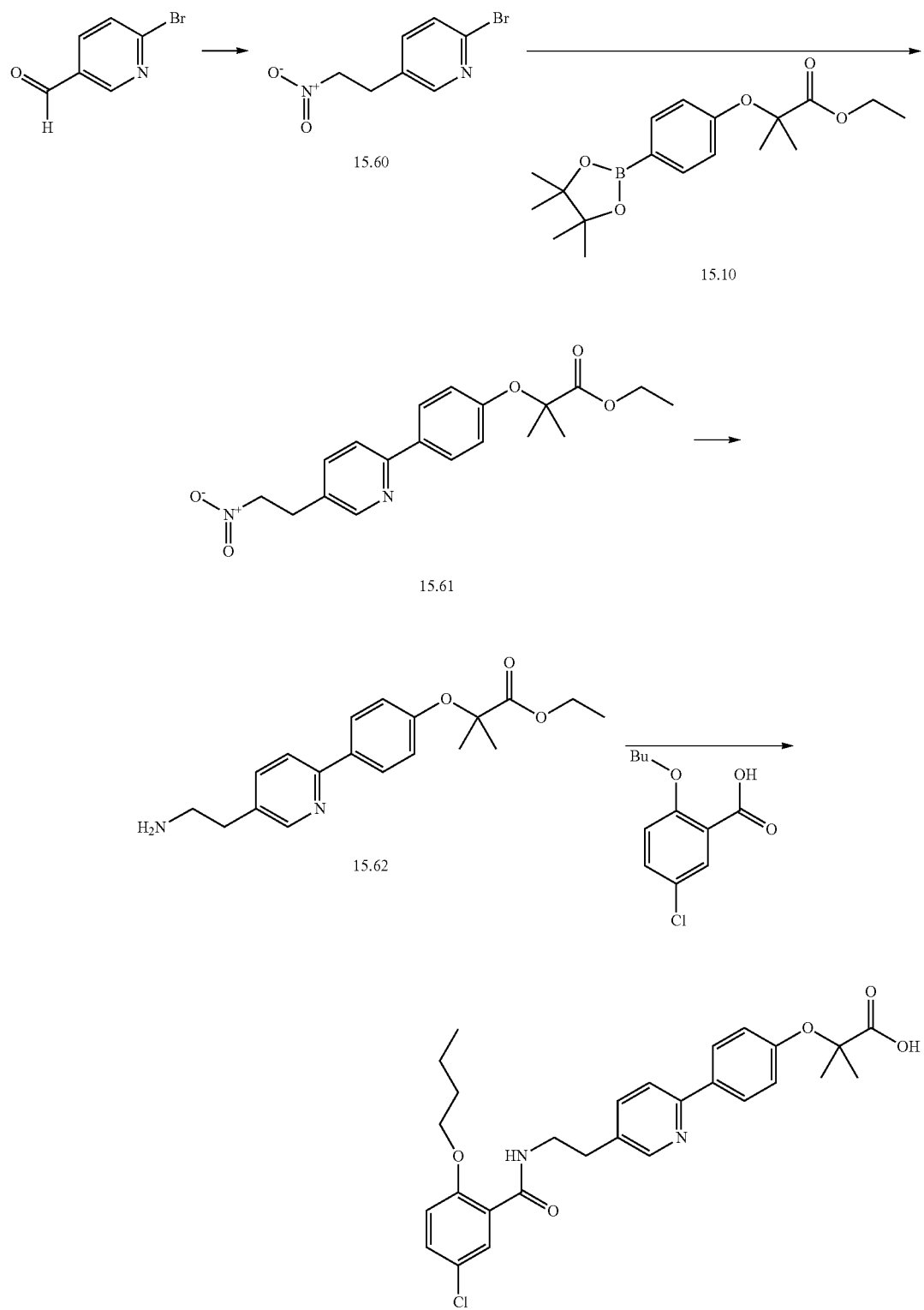

A mixture of 6-bromo-pyridine-3-carbaldehyde (2 g, 10.8 mmol), nitromethane (6 mL, 98.3 mmol) and ammonium acetate (0.8 g, 13.1 mmol) in 5 mL HOAc is heated at 100° C. for 3 h. The reaction mixture is cooled, the precipitates are collected by filtration, washed with ether, and dried to give the condensation product (1.5 g, 61%).

To a suspension of the above product (500 mg, 2.18 mmol) in 5 mL MeOH—$CH_2Cl_2$ (2:3) is added $NaBH_4$ (200 mg, 5.26 mmol) in portions at 0° C. and the resulting solution is stirred at 23° C. for 1 h. The reaction is then quenched by adding 10% $NH_4Cl$, diluted with EtOAc, washed with sat. aq. $NaHCO_3$, brine, dried over $Na_2SO_4$, and concentrated in vacuo to give the desired product 15.60 (450 mg, 89%) which is used in next step without any purification.

To a solution of the boronic acid pinacol ester 15.10 (200 mg, 0.60 mmol) in DMF (1 mL) is added the bromide 15.60 (130 mg, 0.56 mmol). The mixture is purged with $Ar_2$. $PdCl_2$(dppf)$CH_2Cl_2$ (50 mg, 0.062 mmol) is then added followed by an aq. solution of $Na_2CO_3$ (2 M, 0.6 mL, 1.2 mmol) under $Ar_2$. The reaction tube is then sealed and the reaction mixture is heated in a microwave reactor at 120° C. for 30 min. The reaction mixture is diluted with EtOAc, washed with water, brine, dried over $Na_2SO_4$, and concentrated in vacuo. The crude product is purified by chromatography eluting with 40-80% EtOAc in hexane to give the desired product 15.61 (25 mg, 12%).

To a solution of the above nitro compound 15.61 (25 mg, 0.07 mmol) in 1 mL of EtOH is added 10% Pd—C (10 mg), and the mixture is stirred under one atmosphere $H_2$ gas for 2 days. The reaction mixture is filtered through a pad of diatomaceous earth, and the solid residue is rinsed with $CH_2Cl_2$. The filtrate is concentrated in vacuo to give 25 mg of crude product 15.62, which is used in next step.

A mixture of 5-chloro-2-n-butoxybenzoic acid (16 mg, 0.07 mmol), amine 62 (25 mg, 0.07 mmol), EDC (30 mg, 0.16 mmol), HOBt (20 mg, 0.15 mmol), Hunig's base (0.03 mL, 0.17 mmol) in 1 mL of DMF is stirred at 23° C. for 14 h. The reaction mixture is diluted with EtOAc, washed with water, brine, dried over $Na_2SO_4$, and concentrated in vacuo. The crude product is purified by chromatography to give the desired amide (15 mg, 40% in 2 steps).

To a solution of the above product (15 mg, 0.028 mmol) in 2 mL of 1:1 THF-MeOH is added aq. NaOH (1 M, 0.1 mL, 0.1 mmol). The mixture is heated at 70° C. for 3 h. After cooling down, the reaction mixture is diluted with water, acidified with 3 M HCl to pH ~4, and extracted with EtOAc, washed with brine, dried over $Na_2SO_4$, and concentrated in vacuo. The crude product is purified by preparative HPLC to give the title compound 157 (11 mg, 63%) as the TFA salt.

Example 16

Synthesis of 4'-{2-[(2-butoxy-5-chlorobenzoyl)amino]ethyl}-3-chlorobiphenyl-4-carboxylic acid (Compound 11)

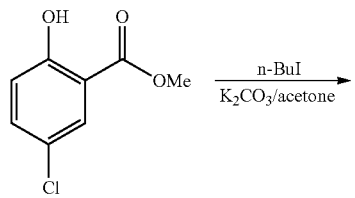

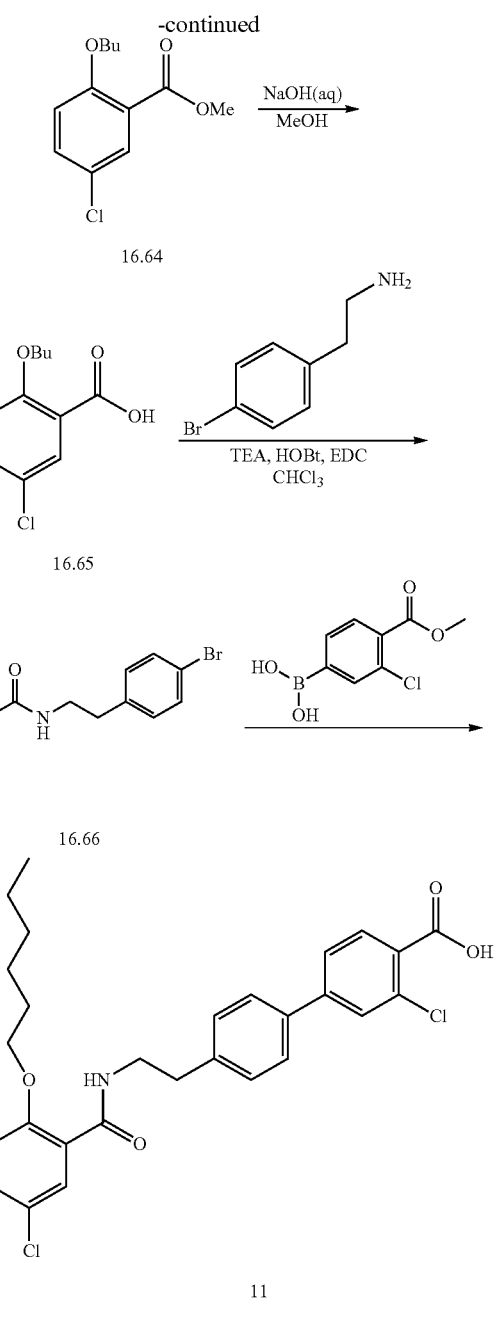

To a 1.0 L, round-bottomed flask are added methyl 5-chlorosalicylate (21.3 g, 0.114 mol), $K_2CO_3$ (18.0 g, 0.131 mol) and iodobutane (24.0 g, 0.131 mol). Acetone (400 mL) is added to the flask and its contents are heated to reflux for 16 h. The reaction mixture is cooled to room temperature and filtered. The filtrate is evaporated to dryness leaving a gummy solid that is redissolved in EtOAc, washed with saturated $NH_4Cl$ solution, dried over $Na_2SO_4$, filtered and evaporated to dryness to give 16.64 (25.3 g, 91%) as a white sticky solid.

A solution of NaOH (8.3 g, 0.21 mol) in water (100 mL) is added to a solution of methyl 2-butoxy-5-chlorobenzoate 16.64 (23.5 g, 0.10 mol) in MeOH (70 mL) and the resulting mixture is stirred at room temperature for 4 h. After evaporation of most of the solvent, the resulting suspension is diluted with water (150 mL), acidified to pH 2 with conc. HCl and extracted with EtOAc. The organic layer is separated, dried over $Na_2SO_4$, filtered and evaporated to dryness to give 16.65 (18.2 g, 79%) as an off-white solid.

2-Butoxy-5-chlorobenzoic acid 65 (13.0 g, 57.0 mmol), 4-bromophenethylamine (11.4 g, 57.0 mmol), EDC.HCl (13.1 g, 68.4 mmol), HOBt (9.2 g, 68.4 mmol) and TEA (6.9 g, 68.4 mmol) are dissolved in $CHCl_3$ and stirred overnight. The reaction mixture is washed with water (250 mL), 1 M HCl (3×250 mL), and brine (200 mL), dried over $Na_2SO_4$, filtered and evaporated to dryness to give the crude product. Purification by a flash silica gel column chromatography (eluent: 15% EtOAc in hexanes) gives 16.66 (17.0 g, 73%) as a white solid.

To a solution of the bromide 16.66 (100 mg, 0.243 mmol) and (4-methoxycarbonyl 3-chlorophenyl) boronic acid (57.2 mg, 0.267 mmol) in 2 mL of DMF is added an aq. $Na_2CO_3$ solution (2 M, 243 microL, 0.486 mmol). The mixture is purged with $Ar_2$ for 10 min $PdCl_2(dppf)CH_2Cl_2$ (9.7 mg, 0.012 mmol) is then added. The reaction is stirred under $Ar_2$ at 85° C. for 18 h. The resulting coupled product ester is hydrolyzed in situ with the addition of 243 microL of 2M $Na_2CO_3$ solution and heating at 120° C. After cooling down, the reaction mixture is extracted with EtOAc, and washed with water, brine. The organic layer is separated and dried over $MgSO_4$ and concentrated in vacuo. Purification of the crude product by reverse phase HPLC gives the title compound 11 (25 mg, 21%).

Example 17

Synthesis of 2-[(4'-{2-[(2-butoxy-5-chlorobenzoyl)amino]ethyl}-3-fluorobiphenyl-4-yl)oxy]-2-methyl-propanoic acid (Compound 4)

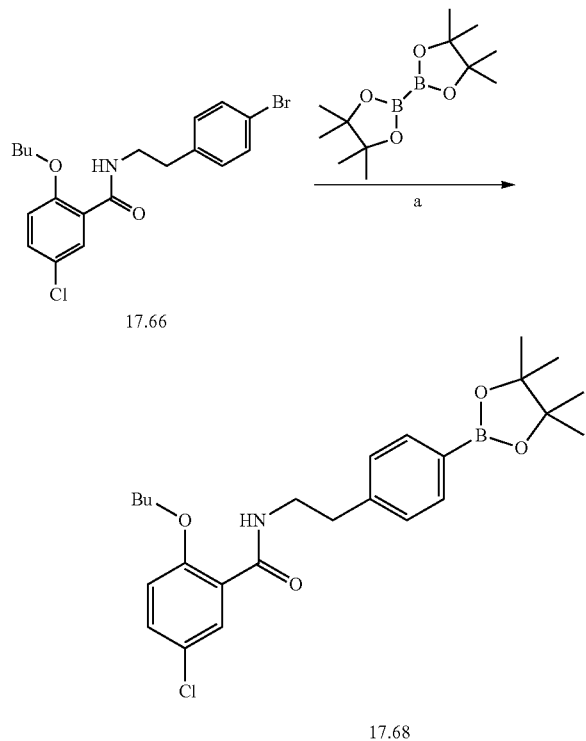

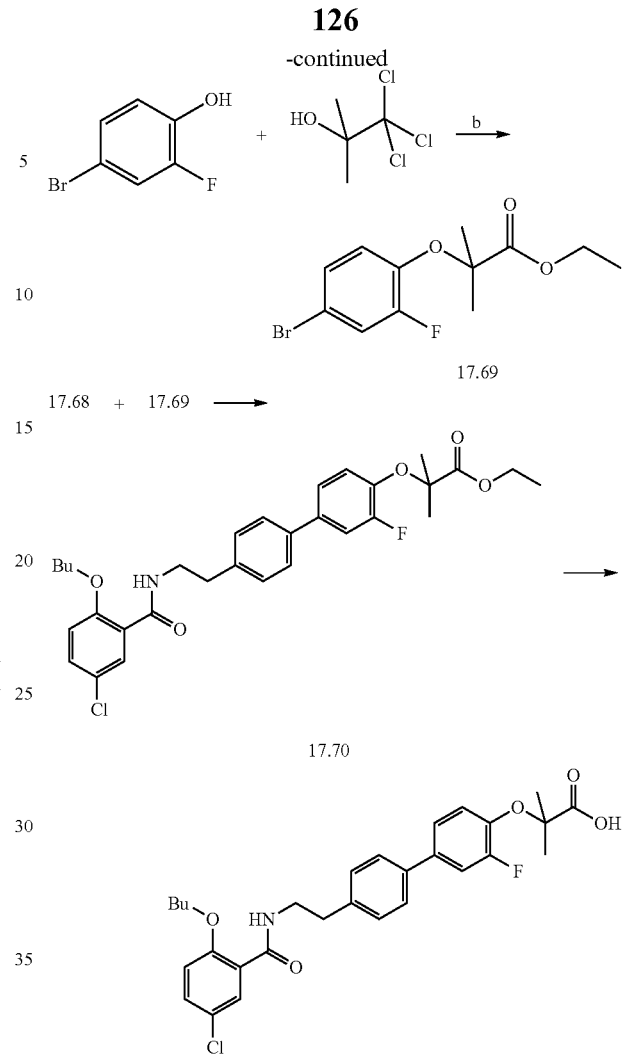

To a solution of the bromide 17.66 (2.0 g, 4.869 mmol) and Bis(pinacolato)diboron (1.35 g, 5.34 mmol) in 16 mL of anhydrous DMSO is added KOAc (954 mg, 9.72 mmol). The mixture is purged with $Ar_2$ for 10 min $PdCl_2(dppf)CH_2Cl_2$ (195 mg, 0.24 mmol) is then added. The reaction is stirred under $Ar_2$ at 120° C. for 18 h. After cooling down, the reaction mixture is extracted with EtOAc, and washed with water and brine. The organic layer is separated and dried over $MgSO_4$ and concentrated in vacuo. Purification of the crude product chromatography gives the desired product 17.68 (1.68 g, 75.4%).

To a solution of 4-bromo-2-fluorophenol (921 mg, 4.82 mmol) and 1,1,1-trichloro-2-methyl-2-propanol hemihydrate (1.711 g, 9.64 mmol) in acetone (23 ml) is added NaOH (1.542 g, 38.56 mmol) and the mixture is stirred at room temperature for 16 h. After solvent is removed under reduced pressure, the residue is dissolved in water and washed with ether. The aqueous layer is acidified with concentrated HCl and extracted with ether. The extracts are washed twice with brine, dried over anhydrous $MgSO_4$, and the solvent is removed under reduced pressure to give crude acid product as a waxy solid.

The residue is dissolved in EtOH (23 mL) and $SOCl_2$ (399 microL, 4.82 mmol) and is carefully added drop-wise to the stirred solution at room temperature. The mixture is heated under reflux for 6 h. After the reaction mixture is concentrated under reduced pressure, the residue is dissolved in ether and washed with water, saturated aqueous NaHCO$_3$, and brine successively. The organic layer is dried over anhydrous MgSO$_4$ and concentrated under reduced pressure. The crude product is purified by a chromatography (eluted with hexane to 30% EtOAc/hexane) to give the desired product 17.69 as a colorless oil (1.05 g, 71.4% in two steps).

To a solution of the boronic acid pinacol ester 17.68 (100 mg, 0.218 mmol) in DME (2 mL) is added the bromide 17.69 (80.5 mg, 0.264 mmol). The mixture is purged with Ar$_2$. PdCl$_2$(dppf)CH$_2$Cl$_2$ (9.75 mg, 0.012 mmol) is then added followed by an aq. solution of Na$_2$CO$_3$ (2 M, 272 microL, 0.545 mmol) under Ar$_2$. The reaction tube is then sealed and the reaction mixture is heated at 120° C. for 7 h. After cooling down, the reaction mixture is diluted with EtOAc, washed with water, brine, dried over MgSO$_4$, and concentrated in vacuo. The crude ester product is passed through a short silica column to give 17.70 as yellowish oil which is used for the saponification step without further purification.

To a solution of the above ester 17.70 (122 mg, 0.219 mmol) in 1 mL of THF-EtOH (1:1 v/v) is added aq. NaOH (2 M, 219 microL, 0.438 mmol). The mixture is stirred at room temperature overnight. The reaction mixture is acidified with 3 N HCl to pH 2-3 and diluted with 1.5 mL of water-MeCN-DMSO (1:1:1). The crude product is obtained by filtration and is purified by reverse phase HPLC to provide the title compound 4 as a colorless oil (69 mg, 60% in two steps).

Example 18

Synthesis of 2-{3,5'-Dichloro-4'-[2-(5-chloro-2-methoxy-benzoylamino)-ethyl]-biphenyl-4-yloxy}-2-methyl-propionic acid (Compound 159)

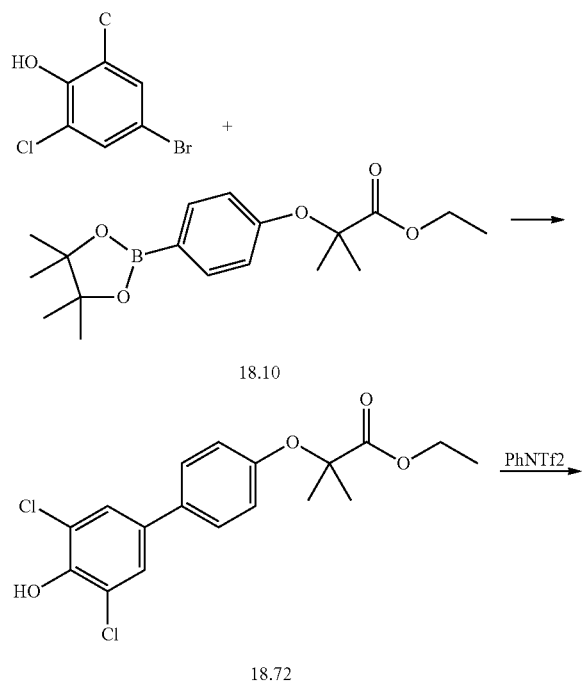

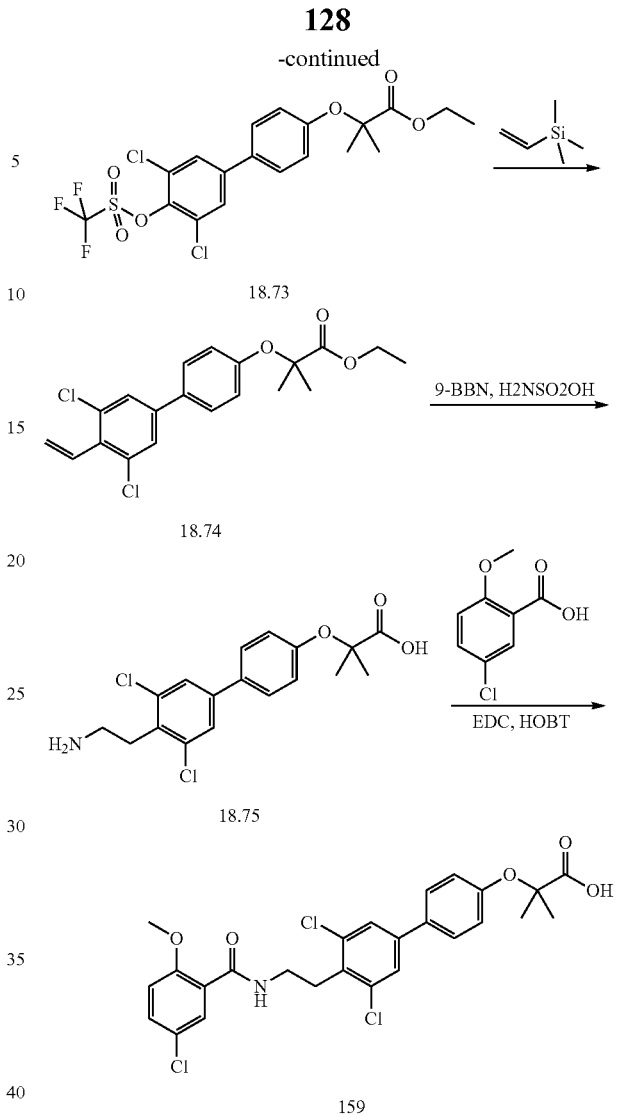

A solution of 4-bromo-2,6-dichlorophenol (270 mg, 1.12 mmol), boronic ester 18.10 (373 mg, 1.12 mmol), PdCl$_2$(dppf)CH$_2$Cl$_2$ (90 mg, 0.112 mmol) in DMF (10 mL) is degassed with an Ar stream for 10 min before Na$_2$CO$_3$ (2M solution) is added. The mixture is sealed under Ar and heated at 70° C. for 16 h and concentrated. The residue is suspended in 10% citric acid and then extracted with EtOAc. The organic layer is dried with Na$_2$SO$_4$, concentrated, and purified by SGC (0-30% E-H gradient) to give 320 mg product 18.72.

To a solution of 18.72 (300 mg, 0.812 mmol) in dioxane (3 mL) is added diisopropylethylamine (218 micrL, 1.22 mmol) followed by N-phenyl trifluoromethanesulfonimide (348 mg, 0.975 mmol.). The mixture is heated at 50° C. for 16 h. The mixture is concentrated and purified by SGC Biotag, 5% EtOAc-hexane to yield 80 mg desired product 18.73 as white needle-like crystals.

To a flask containing dry LiCl (20 mg, 0.472 mmol) and palladium acetate (12 mg, 0.055 mmol) is added a solution of the triflate 18.73 (138 mg, 0.275 mmol) in DMF (1.5 mL). The mixture is degassed using an Ar stream for 10 min before vinyltrimethylsilane (200 microL, 1.3 mmol) and) triethyl amine (200 microL, 1.4 mmol) are added. The mixture is then sealed and heated at 55° C. for 20 hr. DMF is removed. The residue is taken up in dichloromethane and purified by SGC using 10% E-H to give 96 mg desired product 18.74.

To a solution of the olefin 18.74 (72 mg, 0.19 mmol) in THF (0.2 mL) is added 9-BBN (0.5 M, 0.57 mL, 0.285 mmol) under Ar. The mixture is heated at 50° C. overnight and then cooled to room temperature and concentrated. The residue is re-dissolved in DME (0.4 mL) and treated with hydroxyaminesulfonic acid (96 mg, 0.85 mmol). The mixture is then heated under Ar at 100° C. for 5 hours. After cooling to room temperature, MeOH (0.5 mL) is added followed by 2M Na2CO3 (0.5 mL). The mixture is next stirred at room temperature overnight and then acidified to pH 2 using 2N HCl. The mixture is then extracted with EtOAc, dried ($Na_2SO_4$) and concentrated. Purification of the residue by reverse phase HPLC gives 16 mg of amine 18.75.

To a solution of 5-chloro-2-methoxy-benzoic acid (7 mg, 0.038 mmol) in DMF (0.2 mL) is added HOBT (10 mg, 0.074 mmol) and EDC (7 mg, 0.037 mmol). The mixture is stirred at room temperature for 2 hours before a solution of amine 18.75 (5 mg, 0.014 mmol) in DMF (50 microL) and 4-(N,N-dimethylamino)pyridine (catalytic amount) are added. The mixture is stirred at room temperature for 24 h and concentrated. The residue is purified by reverse phase HPLC using 30-100% $CH_3CN$—$H_2O$ w/0.1% TFA to give 2 mg of the title compound 159.

Procedures for Identification of CCR10 Antagonists

CCR10 FLIPR Assay

Preferred compounds have an $IC_{50}$ of 500 nM or lower in this assay.

Cell Media

To a 1 liter bottle of Hams F12 (Mediatech #10-080-CM) add 100 mL Fetal Bovine Serum (Mediatech #35-0,5-CV), 10 mL geneticin (Invitrogen #10131-027), and 2 mL Zeocin (Invitrogen #R250-05).

Cell Plating for Assay

CHO-K1 hCCR10 cells (Euroscreen cat #ES-143-A) are diluted in media to a final concentration of $2.8 \times 10^5$ cells/mL and 25 microL of this suspension are added to each well of a BD384 well TC treated assay plate (VWR #62406-490). This will yield approximately 7,000 cells/well. The plate is incubated at 37° C./5% $CO_2$ overnight.

EC50 Determination of CCR10 Peptide

The EC50 and EC70 should be calculated each time the assay is performed. CTACK/CCL27 (R&D Systems #376-CT; 30 microM stock) is diluted to a working concentration of 10 microM (2.5 microM final) in peptide buffer (HBSS/1 mM CaCl/1 mM $MgSO_4$ al % BSA). This is serially dilute 1:3 in the same buffer for a total of 11 concentrations of peptide. The assay below is run and the EC50 of the CCR10 peptide is calculated. Test compounds are assayed at the EC70.

CCR10 FLIPR Assay

Cell plates are removed from the incubator, inverted to "flick" out media and tapped dry on a paper towel. 25 microL 1×FLUO-4 dye/2 mM probenicid are added to each well. The plates are then incubated 30 minutes at 37° C./5% $CO_2$, then removed and incubated 30 additional minutes at room temperature. 5 microL diluted (see below) test compound (final concentration based on 30 microL) are added to appropriate wells. The wells are mixed and incubated at room temperature for 15 minutes. The plates are then placed on FLIPR and 10 microL CCR10 peptide (30 microM stock diluted to appropriate 4× of final concentration at EC70) from a Greiner 384 well polypropylene plate are transferred. Peptide should be in columns 1-22 and peptide dilution buffer should be in columns 23 and 24 for blanks.

Plate reader data are analyzed using ActivityBase software (ID Business Solutions, Ltd). The RFU signals from the plate reader are converted to percent of control (POC) values using the formula:

$$POC=100*(Signal-BCTRL)\div(PCTRL-BCTRL)$$

Where Signal is the test well signal, BCTRL is the average of background (negative control) well signals on the plate and PCTRL is the average of positive control well signals on the plate.

For the concentration responsive compounds, POC as a function of test compound concentration are fitted to a 4-parameter logistic equation of the form:

$$Y=A+(B-A)/[1+(x/C)^D]$$

Where A, B, C, and D are fitted parameters (parameter B is fixed at zero POC), and x and y are the independent and dependent variables, respectively. The $IC_{50}$ (50% inhibitory concentration) is determined as the inflection point parameter, C.

Compound Preparation

Compound powders are diluted in vials to 10 mM in 100% DMSO. 9.7 microL 10 mM stock are added to 80 microL 100% DMSO in column 1 of a 96 well plate. 60 microL 100% DMSO are added to remaining wells. The compound is serially dilute compound by adding 30 microL column 1 to 60 microL in column 2. Column 2 is mixed dilution is continued across the 96 well plate ending at column 10. This step is done on the Beckman FX with no tip change between columns. 16 compounds or 2×96 well plates can be tested in 1×384 well plate. Each 96 well plate is transferred to 1×384 well plate. Columns 21 through 24 on the 384 well plate contain DMSO vehicle control only. Just prior to the assay 5 microL of compound from the 384 well plate is transferred to another 384 well plate containing 40 microL 1×HBSS/1 mM CaCl/1 mM $MgSO_4$. This is mixed 5 microL of the diluted compound is transferred to the appropriate wells of the cell assay plate for the FLIPR assay, above.

Reagents

1× Assay Buffer

1×HBSS (10×, Invitrogen #14185-027), 10 mM HEPES pH 7.4, 0.35 g/L sodium bicarbonate, 1 mM $CaCl_2$, 1 mM $MgSO_4$ Fluo-4 Dye/2 mM Probenicid (Molecular Probes Fluo-4 Kit # F36206)

Resuspend dye in 100 mL 1× assay buffer and mix.

Resuspend 1 vial of probenicid with 1 mL 1× assay buffer and add to 100 mL bottle of dye Chemotaxis Assay Test compounds are evaluated for their ability to inhibit chemotaxis of Baf/3 cells expressing human CCR10 (hereinafter Baf/3-hCCR10 cells) in response to CCL27. Preferred compounds have IC50<1 micromolar in this assay.

Assay Protocol:

Test compounds are diluted (2× the final concentration) in CTX media (RPMI 1640 (Gibco-BRL #11875-093) supplemented with 0.1% BSA (Sigma #A3803)). Control solutions contain 1% DMSO in CTX media. Baf/3-hCCR10 cells are re-suspended in CTX media to a concentration of $4 \times 10^6$ cells/mL. In a 96 well plate, 100 microL the Baf/3-hCCR10 cell suspension is combined with 100 microL of the test compound solution and the plate is then incubated for 15 min at room temperature.

150 microL of a solution of the chemoattractant (2× the EC70 for CCL27) in CTX media is added to appropriate wells of a 96-well chemotaxis chamber (Neuro Probe Cat. #:116-5, Sum pore size, 5.7 mm diameter size, 300 microL, 96 well plate). CTX media without chemoattractant is added to control wells. 152 microL of 2× compound solution in CTX media is added to appropriate wells. The chamber is assembled according to manufacturer's instructions using the 5 micron pore size PVP-free polycarbonate filter. Care should be taken to avoid bubbles as they will cause variation.

80 microL of the cells plus compound incubation mixture is added to upper wells of the chamber. Care is taken to avoid forming bubbles at the level of the filter. The chamber is then incubated at 37° C. for 3 hours.

The chamber is then disassembled and the filter is removed. 150 microL of media is gently removed from each well of the chemotaxis chamber. The remaining 150 microL is then mixed and 100 microL of the resulting cell suspension is transferred into a 96 well Costar 3917 assay plate (Corning incorporated, cat #3917).

The cells are measured using a CyQUANT® NF Cell Proliferation Assay (Invitrogen, cat #C35006). 11 mL of 1×HBSS buffer is prepared by diluting 2.2 mL of 5×HBSS buffer (Component C) with 8.8 mL of deionized water. 1× dye binding solution is prepared by adding 22 microL of CyQUANT® NF dye reagent (Component A) and 22 microL of Component C to 11 mL of 1×HBSS buffer. 100 microL of 1× dye binding solution is dispensed into wells of the 96 well Costar plate containing the cell suspensions. The plate is covered and incubated at 37° C. for 60 minutes. Fluorescence measurement is quantitated using a multilabel plate reader (Wallac Victor2).

Methods of Therapeutic Use

In accordance with the invention, there are provided novel methods of using the compounds of the present invention. The compounds disclosed herein effectively block the interaction of CCR10 with its ligand CCL 27. The inhibition of this interaction is an attractive means for preventing and treating a variety of diseases or conditions associated with entry and activation of T-cells into the skin or other tissues where CCR10 is found to be expressed and associated with inflammatory conditions, such as lung tissue. Thus, the compounds of the present invention are useful for the treatment of diseases and conditions including psoriasis, contact sensitivity, dermatitis, systemic sclerosis, cutaneous systemic lupus erythematosus, and allergic asthma. The compounds of the invention will also be useful for treatment of melanomas that express CCR10.

These disorders have been well characterized in man, but also exist with a similar etiology in other mammals, and can be treated by pharmaceutical compositions of the present invention.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)).

The compounds may be administered alone or in combination with adjuvants that enhance the stability of the inhibitors, facilitate administration of pharmaceutical compositions containing them in certain embodiments, provide increased dissolution or dispersion, increase inhibitory activity, provide adjunct therapy, and the like. Advantageously, such combinations may utilize lower dosages of the active ingredient, thus reducing possible toxicity and adverse side effects. Carriers and adjuvants for use with compounds according to the present invention include, for example, ion exchangers, alumina, aluminum stearate, lecithin, serum proteins, buffer substances, water, salts or electrolytes and cellulose-based substances.

What is claimed is:

1. A compound of formula (I):

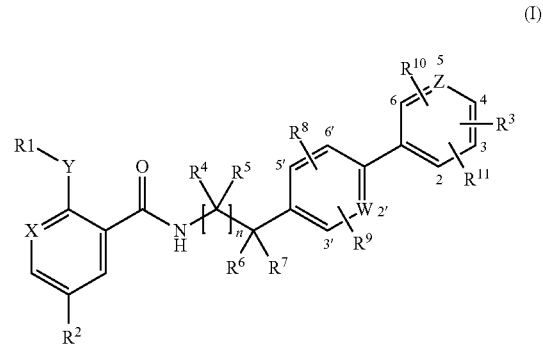

wherein:
W, X, and Z are C;
Y is O, NH, or S;
n is 1;
$R^1$ is
   (a) H;
   (b) $C_{1-8}$alkyl, branched or unbranched, optionally partially or fully halogenated, and optionally substituted with one to two groups selected from —OH, CN, $C_{1-6}$alkoxy, —$CO_2C_{1-6}$alkyl, and —$CON(C_{1-3}$alkyl)($C_{1-3}$alkyl),
   (c) —$(CH_2)_{0-1}C_{3-8}$cycloalkyl,
   (d) —$CH_2$Ar, wherein Ar is phenyl or heteroaryl selected from pyridinyl, triazolyl, pyrimidinyl, furanyl, thiazolyl, thienyl, pyrrolyl, imidazolyl, and benzofuranyl, each optionally substituted with one to two groups selected from halogen, —CN, —OH, $C_{1-6}$alkyl, $C_{1-6}$alkoxy, —$CF_3$, —$CO_2C_{1-6}$alkyl, and —$CONH_2$, or
   (e) —$(CH_2)_2OCH_2$Ar, wherein Ar is phenyl or heteroaryl selected from pyridinyl, triazolyl, pyrimidinyl, furanyl, thiazolyl, thienyl, pyrrolyl, imidazolyl, and benzofuranyl, each optionally substituted with one to two groups selected from halogen, —CN, —OH, $C_{1-6}$alkyl, $C_{1-6}$alkoxy, —$CO_2C_{1-6}$alkyl, —C(O)$NH_2$; or
if X is C, and Y is O, $R^1$ may form a fused dihydropyran ring with the O it is bound to and X, said dihydropyran ring optionally substituted with one or two methyl groups;
$R^2$ is
   (a) H, $C_{1-6}$alkyl, $C_{1-6}$alkoxy, hydroxy$C_{1-6}$alkyl, halogen, —CN, —$CO_2C_{1-6}$alkyl, —$S(O)_{0-2}C_{1-6}$alkyl, —$NO_2$, —OH, —$CF_3$, —$NH_2$, —NH($C_{1-6}$alkyl), —N($C_{1-6}$alkyl)($C_{1-6}$alkyl), —NHC(O)NH$C_{1-6}$alkyl, —C(O)$NH_2$, —CONH($C_{1-6}$alkyl), —CON($C_{1-6}$alkyl)($C_{1-6}$alkyl), or
   b) phenyl, pyridinyl, triazolyl, or pyrimidinyl, each optionally substituted with one or two groups selected from halogen, $C_{1-6}$alkyl, —CN or $C_{1-6}$alkoxy;
$R^3$ is in the 4-position and is —$CO_2H$, —$(CH_2)_{1-2}CO_2H$, —$(CH_2)_{0-1}C(CH_3)(CH_3)CO_2H$, —$C(CH_3)(CH_3)CO_2H$, —$O(CH_2)_{1-4}CO_2H$, —$O(CH_2)_{0-1}C(C_{1-6}$alkyl)

($C_{1-6}$alkyl)$CO_2H$, —OC($C_{1-6}$alkyl)($C_{1-6}$alkyl)$CO_2H$, —($CH_2$)$_{0-1}$tetrazol-5-yl, or —C($CH_3$)($CH_3$)tetrazol-5-yl;

$R^4$, $R^5$, $R^6$, and $R^7$ are independently selected from H and $C_{1-6}$alkyl, or $R^4$ and $R^6$ may be joined, together with the carbons they are bonded to, to form a cyclopropane ring;

$R^8$, $R^9$, $R^{10}$, and $R^{11}$ are independently H, halogen, $C_{1-6}$alkyl, $C_{1-6}$alkoxy, —CN, —$CO_2C_{1-6}$alkyl, —C(O)$NH_2$, —$SO_2NH_2$, —$NO_2$, —OH, —$NH_2$, —$CF_3$, or —$CH_2OH$;

or a tautomer thereof or a salt thereof.

2. The compound of claim 1 wherein:
Y is O;
$R^1$ is
  (a) H,
  (b) $C_{1-8}$alkyl, branched or unbranched, optionally partially or fully halogenated, and optionally substituted with one to two groups selected from —OH, CN, $C_{1-6}$alkoxy, —$CO_2C_{1-6}$alkyl, —CON($C_{1-3}$alkyl)($C_{1-3}$alkyl),
  (c) —($CH_2$)$_{0-1}C_{3-8}$cycloalkyl,
  (d) —$CH_2$Ar, wherein Ar is phenyl or heteroaryl selected from pyridinyl, triazolyl, pyrimidinyl, furanyl, thiazolyl, thienyl, pyrrolyl, imidazolyl, and benzofuranyl, each optionally substituted with one to two groups selected from halogen, —CN, —OH, $C_{1-6}$alkyl, $C_{1-6}$alkoxy, —$CF_3$, —$CO_2C_{1-6}$alkyl, and —$CONH_2$, or
  (e) —($CH_2$)$_2OCH_2$Ar wherein Ar is phenyl or heteroaryl selected from pyridinyl, triazolyl, pyrimidinyl, furanyl, thiazolyl, thienyl, pyrrolyl, imidazolyl, and benzofuranyl, each optionally substituted with one to two groups selected from halogen, —CN, —OH, $C_{1-6}$alkyl, $C_{1-6}$alkoxy, —$CO_2C_{1-6}$alkyl, —C(O)$NH_2$; or $R^1$ may be a fused dihydropyran ring with the O it is bound to and X, said dihydropyran ring optionally substituted with one or two methyl groups;
$R^2$ is
  (a) H, $C_{1-6}$alkyl, $C_{1-6}$alkoxy, hydroxy$C_{1-6}$alkyl, halogen, —CN, —$CO_2C_{1-6}$alkyl, —S(O)$_{0-2}C_{1-6}$alkyl, —$NO_2$, —OH, —$CF_3$, —$NH_2$, —NH($C_{1-6}$alkyl), —N($C_{1-6}$alkyl)($C_{1-6}$alkyl), —NHC(O)NH$C_{1-6}$alkyl, —C(O)$NH_2$, —CONH($C_{1-6}$alkyl), —CON($C_{1-6}$alkyl)($C_{1-6}$alkyl), or
  (b) phenyl, pyridinyl, triazolyl and pyrimidinyl, each optionally substituted with one or two groups selected from halogen, $C_{1-6}$alkyl, —CN or $C_{1-6}$alkoxy;

$R^4$, $R^5$, $R^6$, and $R^7$ are independently H or methyl, or $R^4$ and $R^6$ may be joined, together with the carbons they are bonded to, to form a cyclopropane ring;

$R^8$, $R^9$, $R^{10}$, and $R^{11}$ are independently H, halogen, $C_{1-6}$alkyl, $C_{1-6}$alkoxy, —CN, —$CO_2C_{1-6}$alkyl, —C(O)$NH_2$, —$SO_2NH_2$, —$NO_2$, —OH, —$NH_2$, —$CF_3$, or —$CH_2OH$;

or a tautomer thereof or a salt thereof.

3. The compound of claim 1 wherein:
Y is O;
$R^1$ is
  (a) H,
  (b) $C_{1-8}$alkyl, branched or unbranched, optionally partially or fully fluorinated, and optionally substituted with one to two groups selected from —OH, CN and —$OCH_3$,
  (c) —($CH_2$)$_{0-1}C_{3-8}$cycloalkyl, or
  (d) —$CH_2$Ar, wherein Ar is phenyl or heteroaryl selected from pyridinyl and thiazolyl, each optionally substituted with one to two groups selected from halogen, —CN, —$CH_3$, —$OCH_3$, —$CF_3$, and —$CONH_2$; or $R^1$ may form a fused dihydropyran ring with the O it is bound to and X, said dihydropyran ring optionally substituted with one or two methyl groups;
$R^2$ is
  (a) —Cl, —Br, —CN, —$CO_2C_{1-6}$alkyl, —$NO_2$, —OH, —$CF_3$, —$NH_2$; or
  (b) phenyl, pyridinyl, or pyrimidinyl;

$R^4$, $R^5$, $R^6$, and $R^7$ are independently H or methyl, or $R^4$ and $R^6$ may be joined, together with the carbons they are bonded to, to form a cyclopropane ring;

$R^8$, $R^9$, $R^{10}$, and $R^{11}$ are independently H, F, Cl, $CH_3$, —$OCH_3$, —CN, —$NO_2$, —$NH_2$, or —$CF_3$;

or a tautomer thereof or a salt thereof.

4. The compound of claim 1 wherein:
Y is O;
$R^1$ is
  (a) $C_{1-8}$alkyl, branched or unbranched, optionally partially or fully fluorinated;
  (b) —($CH_2$)$_{0-1}C_{3-8}$cycloalkyl, or
  (c) —$CH_2$Ar, wherein Ar is phenyl or heteroaryl selected from pyridinyl and thiazolyl, each optionally substituted with one to two groups selected from F, —CN, —$CH_3$, —$OCH_3$, and —$CF_3$, $R^2$ is Cl or Br;
$R^4$, $R^5$, $R^6$, and $R^7$ are independently H or methyl, or $R^4$ and $R^6$ may be joined, together with the carbons they are bonded to, to form a cyclopropane ring;

$R^8$, $R^9$, $R^{10}$, and $R^{11}$ are independently H, F, Cl, $CH_3$, —$OCH_3$, —CN, —$NO_2$, or —$NH_2$;

or a tautomer thereof or a salt thereof.

5. A compound selected from the group consisting of:
(4'-{2-[(2-butoxy-5-chlorobenzoyl)amino]ethyl}biphenyl-4-yl)acetic acid;
2-[(4'-{2-[(2-butoxy-5-chlorobenzoyl)amino]ethyl}-2,5-difluorobiphenyl-4-yl)oxy]-2-methylpropanoic acid;
4'-{2-[(2-butoxy-5-chlorobenzoyl)amino]ethyl}-3-chlorobiphenyl-4-carboxylic acid;
2-[(4'-{2-[(2-butoxy-5-chlorobenzoyl)amino]ethyl}-3-fluorobiphenyl-4-yl)oxy]-2-methylpropanoic acid;
2-[(4'-{2-[(5-chloro-2-methoxybenzoyl)amino]ethyl}-2,3-dimethylbiphenyl-4-yl)oxy]-2-methylpropanoic acid;
2-[(4'-{2-[(2-butoxy-5-chlorobenzoyl)amino]ethyl}biphenyl-4-yl)oxy]-2-methylpropanoic acid;
4'-{2-[(2-butoxy-5-chlorobenzoyl)amino]ethyl}-2-nitrobiphenyl-4-carboxylic acid;
2-{[4'-(2-{[2-(benzyloxy)-5-chlorobenzoyl]amino}ethyl)biphenyl-4-yl]oxy}-2-methylpropanoic acid;
2-(benzyloxy)-5-chloro-N-{2-[4'-(1H-tetrazol-5-yl)biphenyl-4-yl]ethyl}benzamide;
2-[(4'-{2-[(5-chloro-2-methoxybenzoyl)amino]ethyl}-2,5-difluorobiphenyl-4-yl)oxy]-2-methylpropanoic acid;
4'-{2-[(2-butoxy-5-chlorobenzoyl)amino]ethyl}-2-chlorobiphenyl-4-carboxylic acid;
2-[(4'-{2-[(5-chloro-2-propoxybenzoyl)amino]ethyl}biphenyl-4-yl)oxy]-2-methylpropanoic acid;
4'-[2-({5-chloro-2-[(3-fluorobenzyl)oxy]benzoyl}amino)ethyl]biphenyl-4-carboxylic acid;
4'-[2-({5-chloro-2-[(3-methoxybenzyl)oxy]benzoyl}amino)ethyl]biphenyl-4-carboxylic acid;
2-[(4'-{2-[(2-butoxy-5-chlorobenzoyl)amino]ethyl}-2-fluorobiphenyl-4-yl)oxy]-2-methylpropanoic acid;
2-butoxy-5-chloro-N-(2-{4'-[1-methyl-1-(1H-tetrazol-5-yl)ethyl]biphenyl-4-yl}ethyl)benzamide;

4'-{2-[(2-butoxy-5-chlorobenzoyl)amino]ethyl}-3-fluorobiphenyl-4-carboxylic acid;
2-[(4'-{2-[(2-butoxy-5-chlorobenzoyl)amino]ethyl}-3-methoxybiphenyl-4-yl)oxy]-2-methylpropanoic acid;
4'-(2-{[5-chloro-2-(hexyloxy)benzoyl]amino}ethyl)biphenyl-4-carboxylic acid;
2-[(4'-{2-[(2-butoxy-5-chlorobenzoyl)amino]ethyl}biphenyl-3-yl)oxy]-2-methylpropanoic acid;
2-{[4'-(2-{[5-chloro-2-(4,4,4-trifluorobutoxy)benzoyl]amino}ethyl)biphenyl-4-yl]oxy}-2-methylpropanoic acid;
4'-(2-{[5-chloro-2-(pentyloxy)benzoyl]amino}ethyl)biphenyl-4-carboxylic acid;
4'-(2-{[5-chloro-2-(heptyloxy)benzoyl]amino}ethyl)biphenyl-4-carboxylic acid;
4'-[2-({5-chloro-2-[(4-methylpentyl)oxy]benzoyl}amino)ethyl]biphenyl-4-carboxylic acid;
2-[(2,3-dichloro-4'-{2-[(5-chloro-2-methoxybenzoyl)amino]ethyl}biphenyl-4-yl)oxy]-2-methylpropanoic acid;
2-butoxy-5-chloro-N-{2-[4'-(1H-tetrazol-5-ylmethyl)biphenyl-4-yl]ethyl}benzamide;
4'-{2-[(2-butoxy-5-chlorobenzoyl)amino]ethyl}-2-methylbiphenyl-4-carboxylic acid;
2-[(4'-{2-[(2-butoxy-5-chlorobenzoyl)amino]ethyl}-3-methylbiphenyl-4-yl)oxy]-2-methylpropanoic acid;
2-[(4'-{2-[(2-butoxy-5-chlorobenzoyl)amino]ethyl}-2-methylbiphenyl-4-yl)oxy]-2-methylpropanoic acid;
2-[(2-chloro-4'-{2-[(5-chloro-2-methoxybenzoyl)amino]ethyl}biphenyl-4-yl)oxy]-2-methylpropanoic acid;
4'-[2-({5-chloro-2-[(3-methylbenzyl)oxy]benzoyl}amino)ethyl]biphenyl-4-carboxylic acid;
2-[(4'-{2-[(5-chloro-2-methoxybenzoyl)amino]ethyl}-2-methylbiphenyl-4-yl)oxy]-2-methylpropanoic acid;
2-[(4'-{2-[(2-butoxy-5-chlorobenzoyl)amino]ethyl}-2,3-dimethylbiphenyl-4-yl)oxy]-2-methylpropanoic acid;
2-[(4'-{2-[(5-chloro-2-methoxybenzoyl)amino]ethyl}-3-methylbiphenyl-4-yl)oxy]-2-methylpropanoic acid;
4'-[2-({5-chloro-2-[(4-methylbenzyl)oxy]benzoyl}amino)ethyl]biphenyl-4-carboxylic acid;
4'-[2-({5-chloro-2-[(6-hydroxyhexyl)oxy]benzoyl}amino)ethyl]biphenyl-4-carboxylic acid;
2-[(4'-{2-[(5-chloro-2-methoxybenzoyl)amino]ethyl}-2-fluorobiphenyl-4-yl)oxy]-2-methylpropanoic acid;
2-[(4'-{2-[(2-butoxy-5-chlorobenzoyl)amino]ethyl}-2-chlorobiphenyl-4-yl)oxy]-2-methylpropanoic acid;
2-[(4'-{2-[(5-chloro-2-isopropoxybenzoyl)amino]ethyl}biphenyl-4-yl)oxy]-2-methylpropanoic acid;
4'-{2-[(2-butoxy-5-chlorobenzoyl)amino]ethyl}-3-methoxybiphenyl-4-carboxylic acid;
2-{[4'-(2-{[5-chloro-2-(3,3,4,4,4-pentafluorobutoxy)benzoyl]amino}ethyl)biphenyl-4-yl]oxy}-2-methylpropanoic acid;
2-[(4'-{2-[(5-chloro-2-methoxybenzoyl)amino]ethyl}-2,5-dimethylbiphenyl-4-yl)oxy]-2-methylpropanoic acid;
4'-[2-({2-[2-(benzyloxy)ethoxy]-5-chlorobenzoyl}amino)ethyl]biphenyl-4-carboxylic acid;
2-{[4'-(2-{[5-chloro-2-(4-fluorobutoxy)benzoyl]amino}ethyl)biphenyl-4-yl]oxy}-2-methylpropanoic acid;
2-[(4'-{2-[(5-chloro-2-methoxybenzoyl)amino]ethyl}-3-fluorobiphenyl-4-yl)oxy]-2-methylpropanoic acid;
3-(4'-{2-[(2-butoxy-5-chlorobenzoyl)amino]ethyl}biphenyl-4-yl)-2,2-dimethylpropanoic acid;
4'-{2-[(5-bromo-2-butoxybenzoyl)amino]ethyl}biphenyl-4-carboxylic acid;
2-[(4'-{2-[(5-chloro-2-ethoxybenzoyl)amino]ethyl}biphenyl-4-yl)oxy]-2-methylpropanoic acid;
4'-(2-{[5-chloro-2-(4,4,4-trifluorobutoxy)benzoyl]amino}ethyl)biphenyl-4-carboxylic acid;
3-(4'-{2-[(2-butoxy-5-chlorobenzoyl)amino]ethyl}biphenyl-4-yl)propanoic acid;
2-(4'-{2-[(2-butoxy-5-chlorobenzoyl)amino]ethyl}biphenyl-4-yl)-2-methylpropanoic acid;
2-[(4'-{2-[(5-chloro-2-methoxybenzoyl)amino]ethyl}-3'-fluorobiphenyl-4-yl)oxy]-2-methylpropanoic acid;
4'-[2-({5-chloro-2-[(4-fluorobenzyl)oxy]benzoyl}amino)ethyl]biphenyl-4-carboxylic acid;
4'-[2-({5-chloro-2-[(3,4-difluorobenzyl)oxy]benzoyl}amino)ethyl]biphenyl-4-carboxylic acid;
(4'-{2-[(2-butoxy-5-chlorobenzoyl)amino]ethyl}-3-nitrobiphenyl-4-yl)acetic acid;
4'-(2-{[5-chloro-2-(3-methylbutoxy)benzoyl]amino}ethyl)biphenyl-4-carboxylic acid;
4'-[2-({5-chloro-2-[(2-fluorobenzyl)oxy]benzoyl}amino)ethyl]biphenyl-4-carboxylic acid;
4'-{2-[(5-chloro-2-{[3-(trifluoromethyl)benzyl]oxy}benzoyl)amino]ethyl}biphenyl-4-carboxylic acid;
4'-(2-{[5-chloro-2-(cyclobutylmethoxy)benzoyl]amino}ethyl)biphenyl-4-carboxylic acid;
4'-(2-{[(5-bromo-2,2-dimethyl-2,3-dihydro-1-benzofuran-7-yl)carbonyl]amino}ethyl)-biphenyl-4-carboxylic acid;
3-(4'-{2-[(5-chloro-2-methoxybenzoyl)amino]ethyl}biphenyl-4-yl)-2,2-dimethylpropanoic acid;
2-chloro-4'-{2-[(5-chloro-2-methoxybenzoyl)amino]ethyl}biphenyl-4-carboxylic acid;
2-[(4'-{2-[(2-butoxy-5-chlorobenzoyl)amino]ethyl}-3-cyanobiphenyl-4-yl)oxy]-2-methylpropanoic acid;
4'-[2-({5-chloro-2-[(3-cyanobenzyl)oxy]benzoyl}amino)ethyl]biphenyl-4-carboxylic acid;
4'-(2-{[5-chloro-2-(cyclohexylmethoxy)benzoyl]amino}ethyl)biphenyl-4-carboxylic acid;
4'-{2-[(2-butoxy-5-chlorobenzoyl)amino]-1-methylethyl}biphenyl-4-carboxylic acid;
4'-(2-{[5-chloro-2-(3,3,4,4,4-pentafluorobutoxy)benzoyl]amino}ethyl)biphenyl-4-carboxylic acid;
4'-(2-{[(2-butoxy-5-chloropyridin-3-yl)carbonyl]amino}ethyl)biphenyl-4-carboxylic acid;
2-[(4'-{2-[(5-chloro-2-methoxybenzoyl)amino]ethyl}biphenyl-4-yl)oxy]-2-methylpropanoic acid;
2-butoxy-5-chloro-N-(2-{4-[6-(1H-tetrazol-5-yl)pyridin-3-yl]phenyl}ethyl)benzamide;
4'-(2-{[5-chloro-2-(pyridin-2-ylmethoxy)benzoyl]amino}ethyl)biphenyl-4-carboxylic acid;
4'-{2-[(5-chloro-2-{[2-(trifluoromethyl)benzyl]oxy}benzoyl)amino]ethyl}biphenyl-4-carboxylic acid;
2-[(3-chloro-4'-{2-[(5-chloro-2-methoxybenzoyl)amino]ethyl}biphenyl-4-yl)oxy]-2-methylpropanoic acid;
4'-{2-[(2-butoxy-5-chlorobenzoyl)amino]ethyl}-2-cyanobiphenyl-4-carboxylic acid;
4'-{2-[(5-chloro-2-ethoxybenzoyl)amino]ethyl}biphenyl-4-carboxylic acid;
4'-(2-{[5-chloro-2-(1-methylbutoxy)benzoyl]amino}ethyl)biphenyl-4-carboxylic acid;
3-chloro-4'-{2-[(5-chloro-2-methoxybenzoyl)amino]ethyl}biphenyl-4-carboxylic acid;
2-[(2',6'-dichloro-4'-{2-[(5-chloro-2-methoxybenzoyl)amino]ethyl}biphenyl-4-yl)oxy]-2-methylpropanoic acid;

4'-{2-[(5-chloro-2-isobutoxybenzoyl)amino]ethyl}biphenyl-4-carboxylic acid;

4'-{2-[(5-chloro-2-propoxybenzoyl)amino]ethyl}biphenyl-4-carboxylic acid;

4'-[2-({5-chloro-2-[(4-methyl-1,3-thiazol-2-yl)methoxy]benzoyl}amino)ethyl]biphenyl-4-carboxylic acid;

2-[(4'-{2-[(2-butoxy-5-chlorobenzoyl)amino]ethyl}-2,5-dimethylbiphenyl-4-yl)oxy]-2-methylpropanoic acid;

4'-(2-{[5-chloro-2-(4-fluorobutoxy)benzoyl]amino}ethyl)biphenyl-4-carboxylic acid;

2-[(4'-{2-[(2-butoxy-5-chlorobenzoyl)amino]ethyl}-3-chlorobiphenyl-4-yl)oxy]-2-methylpropanoic acid;

(4'-{2-[(5-chloro-2-methoxybenzoyl)amino]ethyl}biphenyl-4-yl)acetic acid;

4'-(2-{[5-chloro-2-(cyclopropylmethoxy)benzoyl]amino}ethyl)biphenyl-4-carboxylic acid;

4'-(2-{[5-chloro-2-(pyridin-3-ylmethoxy)benzoyl]amino}ethyl)biphenyl-4-carboxylic acid;

4'-{2-[(2-butoxy-5-chlorobenzoyl)amino]-1,1-dimethylethyl}biphenyl-4-carboxylic acid;

4'-{2-[(2-butoxy-5-chlorobenzoyl)amino]propyl}biphenyl-4-carboxylic acid;

4'-(2-{[(5-bromo-2,3-dihydro-1-benzofuran-7-yl)carbonyl]amino}ethyl)biphenyl-4-carboxylic acid;

2-{[4'-(2-{[5-chloro-2-(3,3,3-trifluoropropoxy)benzoyl]amino}ethyl)biphenyl-4-yl]oxy}-2-methylpropanoic acid;

2-amino-4'-{2-[(2-butoxy-5-chlorobenzoyl)amino]ethyl}biphenyl-4-carboxylic acid;

2-[(4'-{2-[(2-butoxy-5-chlorobenzoyl)amino]ethyl}-2,6-dimethylbiphenyl-4-yl)oxy]-2-methylpropanoic acid;

2-(4'-{2-[(5-chloro-2-methoxybenzoyl)amino]ethyl}biphenyl-4-yl)-2-methylpropanoic acid;

4'-{2-[(2-butoxy-5-pyridin-3-ylbenzoyl)amino]ethyl}biphenyl-4-carboxylic acid;

4'-(2-{[5-chloro-2-(cyclobutyloxy)benzoyl]amino}ethyl)biphenyl-4-carboxylic acid;

4'-{2-[(2-butoxy-5-chlorobenzoyl)amino]ethyl}biphenyl-4-carboxylic acid;

2-(4-{5-[2-(2-butoxy-5-chloro-benzoylamino)-ethyl]-pyridin-2-yl}-phenoxy)-2-methyl-propionic acid;

2-{4'-[2-(2-butoxy-5-chloro-benzoylamino)-ethyl]-3'-ethyl-biphenyl-4-yloxy}-2-methyl-propionic acid;

2-{3',5'-Dichloro-4'-[2-(5-chloro-2-methoxy-benzoylamino)-ethyl]-biphenyl-4-yloxy}-2-methyl-propionic acid; and a tautomer thereof or a salt thereof.

6. A pharmaceutical composition comprising a compound of claim 1 and a pharmaceutically acceptable carrier.

7. A method of using any one of the compounds of claim 1 for the treatment of psoriasis, contact sensitivity, dermatitis, systemic sclerosis, cutaneous systemic lupus erythematosus, and allergic asthma.

8. A method of using the pharmaceutical composition of claim 6 for the treatment of psoriasis, contact sensitivity, dermatitis, systemic sclerosis, cutaneous systemic lupus erythematosus, and allergic asthma.

\* \* \* \* \*